(12) United States Patent
Liu et al.

(10) Patent No.: US 9,376,376 B2
(45) Date of Patent: Jun. 28, 2016

(54) SUBSTITUTE DIPHENYLAMINE COMPOUNDS USE THEREOF AS ANTITUMOR AGENTS

(71) Applicants: SINOCHEM CORPORATION, Beijing (CN); SHENYANG RESEARCH INSTITUTE OF CHEMICAL INDUSTRY CO., LTD., Liaoning (CN)

(72) Inventors: Changling Liu, Liaoning (CN); Baoshan Chai, Liaoning (CN); Huichao Li, Liaoning (CN); Aiying Guan, Liaoning (CN)

(73) Assignees: SINOCHEM CORPORATION, Beijing (CN); SHENYANG RESEARCH INSTITUTE OF CHEMICAL INDUSTRY CO., LTD., Liaoning (CN)

( * ) Notice: Subject to any disclaimer, the term of this patent is extended or adjusted under 35 U.S.C. 154(b) by 0 days.

(21) Appl. No.: 14/376,074

(22) PCT Filed: Mar. 6, 2013

(86) PCT No.: PCT/CN2013/072232
§ 371 (c)(1),
(2) Date: Jul. 31, 2014

(87) PCT Pub. No.: WO2013/135147
PCT Pub. Date: Sep. 19, 2013

(65) Prior Publication Data
US 2015/0011628 A1    Jan. 8, 2015

(30) Foreign Application Priority Data

Mar. 14, 2012  (CN) .......................... 2012 1 0067595
Mar. 14, 2014  (CN) .......................... 2012 1 0067267

(51) Int. Cl.

| C07C 255/58 | (2006.01) |
| A61K 31/136 | (2006.01) |
| C07C 211/56 | (2006.01) |
| C07C 205/06 | (2006.01) |
| C07C 205/37 | (2006.01) |
| A61K 31/277 | (2006.01) |
| C07C 255/57 | (2006.01) |
| C07C 255/59 | (2006.01) |
| C07C 217/92 | (2006.01) |
| C07C 323/36 | (2006.01) |
| C07C 229/58 | (2006.01) |
| C07C 233/65 | (2006.01) |
| C07D 213/643 | (2006.01) |

(52) U.S. Cl.
CPC ............ *C07C 255/58* (2013.01); *A61K 31/136* (2013.01); *A61K 31/277* (2013.01); *C07C 205/06* (2013.01); *C07C 205/37* (2013.01); *C07C 211/56* (2013.01); *C07C 217/92* (2013.01); *C07C 229/58* (2013.01); *C07C 233/65* (2013.01); *C07C 255/57* (2013.01); *C07C 255/59* (2013.01); *C07C 323/36* (2013.01); *C07D 213/643* (2013.01)

(58) Field of Classification Search
CPC .... C07C 255/58; C07C 205/06; C07C 205/37
USPC .......................................... 514/524; 564/433
See application file for complete search history.

(56) References Cited

U.S. PATENT DOCUMENTS

| 3,948,957 A | 4/1976 | Beck |
| 3,948,990 A | 4/1976 | Barlow et al. |
| 4,041,172 A | 8/1977 | Barlow |

(Continued)

FOREIGN PATENT DOCUMENTS

| CN | 1188757 | 7/1998 |
| EP | 26743 | 4/1981 |

(Continued)

OTHER PUBLICATIONS

McMahon et al (2000).*

(Continued)

*Primary Examiner* — Paul V Ward
(74) *Attorney, Agent, or Firm* — B. Aaron Schulman, Esq.; Stites & Harbison, PLLC

(57) ABSTRACT

The invention relates to substituted diphenylamine compounds using as antitumor agents. The structure of the compounds is represented as the general formula (I):

$$\underset{R_5\quad R_6\quad\quad R_{11}\quad R_{10}}{\underset{R_4-\phantom{xxxxxxxxxx}-N-\phantom{xxxxxxxxxx}-R_9}{R_3\quad R_2\quad\ R_1\quad R_7\quad R_8}} \quad \text{I}$$

The groups are as defined as specification.

The compound represented by formula (I) showed potent antitumor activity, especially to cure or alleviate the cancer causing by cancer cells of human tissue or organ. The preferred cancers are: colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer, osteosarcoma, nasopharynx cancer or stomach cancer.

18 Claims, No Drawings

(56) References Cited

U.S. PATENT DOCUMENTS

| | | |
|---|---|---|
| 4,117,167 A | 9/1978 | Barlow et al. |
| 4,152,460 A | 5/1979 | Dreikorn |
| 4,187,318 A | 2/1980 | Dreikorn |
| 4,215,145 A | 7/1980 | Grantham |
| 4,304,791 A | 12/1981 | Clinton |
| 4,316,988 A | 2/1982 | Clinton |
| 4,407,820 A | 10/1983 | Dreikorn et al. |
| 4,459,304 A | 7/1984 | Hartmann et al. |
| 4,670,596 A | 6/1987 | Dreikorn et al. |
| 6,699,890 B2 | 3/2004 | Schumacher et al. |
| 6,939,887 B2 | 9/2005 | Okazaki et al. |
| 7,067,539 B2 | 6/2006 | Kozlowski et al. |
| 7,205,320 B2 | 4/2007 | Schumacher et al. |
| 7,507,767 B2 | 3/2009 | Kozlowski et al. |
| 7,718,702 B2 | 5/2010 | Kozlowski et al. |
| 8,236,826 B2 | 8/2012 | Matsuyama et al. |
| 8,765,815 B2 | 7/2014 | Attali et al. |
| 2003/0149052 A1 | 8/2003 | Schumacher et al. |
| 2008/0076800 A1 | 3/2008 | Huang et al. |
| 2011/0039819 A1 | 2/2011 | Hitchcock et al. |
| 2011/0046146 A9 | 2/2011 | Schumacher et al. |
| 2012/0270858 A1 | 10/2012 | Tao et al. |
| 2013/0203831 A1 | 8/2013 | Botta et al. |

FOREIGN PATENT DOCUMENTS

| | | |
|---|---|---|
| GB | 1525884 | 9/1978 |
| GB | 1544078 | 4/1979 |
| JP | 01186849 | 7/1989 |
| WO | WO 2005035498 | 4/2005 |
| WO | WO 2009/037705 | 3/2009 |

OTHER PUBLICATIONS

Pinedo et al (2000).*

International Search Report for PCT/CN2013/072232 dated May 23, 2013.

* cited by examiner

SUBSTITUTE DIPHENYLAMINE COMPOUNDS USE THEREOF AS ANTITUMOR AGENTS

FIELD OF THE INVENTION

The present invention relates to the field of medicine. Specifically to a substituted diphenylamine compounds and uses thereof as antitumor agents.

BACKGROUND OF THE INVENTION

The following compounds, which can be used as intermediates to synthetise a kind of multi-halogenated acridone compounds having fluorescence and pharmaceutical activity, were reported in patent CN101391981A. The invention discloses compounds KC1(IV-A), KC2(IV-B), KC3(IV-D), KC4(IV-E), KC5(IV-H) and KC6(IV-C), but there are no bioactivity reported. The compound KC1(XXIX) was also reported in *Pesticide Science* (1988), 24(2), 111-21, showing fungicidal activity against grape downy mildew (*Plasmopora viticola*).

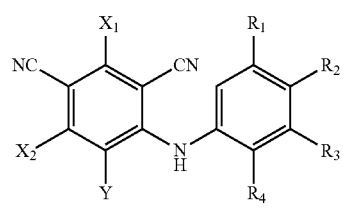

$X_1, X_2, Y = F, Cl$ $R_1 \sim R_4 = Alk, Ary$

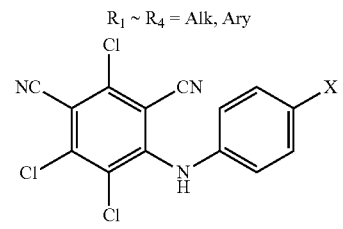

KC1: X = H
KC2: X = Cl
KC3: X = CH$_3$
KC4: X = OCH$_3$

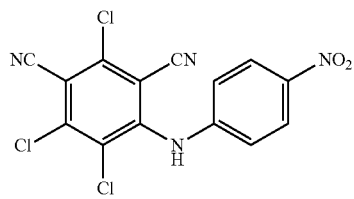

KC5

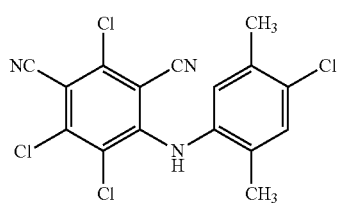

KC6

The compounds having the following general formulas were reported as insecticides, acaricides, fungicides, herbicides, rodenticide or others in the prior art:

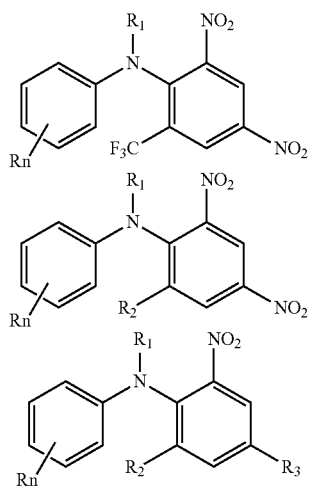

Such as patents BR7900462, CH626323, CN1188757, DE2509416, DE2642147, DE2642148, EP26743, EP60951, GB1544078, GB1525884, JP58113151, JP64001774, JP01186849, WO2002060878, WO2005035498, WO2009037707, U.S. Pat. No. 3,948,957, U.S. Pat. No. 3,948,990, U.S. Pat. No. 4,041,172, U.S. Pat. No. 4,152,460, U.S. Pat. No. 4,187,318, U.S. Pat. No. 4,215,145, U.S. Pat. No. 4,304,791, U.S. Pat. No. 4,316,988, U.S. Pat. No. 4,407,820, U.S. Pat. No. 4,459,304, U.S. Pat. No. 4,670,596 and so on, and ACS Symposium Series (1992), 504 (Synth. Chem. Agrochem. III), 336-48; Journal of the Chemical Society (1951), 110-15, etc. all reported the compounds having above general formulas.

In addition, the compounds of the following general formulas were mentioned in Chemische Berichte (1962), 95 1711-21; Chemische Berichte (1963), 96(7), 1936-44; Journal of Organic Chemistry (1954), 19, 1641-5; Journal of the Chemical Society; Transactions (1913), 103 982-8 and Journal of the Chemical Society, Transactions (1921), 119, 187-92 and so on, but without any bioactivity reported:

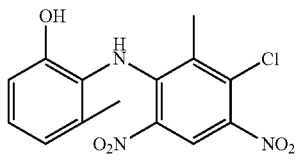

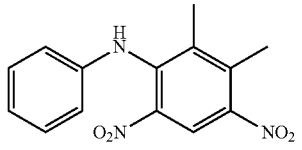

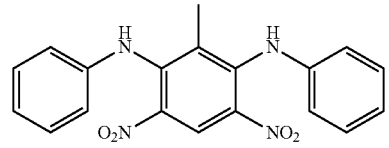

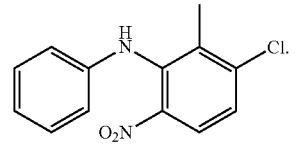

The compounds having the following general formulas as fungicide were reported in patent WO2012171484:

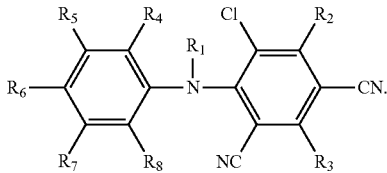

The compounds having the following general formulas as fungicide were reported in patent WO2011116671:

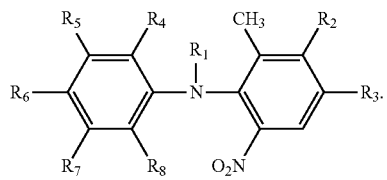

The compounds having the structure of general formula I were not reported in the prior art as antitumor agents.

SUMMARY OF THE INVENTION

The object of the present invention is to provide substituted diphenylamine compounds having general formula I, which can be applied to antitumor agents.

Detailed description of the invention is as follows:

Substituted diphenylamine compounds use thereof as antitumor agents, the compounds having the structure of general formula I:

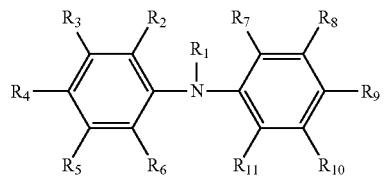

Wherein:

$R_1$ is selected from H, $C_1$-$C_8$alkyl, $C_3$-$C_8$cycloalkyl, $C_1$-$C_8$haloalkyl, $C_1$-$C_8$alkylcarbonyl, $C_1$-$C_8$halo alkylcarbonyl, $C_1$-$C_8$ alkoxycarbonyl, $C_1$-$C_8$alkylamino carbonyl, $C_1$-$C_8$alkylthio, $C_1$-$C_8$halo alkylthio, $C_1$-$C_8$alkylsulfonyl, $C_1$-$C_8$ alkoxy$C_1$-$C_8$alkyl, $C_1$-$C_8$ alkoxy$C_1$-$C_8$alkylcarbonyl, $C_1$-$C_8$alkoxycarbonyl$C_1$-$C_8$alkyl, $C_1$-$C_8$alkylaminothio, $C_2$-$C_8$dialkylaminothio, $C_2$-$C_8$ alkenyl, $C_2$-$C_8$alkynyl, $C_2$-$C_8$haloalkenyl, $C_2$-$C_8$haloalkynyl, aryl $C_1$-$C_8$alkyl or CO—X—$CO_2R_{12}$, in which X is selected from $(CHR_{12})n$, $CR_{12}$=$CR_{13}$ or $C_6H_4$, n=1-6;

$R_2$ and $R_6$ may be the same or different, respectively selected from H, halogen, CN, $NO_2$, COOH, C(=O)$NR_{12}R_{13}$, $C_1$-$C_8$alkyl, $C_1$-$C_8$halo alkyl, $C_1$-$C_8$alkoxy, $C_1$-$C_8$halo alkoxy, $C_1$-$C_8$alkylthio, $C_1$-$C_8$halo alkylthio, $C_2$-$C_8$ alkenyl, $C_2$-$C_8$ alkynyl, $C_1$-$C_8$alkylsulfonyl, $C_1$-$C_8$alkylcarbonyl, $C_1$-$C_8$alkoxycarbonyl, $C_1$-$C_8$ alkoxy$C_1$-$C_8$alkyl, $C_1$-$C_8$ alkoxycarbonyl$C_1$-$C_8$alkyl, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_3$ and $R_5$ may be the same or different, respectively selected from H, halogen, CN, $NO_2$, COOH, C(=O)$NR_{12}R_{13}$, $C_1$-$C_8$alkyl, $C_1$-$C_8$halo alkyl, $C_1$-$C_8$ alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_2$-$C_8$alkenyl, $C_2$-$C_8$alkynyl, $C_1$-$C_8$alkylsulfonyl, $C_1$-$C_8$alkylcarbonyl, $C_1$-$C_8$ alkoxycarbonyl, $C_1$-$C_8$ alkoxy$C_1$-$C_8$alkyl, $C_1$-$C_8$alkoxycarbonyl$C_1$-$C_8$alkyl, $C_1$-$C_8$alkylcarbonyloxy, $C_1$-$C_8$ alkoxycarbonyloxy, $C_1$-$C_8$alkylaminocarbonyloxy, $C_1$-$C_8$alkylsulfonyloxy, $C_1$-$C_8$ alkoxy$C_1$-$C_8$ alkoxy, $C_1$-$C_8$halo alkoxy$C_1$-$C_8$halo alkoxy, $C_1$-$C_8$ alkoxycarbonyl$C_1$-$C_8$ alkoxy, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_4$ is selected from H, halogen, CN, $NO_2$, COOH, $CO_2Na$, $CO_2NH_4$, C(=O)$NR_{12}R_{13}$, $C_1$-$C_8$alkyl, $C_1$-$C_8$halo alkyl, $C_1$-$C_8$alkoxy, $C_1$-$C_8$halo alkoxy, $C_2$-$C_8$ alkenyl, $C_2$-$C_8$ alkynyl, $C_1$-$C_8$alkylsulfonyl, $C_1$-$C_8$alkylcarbonyl, $C_1$-$C_8$ alkoxycarbonyl, $C_1$-$C_8$alkoxy$C_1$-$C_8$alkyl, $C_1$-$C_8$ alkoxycarbonyl$C_1$-$C_8$alkyl, $C_1$-$C_8$alkoxy$C_1$-$C_8$ alkoxy, $C_1$-$C_8$haloalkoxy$C_1$-$C_8$haloalkoxy, $SO_2NR_{12}R_{13}$, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_7$ is selected from Cl or $CH_3$;

$R_8$ is selected from H, halogen, OH, CN, $NO_2$, COOH, $C_1$-$C_8$alkyl, $C_1$-$C_8$haloalkyl, $C_1$-$C_8$alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_1$-$C_8$alkylsulfonyl, $C_3$-$C_8$ cycloalkyl, $C_2$-$C_8$dialkylamino, $C_3$-$C_8$ alkenyloxy, $C_3$-$C_8$haloalkenyloxy, $C_3$-$C_8$alkynyloxy, $C_3$-$C_8$halo alkynyloxy, $C_1$-$C_8$alkylcarbonyloxy, $C_1$-$C_8$alkylcarbonylamino, $C_1$-$C_8$alkylsulfonyloxy, $C_1$-$C_8$ alkoxy$C_1$-$C_8$ alkoxy, $C_1$-$C_8$ alkoxycarbonyl$C_1$-$C_8$ alkoxy, or the following groups unsubstituted or substituted with 1-5 $R_{14}$: aryloxy, arylamino, arylmethoxy, arylmethylamino, heteroaryloxy or heteroarylamino, and when the number of the substitutes is more than 1, $R_{14}$ may be the same or different;

$R_9$ is selected from H, halogen, $NO_2$, CN, C(=O)$NR_{12}R_{13}$, C(=S)$NR_{12}R_{13}$, $C_1$-$C_8$alkylaminocarbonyl, $C_1$-$C_8$alkoxycarbonyl, $C_1$-$C_8$haloalkyl or $C_1$-$C_8$alkylsulfonyl;

$R_{10}$ is selected from H, halogen, OH, CN, $NO_2$, COOH, $C_1$-$C_8$alkyl, $C_1$-$C_8$haloalkyl, $C_1$-$C_8$alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_1$-$C_8$alkylsulfonyl, $C_2$-$C_8$dialkylamino, $C_3$-$C_8$alkenyloxy, $C_3$-$C_8$haloalkenyloxy, $C_3$-$C_8$ alkynyloxy, $C_3$-$C_8$halo alkynyloxy, $C_1$-$C_8$alkylcarbonyloxy, $C_1$-$C_8$alkylcarbonylamino, $C_1$-$C_8$alkylsulfonyloxy, $C_1$-$C_8$alkoxy$C_1$-$C_8$ alkoxy or $C_1$-$C_8$ alkoxycarbonyl$C_1$-$C_8$alkoxy;

$R_{11}$ is selected from CN or $NO_2$, $R_{12}$ and $R_{13}$ may be the same or different, respectively selected from H, $C_1$-$C_6$alkyl or $C_3$-$C_6$cycloalkyl;

$R_{14}$ is selected from halogen, $NO_2$, CN, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylcarbonyl, $C_1$-$C_6$alkoxycarbonyl, $C_2$-$C_6$alkenyl, $C_2$-$C_6$haloalkenyl, $C_3$-$C_6$alkenyloxy, $C_3$-$C_6$haloalkenyloxy, $C_2$-$C_6$alkynyl, $C_2$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$haloalkylamino, $C_2$-$C_8$dialkylamino, $C_1$-$C_6$alkylcarbonylamino, $C_1$-$C_6$haloalkylcarbonylamino, $C_1$-$C_6$alkylaminocarbonyl or $C_1$-$C_6$haloalkylaminocarbonyl;

Or the salts of the compounds having general formula I.

Furthermore, the preferred uses as antitumor compounds of general formula I of this invention include two kinds of compounds:

The first kind of compound is: $R_7$ is Cl, $R_9$ and $R_{11}$ are CN in compounds of general formula I, the structures are as general formula II:

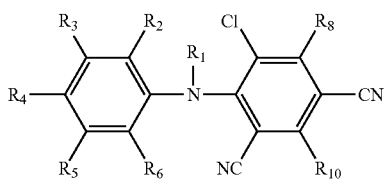

II

Wherein:

$R_1$ is selected from H, $C_1$-$C_8$alkyl, $C_3$-$C_8$cycloalkyl, $C_1$-$C_8$haloalkyl, $C_1$-$C_8$alkylcarbonyl, $C_1$-$C_8$halo alkylcarbonyl, $C_1$-$C_8$alkoxycarbonyl, $C_1$-$C_8$alkylamino carbonyl, $C_1$-$C_8$alkylsulfonyl, $C_1$-$C_8$alkoxy$C_1$-$C_8$alkyl, $C_1$-$C_8$ alkoxy$C_1$-$C_8$alkylcarbonyl, $C_1$-$C_8$ alkoxycarbonyl$C_1$-$C_8$alkyl, $C_2$-$C_8$alkenyl, $C_2$-$C_8$alkynyl, $C_2$-$C_8$haloalkenyl, $C_2$-$C_8$haloalkynyl, aryl $C_1$-$C_8$alkyl or CO—X—$CO_2R_{12}$, in which X is selected from $(CHR_{12})n$, $CR_{12}$=$CR_{13}$ or $C_6H_4$, n=1-6;

$R_2$ and $R_6$ may be the same or different, respectively selected from H, halogen, CN, $NO_2$, COOH, C(=O)$NR_{12}R_{13}$, $C_1$-$C_8$alkyl, $C_1$-$C_8$halo alkyl, $C_1$-$C_8$alkoxy, $C_1$-$C_8$halo alkoxy, $C_1$-$C_8$alkylthio, $C_1$-$C_8$halo alkylthio, $C_2$-$C_8$ alkenyl, $C_2$-$C_8$ alkynyl, $C_1$-$C_8$alkylsulfonyl, $C_1$-$C_8$alkylcarbonyl, $C_1$-$C_8$alkoxycarbonyl, $C_1$-$C_8$ alkoxy$C_1$-$C_8$alkyl, $C_1$-$C_8$ alkoxycarbonyl$C_1$-$C_8$alkyl, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_3$ and $R_5$ may be the same or different, respectively selected from H, halogen, CN, $NO_2$, COOH, C(=O)$NR_{12}R_{13}$, $C_1$-$C_8$alkyl, $C_1$-$C_8$halo alkyl, $C_1$-$C_8$ alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_2$-$C_8$alkenyl, $C_2$-$C_8$alkynyl, $C_1$-$C_8$alkylsulfonyl, $C_1$-$C_8$alkylcarbonyl, $C_1$-$C_8$ alkoxycarbonyl, $C_1$-$C_8$ alkoxy$C_1$-$C_8$alkyl, $C_1$-$C_8$alkoxycarbonyl$C_1$-$C_8$alkyl, $C_1$-$C_8$alkylcarbonyloxy, $C_1$-$C_8$ alkoxycarbonyloxy, $C_1$-$C_8$alkylaminocarbonyloxy, $C_1$-$C_8$alkylsulfonyloxy, $C_1$-$C_8$ alkoxy$C_1$-$C_8$ alkoxy, $C_1$-$C_8$haloalkoxy$C_1$-$C_8$haloalkoxy, $C_1$-$C_8$ alkoxycarbonyl$C_1$-$C_8$ alkoxy, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_4$ is selected from H, halogen, CN, $NO_2$, COOH, $CO_2Na$, $CO_2NH_4$, C(=O)$NR_{12}R_{13}$, $C_1$-$C_8$alkyl, $C_1$-$C_8$halo alkyl, $C_1$-$C_8$alkoxy, $C_1$-$C_8$halo alkoxy, $C_2$-$C_8$ alkenyl, $C_2$-$C_8$ alkynyl, $C_1$-$C_8$alkylsulfonyl, $C_1$-$C_8$alkylcarbonyl, $C_1$-$C_8$ alkoxycarbonyl, $C_1$-$C_8$alkoxy$C_1$-$C_8$alkyl, $C_1$-$C_8$ alkoxycarbonyl$C_1$-$C_8$alkyl, $C_1$-$C_8$alkoxy$C_1$-$C_8$ alkoxy, $C_1$-$C_8$haloalkoxy$C_1$-$C_8$haloalkoxy, $SO_2NR_{12}R_{13}$, or the following groups unsubstituted or substituted with 1-5 $R_{14}$: aryl, arylmethyl, arylcarbonyl, arylmethylcarbonyl, aryloxycarbonyl or arylaminocarbonyl, and when the number of the substitutes is more than 1, $R_{14}$ may be the same or different;

$R_8$ and $R_{10}$ may be the same or different, respectively selected from H, halogen, OH, CN, $NO_2$, COOH, $C_1$-$C_8$alkyl, $C_1$-$C_8$haloalkyl, $C_1$-$C_8$alkoxy, $C_1$-$C_8$haloalkoxy, $C_1$-$C_8$alkylamino, $C_1$-$C_8$haloalkylamino, $C_1$-$C_8$alkylthio, $C_1$-$C_8$haloalkylthio, $C_1$-$C_8$alkylsulfonyl, $C_2$-$C_8$dialkylamino, $C_3$-$C_8$alkenyloxy, $C_3$-$C_8$haloalkenyloxy, $C_3$-$C_8$ alkynyloxy, $C_3$-$C_8$haloalkynyloxy, $C_1$-$C_8$alkylcarbonyloxy, $C_1$-$C_8$alkylcarbonylamino, $C_1$-$C_8$alkylsulfonyloxy, $C_1$-$C_8$ alkoxy$C_1$-$C_8$ alkoxy or $C_1$-$C_8$alkoxycarbonyl$C_1$-$C_8$ alkoxy;

$R_{12}$ and $R_{13}$ may be the same or different, respectively selected from H, $C_1$-$C_6$alkyl or $C_3$-$C_6$cycloalkyl;

$R_{14}$ is selected from halogen, $NO_2$, CN, $C_1$-$C_6$alkyl, $C_1$-$C_6$haloalkyl, $C_1$-$C_6$alkoxy, $C_1$-$C_6$halo alkoxy, $C_1$-$C_6$alkylthio, $C_1$-$C_6$alkylcarbonyl, $C_1$-$C_6$ alkoxycarbonyl, $C_2$-$C_6$alkenyl, $C_2$-$C_6$haloalkenyl, $C_3$-$C_6$alkenyloxy, $C_3$-$C_6$haloalkenyloxy, $C_2$-$C_6$alkynyl, $C_2$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$halo alkylamino, $C_2$-$C_8$dialkylamino, $C_1$-$C_6$alkylcarbonylamino, $C_1$-$C_6$halo alkylcarbonylamino, $C_1$-$C_6$alkylamino carbonyl or $C_1$-$C_6$halo alkylamino carbonyl;

Or the salts of the compounds having general formula II.

The preferred uses as antitumor compounds of general formula II of this invention are:

$R_1$ is selected from H, $C_1$-$C_4$alkyl, $C_3$-$C_6$cycloalkyl, $C_1$-$C_4$haloalkyl, $C_1$-$C_4$alkylcarbonyl, $C_1$-$C_4$halo alkylcarbonyl, $C_1$-$C_4$ alkoxycarbonyl, $C_1$-$C_4$alkylsulfonyl, $C_1$-$C_4$ alkoxy$C_1$-$C_4$alkyl, $C_1$-$C_4$alkoxy$C_1$-$C_4$alkylcarbonyl, $C_1$-$C_4$alkoxycarbonyl$C_1$-$C_4$alkyl, $C_2$-$C_4$alkenyl, $C_2$-$C_4$alkynyl, $C_2$-$C_4$haloalkenyl, $C_2$-$C_4$haloalkynyl, benzyl, phenethyl or CO—X—$CO_2R_{12}$, in which X is selected from $(CHR_{12})n$, $CR_{12}$=$CR_{13}$ or $C_6H_4$, n=1-3;

$R_2$ and $R_6$ may be the same or different, respectively selected from H, Cl, Br, F, CN, $NO_2$, COOH, C(=O)$NR_{12}R_{13}$, $C_1$-$C_4$alkyl, $C_1$-$C_4$halo alkyl, $C_1$-$C_4$alkoxy, $C_1$-$C_4$halo alkoxy, $C_1$-$C_4$alkylthio, $C_1$-$C_4$halo alkylthio, $C_2$-$C_4$ alkenyl, $C_2$-$C_4$alkynyl, $C_1$-$C_4$alkylsulfonyl, $C_1$-$C_4$alkylcarbonyl, $C_1$-$C_4$alkoxycarbonyl, $C_1$-$C_4$alkoxy$C_1$-$C_4$alkyl, $C_1$-$C_4$alkoxycarbonyl$C_1$-$C_4$alkyl, or the following groups unsubstituted or substituted with 1-3 $R_{14}$: phenoxy, phenylamino, phenylcarbonyl, benzylcarbonyl, phenoxycarbonyl, phenylaminocarbonyl or pyridyloxy, and when the number of the substitutes is more than 1, $R_{14}$ may be the same or different;

$R_3$ and $R_5$ may be the same or different, respectively selected from H, Cl, Br, F, CN, $NO_2$, COOH, C(=O)$NR_{12}R_{13}$, $C_1$-$C_4$alkyl, $C_1$-$C_4$haloalkyl, $C_1$-$C_4$alkoxy, $C_1$-$C_4$haloalkoxy, $C_1$-$C_4$alkylamino, $C_1$-$C_4$halo alkylamino, $C_1$-$C_4$alkylthio, $C_1$-$C_4$haloalkylthio, $C_2$-$C_4$alkenyl, $C_2$-$C_4$alkynyl, $C_1$-$C_4$alkylsulfonyl, $C_1$-$C_4$alkylcarbonyl, $C_1$-$C_4$ alkoxycarbonyl, $C_1$-$C_4$ alkoxy$C_1$-$C_4$alkyl, $C_1$-$C_4$alkoxycarbonyl$C_1$-$C_4$alkyl, or the following groups unsubstituted or substituted with 1-3 $R_{14}$: phenoxy, phenylamino, phenylcarbonyl, benzylcarbonyl, phenoxycarbonyl, phenylaminocarbonyl or pyridyloxy, and when the number of the substitutes is more than 1, $R_{14}$ may be the same or different;

$R_4$ is selected from H, Cl, Br, F, CN, $NO_2$, COOH, $CO_2Na$, $CO_2NH_4$, C(=O)$NR_{12}R_{13}$, $C_1$-$C_4$alkyl, $C_1$-$C_4$haloalkyl, $C_1$-$C_4$alkoxy, $C_1$-$C_4$haloalkoxy, $C_2$-$C_4$alkenyl, $C_2$-$C_4$alkynyl, $C_1$-$C_4$alkylsulfonyl, $C_1$-$C_4$alkylcarbonyl, $C_1$-$C_4$ alkoxycarbonyl, $C_1$-$C_4$alkoxy$C_1$-$C_4$alkyl, $C_1$-$C_4$ alkoxycarbonyl$C_1$-$C_4$alkyl, $C_1$-$C_4$alkoxy$C_1$-$C_4$alkoxy, $SO_2NHCH_3$, $SO_2N(CH_3)_2$, or the following groups unsubstituted or substituted with 1-3 $R_{14}$: phenylcarbonyl, benzylcarbonyl, phenoxycarbonyl or phenylaminocarbonyl, and when the number of the substituents is more than 1, $R_{14}$ may be the same or different;

$R_8$ and $R_{10}$ may be the same or different, respectively selected from Cl, Br, F, OH, CN, $NO_2$, $C_1$-$C_4$alkyl, $C_1$-$C_4$halo alkyl, $C_1$-$C_4$ alkoxy, $C_1$-$C_4$halo alkoxy, $C_1$-$C_4$alkylamino, $C_1$-$C_4$halo alkylamino, $C_1$-$C_4$alkylthio, $C_1$-$C_4$halo alkylthio, $C_1$-$C_4$alkylsulfonyl, $C_2$-$C_6$dialkylamino, $C_3$-$C_4$ alkenyloxy, $C_3$-$C_4$haloalkenyloxy, $C_3$-$C_4$alkynyloxy, $C_3$-$C_4$haloalkynyloxy, $C_1$-$C_4$alkylcarbonyloxy, $C_1$-$C_4$alkylcarbonylamino, $C_1$-$C_4$alkylsulfonyloxy, $C_1$-$C_4$alkoxy$C_1$-$C_4$alkoxy or $C_1$-$C_4$alkoxycarbonyl$C_1$-$C_4$ alkoxy;

$R_{12}$ and $R_{13}$ may be the same or different, respectively selected from H or $C_1$-$C_4$alkyl; $R_{14}$ is selected from F, Cl, Br, $NO_2$, CN, $C_1$-$C_4$alkyl, $C_1$-$C_4$haloalkyl, $C_1$-$C_4$alkoxy, $C_1$-$C_4$halo alkoxy, $C_1$-$C_4$alkylthio, $C_1$-$C_4$alkylcarbonyl, $C_1$-$C_4$ alkoxycarbonyl or $C_1$-$C_4$alkylaminocarbonyl;

Or the salts of the compounds having general formula II.

Furthermore, the preferred uses as antitumor compounds of general formula II of this invention are:

$R_1$ is selected from H, $CH_3$, acetyl, methylsulfonyl, benzyl or phenethyl;

$R_2$ and $R_6$ may be the same or different, respectively selected from H, F, Cl, Br, CN, $NO_2$, COOH, $CONH_2$, $CONHCH_3$, $CON(CH_3)_2$, $CONHCH(CH_3)_2$, $CONHC(CH_3)_3$, $CH_3$, $C_2H_5$, $CH(CH_3)_2$, $C(CH_3)_3$, $ClCH_2$, $CF_3$, $CH_3O$, $C_2H_5O$, $CF_3O$, $CF_3CH_2O$, $CH_3S$, $CH_3OCO$ or $CH_3OCH_2$;

$R_3$ and $R_5$ may be the same or different, respectively selected from H, F, Cl, Br, CN, $NO_2$, COOH, $CONH_2$, $CONHCH_3$, $CON(CH_3)_2$, $CONHCH(CH_3)_2$, $CONHC(CH_3)_3$, $CH_3$, $C_2H_5$, $CH(CH_3)_2$, $C(CH_3)_3$, $ClCH_2$, $CF_3$, $CH_3O$, $C_2H_5O$, $CF_3O$, $CF_3CH_2O$, $CH_3S$, $CH_3OCO$ or $CH_3OCH_2$;

$R_4$ is selected from H, F, Cl, Br, CN, $NO_2$, COOH, $CO_2Na$, $CO_2NH_4$, $CONH_2$, $CONHCH_3$, $CON(CH_3)_2$, $CONHCH(CH_3)_2$, $CONHC(CH_3)_3$, $CF_3$, $CF_3O$, $CH_3OCO$, $C_2H_5OCO$, $CH_3SO_2$, $SO_2NHCH_3$, $SO_2N(CH_3)_2$, phenoxycarbonyl, phenylaminocarbonyl, 4-$CH_3$-phenylaminocarbonyl or 4-Cl-phenylaminocarbonyl;

$R_8$ and $R_{10}$ may be the same or different, respectively selected from Cl, F, $CH_3O$, $CF_3O$, $CF_3CH_2O$, $CH_3NH$, $(CH_3)_2N$, $(C_2H_5)_2N$, $CF_3CH_2NH$, $ClCH_2CH_2NH$, $CH_3S$, $C_2H_5S$, $CH_3SO_2$, $C_2H_5SO_2$, $(CH_3)_2N$, $CH_2$=$CHCH_2O$, C≡$CCH_2O$, ClC≡$CCH_2O$, IC≡$CCH_2O$, $CH_3CO_2$, $CH_3CONH$, $CH_3OCH_2CH_2O$, $C_2H_5OCH_2CH_2O$, $CH_3OC$(=O)$CH_2O$ or $CH_3OC$(=O)$CH_2CH_2O$;

Or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

Even more preferred uses as antitumor compounds of general formula II of this invention are:

$R_1$ is selected from H;
$R_2$ is selected from H, F, Cl, Br, $CH_3$, $C_2H_5$, $NO_2$ or CN;
$R_3$ is selected from H, F, Cl, Br, $CH_3$ or $CF_3$;
$R_4$ is selected from H, F, Cl, Br, $CF_3$, $CF_3O$, $CH_3OCO$, CN, $NO_2$, COOH, $CO_2Na$, phenylaminocarbonyl or 4-Cl-phenylaminocarbonyl;
$R_5$ is selected from H, Cl, Br, $CH_3$ or $CF_3$;
$R_6$ is selected from H, F, Cl, Br, $CH_3$, $C_2H_5$, $NO_2$ or CN;

$R_8$ is selected from Cl, $CH_3O$, $CH_3NH$, $(CH_3)_2N$ or $(C_2H_5)_2N$;

$R_{10}$ is selected from Cl, $CH_3O$ or $CH_3NH$;

Or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

The more preferred uses as antitumor compounds of general formula II of this invention are:

$R_1$, $R_3$ and $R_5$ are selected from H;
$R_2$ and $R_6$ are selected from H, Cl or Br;
$R_4$ is selected from H, Cl, Br, $NO_2$, $CF_3$, $CF_3O$ or $CH_3OCO$;
$R_8$ and $R_{10}$ are selected from Cl;

Or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

The most preferred uses as antitumor compounds of general formula II of this invention are:

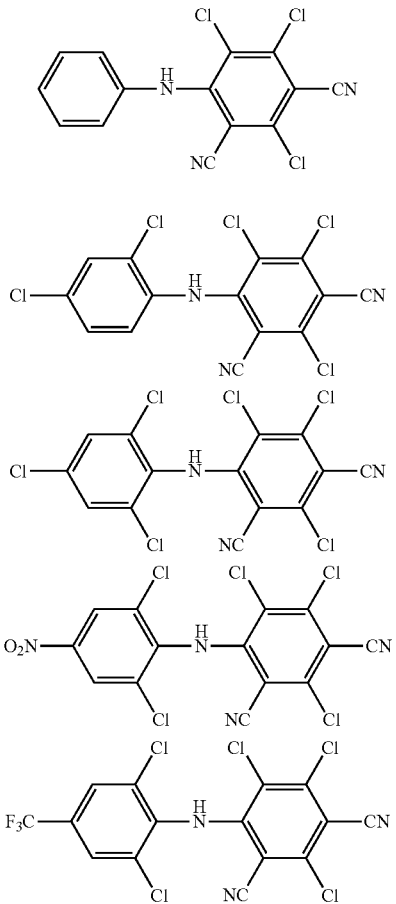

-continued

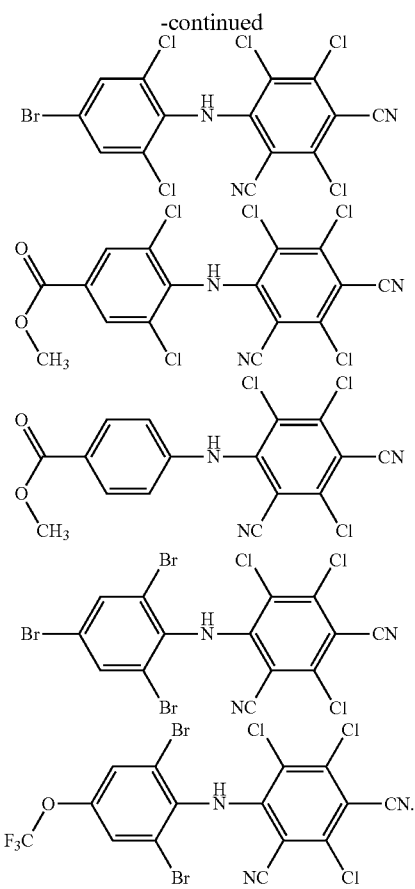

The following structure in the most preferred uses as antitumor compounds of general formula II of this invention has never been reported before (refer to compound Table 6-112):

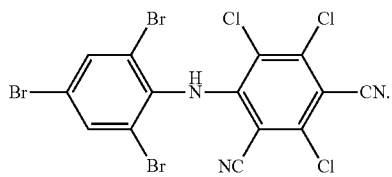

The second kind of compound of the preferred uses as antitumor compounds of general formula I of this invention is: $R_7$ is $CH_3$, $R_{10}$ is H, $R_{11}$ is $NO_2$, the structures are as general formula III:

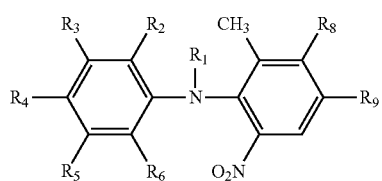

Wherein:

$R_1$ is selected from H, $C_1$-$C_8$alkyl, $C_3$-$C_8$cycloalkyl, $C_1$-$C_8$haloalkyl, $C_1$-$C_8$alkylcarbonyl, $C_1$-$C_8$halo alkylcarbonyl, $C_1$-$C_8$ alkoxycarbonyl, $C_1$-$C_8$alkylamino carbonyl, $C_1$-$C_8$alkylthio, $C_1$-$C_8$halo alkylthio, $C_1$-$C_8$alkylsulfonyl, $C_1$-$C_8$ alkoxy$C_1$-$C_8$alkyl, $C_1$-$C_8$ alkoxy$C_1$-$C_8$alkylcarbonyl, $C_1$-$C_8$alkoxycarbonyl$C_1$-$C_8$alkyl, $C_1$-$C_8$alkylaminothio, $C_2$-$C_8$dialkylaminothio or CO—X—$CO_2R_{12}$, in which X is selected from $(CHR_{12})n$, $CR_{12}$=$CR_{13}$ or $C_6H_4$, n=1-6;

$R_2$ and $R_6$ may be the same or different, respectively selected from H, halogen, CN, $NO_2$, C(=O)$NR_{12}R_{13}$, $C_1$-$C_8$alkyl, $C_1$-$C_8$haloalkyl, $C_1$-$C_8$alkoxy, $C_1$-$C_8$haloalkoxy, $C_2$-$C_8$alkenyl, $C_2$-$C_8$alkynyl, $C_1$-$C_8$alkylsulfonyl, $C_1$-$C_8$alkylcarbonyl, $C_1$-$C_8$alkoxycarbonyl, $C_1$-$C_8$alkoxy$C_1$-$C_8$alkyl, $C_1$-$C_8$alkoxycarbonyl$C_1$-$C_8$alkyl, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_3$ and $R_5$ may be the same or different, respectively selected from H, halogen, CN, $NO_2$, C(=O)$NR_{12}R_{13}$, $C_1$-$C_8$alkyl, $C_1$-$C_8$halo alkyl, $C_1$-$C_8$ alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_2$-$C_8$alkenyl, $C_2$-$C_8$alkynyl, $C_1$-$C_8$alkylsulfonyl, $C_1$-$C_8$alkylcarbonyl, $C_1$-$C_8$ alkoxycarbonyl, $C_1$-$C_8$ alkoxy$C_1$-$C_8$alkyl, $C_1$-$C_8$alkoxycarbonyl$C_1$-$C_8$alkyl, $C_1$-$C_8$alkylcarbonyloxy, $C_1$-$C_8$alkoxycarbonyloxy, $C_1$-$C_8$alkylaminocarbonyloxy, $C_1$-$C_8$alkylsulfonyloxy, $C_1$-$C_8$alkoxy$C_1$-$C_8$alkoxy, $C_1$-$C_8$halo alkoxy$C_1$-$C_8$halo alkoxy, $C_1$-$C_8$ alkoxycarbonyl$C_1$-$C_8$ alkoxy, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_4$ is selected from H, halogen, CN, $NO_2$, COOH, C(=O)$NR_{12}R_{13}$, $C_1$-$C_8$alkyl, $C_1$-$C_8$haloalkyl, $C_1$-$C_8$alkoxy, $C_1$-$C_8$halo alkoxy, $C_2$-$C_8$alkenyl, $C_2$-$C_8$ alkynyl, $C_1$-$C_8$alkylsulfonyl, $C_1$-$C_8$alkylcarbonyl, $C_1$-$C_8$alkoxycarbonyl, $C_1$-$C_8$ alkoxy$C_1$-$C_8$alkyl, $C_1$-$C_8$ alkoxycarbonyl$C_1$-$C_8$alkyl, $C_1$-$C_8$alkoxy$C_1$-$C_8$ alkoxy, $C_1$-$C_8$haloalkoxy$C_1$-$C_8$haloalkoxy, or the following groups unsubstituted or substituted with 1-5 $R_{14}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{14}$ may be the same or different;

$R_8$ is selected from H, halogen, $C_1$-$C_8$halo alkyl, $C_1$-$C_8$ alkoxy, $C_1$-$C_8$halo alkoxy, $C_1$-$C_8$alkylamino, $C_1$-$C_8$halo alkylamino, $C_1$-$C_8$alkylthio, $C_1$-$C_8$halo alkylthio, $C_1$-$C_8$alkylsulfonyl, $C_3$-$C_8$ cyclo alkyl, $C_2$-$C_8$dialkylamino, $C_3$-$C_8$ alkenyloxy, $C_3$-$C_8$haloalkenyloxy, $C_3$-$C_8$alkynyloxy, $C_3$-$C_8$haloalkynyloxy, $C_1$-$C_8$alkylcarbonyloxy, $C_1$-$C_8$alkylcarbonylamino, $C_1$-$C_8$alkylsulfonyloxy, $C_1$-$C_8$ alkoxy$C_1$-$C_8$ alkoxy, $C_1$-$C_8$alkoxycarbonyl$C_1$-$C_8$alkoxy, or the following groups unsubstituted or substituted with 1-5 $R_{14}$: aryloxy, arylamino, arylmethoxy, arylmethylamino, heteroaryloxy or heteroarylamino, and when the number of the substitutes is more than 1, $R_{14}$ may be the same or different;

$R_9$ is selected from H, halogen, $NO_2$, CN, C(=O)$NR_{12}R_{13}$, C(=S)$NR_{12}R_{13}$, $C_1$-$C_8$alkylamino carbonyl, $C_1$-$C_8$ alkoxycarbonyl, $C_1$-$C_8$halo alkyl or $C_1$-$C_8$alkylsulfonyl;

$R_{12}$ and $R_{13}$ may be the same or different, respectively selected from H or $C_1$-$C_6$alkyl;

$R_{14}$ is selected from halogen, $NO_2$, CN, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylcarbonyl, $C_1$-$C_6$alkoxycarbonyl, $C_2$-$C_6$alkenyl, $C_2$-$C_6$haloalkenyl, $C_3$-$C_6$alkenyloxy, $C_3$-$C_6$haloalkenyloxy, $C_2$-$C_6$alkynyl, $C_2$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$halo alkylamino, $C_2$-$C_8$dialkylamino, $C_1$-$C_6$alkylcarbonylamino, $C_1$-$C_6$halo alkylcarbonylamino, $C_1$-$C_6$alkylaminocarbonyl or $C_1$-$C_6$haloalkylaminocarbonyl;

Or the salts of the compounds having general formula III.

The preferred uses as antitumor compounds of general formula III of this invention are:

$R_1$ is selected from H, $C_1$-$C_4$alkyl, $C_3$-$C_6$cycloalkyl, $C_1$-$C_4$alkylcarbonyl, $C_1$-$C_4$haloalkylcarbonyl, $C_1$-$C_4$alkoxycarbonyl, $C_1$-$C_4$alkylthio, $C_1$-$C_4$halo alkylthio, $C_1$-$C_4$alkylsulfonyl, $C_1$-$C_4$ alkoxy$C_1$-$C_4$alkyl, $C_1$-$C_4$alkoxy$C_1$-$C_4$alkylcarbonyl, $C_1$-$C_4$ alkoxycarbonyl$C_1$-$C_4$alkyl, $C_1$-$C_4$alkylaminothio, $C_2$-$C_4$dialkylaminothio or CO—X—$CO_2R_{12}$, in which X is selected from $(CHR_{12})n$, $CR_{12}$=$CR_{13}$ or $C_6H_4$, n=1-3;

$R_2$ and $R_6$ may be the same or different, respectively selected from H, halogen, CN, $NO_2$, C(=O)$NR_{12}R_{13}$, $C_1$-$C_4$alkyl, $C_1$-$C_4$haloalkyl, $C_1$-$C_4$alkoxy, $C_1$-$C_4$haloalkoxy, $C_2$-$C_6$alkenyl, $C_2$-$C_6$alkynyl, $C_1$-$C_4$alkylsulfonyl, $C_1$-$C_4$alkylcarbonyl, $C_1$-$C_4$alkoxycarbonyl, $C_1$-$C_4$alkoxy$C_1$-$C_4$alkyl, $C_1$-$C_4$alkoxycarbonyl$C_1$-$C_4$alkyl, or the following groups unsubstituted or substituted with 1-4 $R_{14}$: phenoxy, phenylamino, phenylcarbonyl, benzylcarbonyl, phenoxycarbonyl, phenylaminocarbonyl or pyridyloxy, and when the number of the substitutes is more than 1, $R_{14}$ may be the same or different;

$R_3$ and $R_5$ may be the same or different, respectively selected from H, halogen, CN, $NO_2$, C(=O)$NR_{12}R_{13}$, $C_1$-$C_4$alkyl, $C_1$-$C_4$halo alkyl, $C_1$-$C_4$ alkoxy, $C_1$-$C_4$haloalkoxy, $C_1$-$C_4$alkylamino, $C_1$-$C_4$haloalkylamino, $C_1$-$C_4$alkylthio, $C_1$-$C_4$halo alkylthio, $C_2$-$C_6$alkenyl, $C_2$-$C_6$alkynyl, $C_1$-$C_4$alkylsulfonyl, $C_1$-$C_4$alkylcarbonyl, $C_1$-$C_4$alkoxycarbonyl or $C_1$-$C_4$ alkoxy$C_1$-$C_4$alkyl;

$R_4$ is selected from H, halogen, CN, $NO_2$, COOH, C(=O)$NR_{12}R_{13}$, $C_1$-$C_4$alkyl, $C_1$-$C_4$haloalkyl, $C_1$-$C_4$halo alkoxy, $C_2$-$C_6$alkenyl, $C_2$-$C_6$ alkynyl, $C_1$-$C_4$alkylsulfonyl, $C_1$-$C_4$alkylcarbonyl, $C_1$-$C_4$alkoxycarbonyl, $C_1$-$C_4$ alkoxy$C_1$-$C_4$alkyl, $C_1$-$C_4$ alkoxycarbonyl$C_1$-$C_4$alkyl, $C_1$-$C_4$alkoxy$C_1$-$C_4$alkoxy, or the following groups unsubstituted or substituted with 1-4 $R_{14}$: phenoxy, phenylamino, phenylcarbonyl, benzylcarbonyl, phenoxycarbonyl, phenylaminocarbonyl or pyridyloxy, and when the number of the substitutes is more than 1, $R_{14}$ may be the same or different;

$R_8$ is selected from H, halogen, $C_1$-$C_4$alkoxy, $C_1$-$C_4$haloalkoxy, $C_1$-$C_4$alkylamino, $C_1$-$C_4$haloalkylamino, $C_1$-$C_4$alkylthio, $C_1$-$C_4$haloalkylthio, $C_1$-$C_4$alkylsulfonyl, $C_2$-$C_4$dialkylamino, $C_3$-$C_4$alkenyloxy, $C_3$-$C_4$haloalkenyloxy, $C_3$-$C_6$alkynyloxy, $C_1$-$C_4$alkylcarbonyloxy, $C_1$-$C_4$alkylcarbonylamino, $C_1$-$C_4$alkylsulfonyloxy, $C_1$-$C_4$ alkoxy$C_1$-$C_4$alkoxy, $C_1$-$C_4$alkoxycarbonyl$C_1$-$C_4$alkoxy, or the following groups unsubstituted or substituted with 1-3 $R_{14}$: phenoxy, phenylamino, benzyloxy, benzylamino, pyridyloxy or pyridylamino, and when the number of the substitutes is more than 1, $R_{14}$ may be the same or different;

$R_9$ is selected from Cl, Br, F, $NO_2$, CN, C(=O)$NR_{12}R_{13}$, C(=S)$NR_{12}R_{13}$, $CO_2CH_3$, $CF_3$ or $CH_3SO_2$;

$R_{12}$ and $R_{13}$ may be the same or different, respectively selected from H or $C_1$-$C_3$alkyl;

$R_{14}$ is selected from halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylcarbonyl, $C_1$-$C_3$ alkoxycarbonyl, $C_1$-$C_3$alkylamino, $C_2$-$C_4$dialkylamino, $C_1$-$C_3$alkylcarbonylamino or $C_1$-$C_3$alkylaminocarbonyl;

Or the salts of the compounds having general formula III.

Furthermore, the preferred uses as antitumor compounds of general formula III of this invention are:

$R_1$ is selected from H, $CH_3$, $C_2H_5$, cyclopropyl, formyl, acetyl, $COCF_3$, $CO_2CH_3$, $CO_2C_2H_5$, $SCCl_3$, $SO_2CH_3$, $SO_2C_2H_5$, $CH_2OCH_3$, $CH_2OC_2H_5$, $CH_2CH_2OCH_3$, $COCH_2OCH_3$, $CH_2COOCH_3$, $SNHCH_3$, $SN(CH_3)_2$, $COCH_2CO_2H$, $COCH_2CO_2CH_3$, $COCH_2CH_2CO_2H$, $COCH_2CH_2CO_2CH_3$, $COCHCH_3CO_2H$, $COCHCH_3CO_2CH_3$, $COC_6H_4CO_2H$, $COC_6H_4CO_2CH_3$, COCH=$CHCO_2H$ or COCH=$CHCO_2CH_3$;

$R_2$ and $R_6$ may be the same or different, respectively selected from H, Cl, Br, F, CN, $NO_2$, C(=O)$NH_2$, C(=O)$NHCH_3$, C(=O)$N(CH_3)_2$, $CH_3$, $C_2H_5$, $CF_3$, $OCH_3$, $OC_2H_5$, $OCF_3$, $SO_2CH_3$, $SO_2C_2H_5$, $COCH_3$, $CO_2CH_3$, $CO_2C_2H_5$, phenoxy, phenylamino, phenoxycarbonyl or phenylaminocarbonyl;

$R_3$ and $R_5$ may be the same or different, respectively selected from H, Cl, Br, F, CN, $NO_2$, C(=O)$NH_2$, $CH_3$, $CF_3$, $OCH_3$, $OCF_3$, $NHCH_3$, $SCH_3$, $SO_2CH_3$, $SO_2C_2H_5$, $COCH_3$, $CO_2CH_3$, $CO_2C_2H_5$ or $CH_2OCH_3$;

$R_4$ is selected from H, Cl, Br, F, CN, $NO_2$, $CO_2H$, C(=O)$NH_2$, C(=O)$NHCH_3$, C(=O)$N(CH_3)_2$, $CH_3$, $CF_3$, $CF(CF_3)_2$, $OCF_3$, $OCH_2CF_3$, $OCF_2CHFCF_3$, $SO_2CH_3$, $SO_2C_2H_5$, $COCH_3$, $CO_2CH_3$, $CO_2C_2H_5$, phenoxy, phenylamino, phenylcarbonyl, benzylcarbonyl, phenoxycarbonyl, phenylaminocarbonyl, pyridyloxy or 3-chloro-5-(trifluoromethyl)pyridin-2-yloxy;

$R_8$ is selected from H, Cl, Br, F, $C_1$-$C_3$ alkoxy, $C_1$-$C_3$ haloalkoxy, $C_1$-$C_3$alkylamino, $C_1$-$C_3$haloalkylamino, $SCH_3$, $SC_2H_5$, $N(CH_3)_2$, $N(C_2H_5)_2$, $OCH_2OCH_3$, phenoxy, phenylamino, benzyloxy, benzylamino, 4-chlorophenoxy, 4-chlorophenylamino, 2-chloro-4-(trifluoromethyl)phenoxy, 2-chloro-4-(trifluoromethyl)phenylamino, 3-chloro-5-(trifluoromethyl)pyridin-2-yloxy or 3-chloro-5-(trifluoromethyl)pyridin-2-ylamino;

$R_9$ is $NO_2$;

Or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

Even more preferred uses as antitumor compounds of general formula III of this invention are:

$R_1$ is selected from H or $CH_3$;

$R_2$ and $R_6$ may be the same or different, respectively selected from H, Cl, Br, F, CN, $NO_2$, C(=O)$NH_2$, C(=O)$NHCH_3$, C(=O)$N(CH_3)_2$, $CH_3$, $CF_3$, $CO_2CH_3$ or phenoxycarbonyl;

$R_3$ and $R_5$ may be the same or different, respectively selected from H, Cl, Br, F, CN, $NO_2$, $CH_3$, $CF_3$ or $OCH_3$;

$R_4$ is selected from H, Cl, Br, F, CN, $NO_2$, $CO_2H$, C(=O)$NH_2$, C(=O)$NHCH_3$, $CH_3$, $CF_3$, $OCF_2CHFCF_3$, $CO_2CH_3$ or 3-chloro-5-(trifluoromethyl)pyridin-2-yloxy;

$R_8$ is selected from H, Cl, $OCH_3$, $OCH_2CF_3$, $NHCH_3$, $SCH_3$ or $N(CH_3)_2$;

$R_9$ is $NO_2$;

Or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

The more preferred uses as antitumor compounds of general formula III of this invention are:

$R_1$, $R_3$ and $R_5$ are selected from H;

$R_2$ is selected from Cl or F;

$R_4$ is selected from H, Cl, CN, $NO_2$ or $CF_3$;

$R_6$ is selected from F, Cl, CN or $NO_2$;

$R_8$ is selected from H, Cl or $OCH_2CF_3$;

$R_9$ is $NO_2$,

Or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

The most preferred uses as antitumor compounds of general formula III of this invention are:

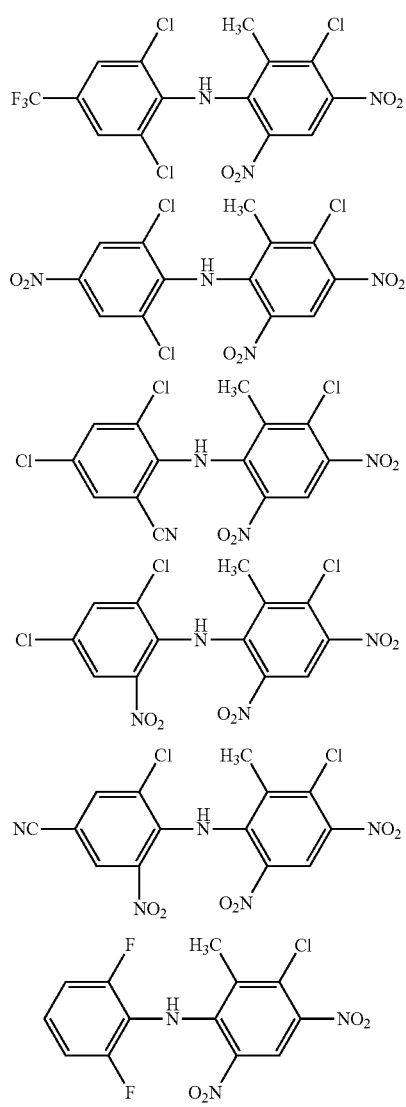

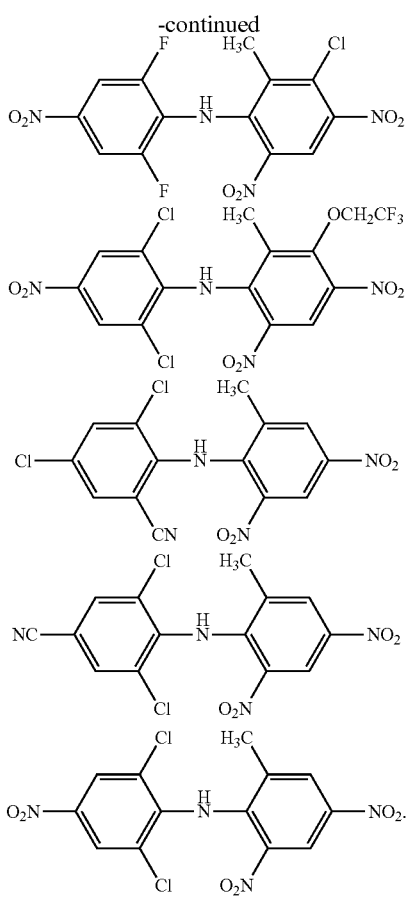

The terms used above to definite the compounds of general formula I represent substitutes as follow:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkoxy" refers to straight or branched chain alkyl, which is linked to the structure by oxygen atom.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "alkylthio" refers to straight or branched chain alkyl, which is linked to the structure by sulfur atom.

The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "alkylamino" refers to straight or branched chain alkyl, which is linked to the structure by nitrogen atom.

The "haloalkylamino" refers to straight or branched chain alkylamino, in which hydrogen atoms may be all or partly substituted with halogen.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl.

The "haloalkenyl" stands for straight or branched chain alkenyl, in which hydrogen atoms can be all or partly substituted with halogen.

The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl.

The "haloalkynyl" stands for straight or branched chain alkynyl, in which hydrogen atoms can be all or partly substituted with halogen.

The alkenyloxy refers to straight or branched chain alkenyl, which is linked to the structure by oxygen atom.

The alkynyloxy refers to straight or branched chain alkynyl, which is linked to the structure by oxygen atom.

The alkylsulfonyl refers to straight or branched chain alkyl, which is linked to the structure by sulfuryl($-SO_2-$), such as $SO_2CH_3$.

The alkylcarbonyl refers to straight or branched chain alkyl, which is linked to the structure by carbonyl($-CO-$), such as $CH_3CO-$, $CH_3CH_2CO-$.

The alkylcarbonyloxy: such as $CH_3COO-$, $CH_3CH_2NHCOO-$.

The alkylcarbonylamino: such as $CH_3CONH-$, $CH_3CH_2NHCONH-$.

The alkylsulfonyloxy: such as alkyl-$S(O)_2-O-$.

The alkoxycarbonyl: alkyl-$O-CO-$.

The phenylaminocarbonyl: phenyl-$NH-CO-$.

The aryl in aryl, arylmethyl, aryloxy, arylamino, arylcarbonyl, arylmethylcarbonyl, aryloxycarbonyl and arylaminocarbonyl refers to phenyl or naphthyl, etc.

The "heteroaryl" stands for five member ring or six member ring containing one or more N, O, S hetero atoms. Such as furanyl, pyrazolyl, thiazolyl, pyridinyl, pyrimidinyl, pyrazinyl, pyridazinyl, triazinyl, quinolinyl, etc.

Part of the substitutes of $R_1$, $R_2$, $R_3$, $R_4$, $R_5$, $R_6$, $R_8$ and $R_{10}$ in formula I are separately listed in table 1, table 2, table 3, table 4 and table 5, but without being restricted thereby.

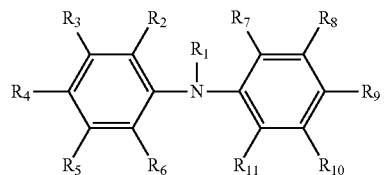

TABLE 1

| substitute $R_1$ | | |
|---|---|---|
| $R_1$ | $R_1$ | $R_1$ |
| H | $CO_2CH_3$ | $CH_2C\equiv C-Cl$ |
| $CH_3$ | $CO_2CH_2CH_3$ | $CH_2C\equiv CCH_3$ |
| $C_2H_5$ | $SO_2CH_2CH_3$ | $PhCH_2$ |
| $n$-$C_3H_7$ | $CH_2OCH_3$ | $PhCH_2CH_2$ |
| $i$-$C_3H_7$ | $CH_2CH_2OCH_3$ | $4$-$Cl-PhCH_2$ |
| $n$-$C_4H_9$ | $CH_2CH_2OCH_2CH_3$ | $COCH_2CO_2CH_3$ |
| $t$-$C_4H_9$ | $COCH_2OCH_3$ | $COCH_2CH_2CO_2CH_3$ |
| cyclopropylmethyl | $COCH_2OCH_2CH_3$ | $COCHCH_3CO_2CH_3$ |
| $CH_2Cl$ | $CH_2CO_2CH_3$ | $COCH_2COOH$ |
| $CF_3$ | $CH_2CO_2CH_2CH_3$ | $COCH_2CH_2COOH$ |
| $CH_2CF_3$ | $CH_2CH=CH_2$ | $COCHCH_3COOH$ |
| $COCH_3$ | $CH_2CH=CF_2$ | $COCH=CHCOOH$ |
| $COCH_2CH_3$ | $CH_2CH_2CH=CF_2$ | $COCH=CHCO_2CH_3$ |
| $COCH_2CH_2CH_3$ | $CH_2CH_2CF=CF_2$ | 2-carboxybenzoyl |
| $CONHCH_3$ | $CH_2CH=CCl_2$ | |
| $CONHCH_2CH_3$ | $CH_2C\equiv CH$ | 2-(methoxycarbonyl)benzoyl |
| $SO_2CH_3$ | $CH_2C\equiv C-I$ | |

TABLE 2

| substitute $R_2(R_6)$ | | | |
|---|---|---|---|
| $R_2(R_6)$ | $R_2(R_6)$ | $R_2(R_6)$ | $R_2(R_6)$ |
| H | $CH_3$ | $OCH(CH_3)_2$ | $CH_2CO_2CH_2CH_3$ |
| F | $CH_2CH_3$ | $OCF_3$ | Ph |
| Cl | $n$-$C_3H_7$ | $OCH_2CF_3$ | $CH_2Ph$ |
| Br | $i$-$C_3H_7$ | $OCF_2CF_3$ | OPh |
| I | $n$-$C_4H_9$ | $CH=CH_2$ | NHPh |
| CN | $t$-$C_4H_9$ | $CH_2CH=CH_2$ | COPh |
| $NO_2$ | $CF_3$ | $C\equiv CH$ | $CO_2Ph$ |
| COOH | $CHF_2$ | $CH_2C\equiv CH$ | $CO_2Ph$-4-Cl |
| $CONH_2$ | $CH_2F$ | $SO_2CH_3$ | $CO_2Ph$-2-Cl-4-$CF_3$ |
| $CONHCH_3$ | $CH_2Cl$ | $SO_2CH_2CH_3$ | $CO_2Ph$-2-Cl-4-$NO_2$ |
| $CON(CH_3)_2$ | $CH_2Br$ | $COCH_3$ | CONHPh |
| $CONHCH_2CH_3$ | $CH_2CF_3$ | $COCH_2CH_3$ | CONHPh-4-Cl |
| $CON(CH_2CH_3)_2$ | $CF_2CHF_2$ | $CO_2CH_3$ | CONHPh-2-Cl |
| $CONH(CH_2)_2CH_3$ | $CF_2CF_3$ | $CO_2CH_2CH_3$ | CONHPh-4-$NO_2$ |
| $CONHCH(CH_3)_2$ | $OCH_3$ | $CH_2OCH_3$ | CONHPh-2-Cl-4-$CF_3$ |
| $CONH(CH_2)_3CH_3$ | $OCH_2CH_3$ | $CH_2OCH_2CH_3$ | CONHPh-2-Cl-4-$NO_2$ |

TABLE 2-continued substitute R₂(R₆)

| $R_2(R_6)$ | $R_2(R_6)$ | $R_2(R_6)$ | $R_2(R_6)$ |
|---|---|---|---|
| $CONHC(CH_3)_3$ | $O(CH_2)_2CH_3$ | $CH_2CO_2CH_3$ | 3-Cl-5-CF₃-2-pyridyloxy |

TABLE 3 substitute R₃(R₅)

| $R_3(R_5)$ | $R_3(R_5)$ | $R_3(R_5)$ | $R_3(R_5)$ |
|---|---|---|---|
| H | n-C₃H₇ | OCH₂CF₃ | CH₂Ph |
| F | i-C₃H₇ | OCF₂CF₃ | OPh |
| Cl | n-C₄H₉ | CH=CH₂ | NHPh |
| Br | t-C₄H₉ | CH₂CH=CH₂ | COPh |
| I | CF₃ | C≡CH | CO₂Ph |
| CN | CHF₂ | CH₂C≡CH | CO₂Ph-4-Cl |
| NO₂ | CH₂F | SO₂CH₃ | CO₂Ph-2-Cl-4-CF₃ |
| COOH | CH₂Cl | SO₂CH₂CH₃ | CO₂Ph-2-Cl-4-NO₂ |
| CONH₂ | CH₂Br | COCH₃ | CONHPh |
| CONHCH₃ | CH₂CF₃ | COCH₂CH₃ | CONHPh-4-Cl |
| CON(CH₃)₂ | CF₂CHF₂ | CO₂CH₃ | CONHPh-2-Cl |
| CONHCH₂CH₃ | CF₂CF₃ | CO₂CH₂CH₃ | CONHPh-4-NO₂ |
| CON(CH₂CH₃)₂ | OCH₃ | CH₂OCH₃ | CONHPh-2-Cl-4-CF₃ |
| CONH(CH₂)₂CH₃ | OCH₂CH₃ | CH₂OCH₂CH₃ | CONHPh-2-Cl-4-NO₂ |
| CONHCH(CH₃)₂ | O(CH₂)₂CH₃ | CH₂CO₂CH₃ | 3-Cl-5-CF₃-2-pyridyloxy |
| CH₃ | OCH(CH₃)₂ | CH₂CO₂CH₂CH₃ | |
| CH₂CH₃ | OCF₃ | Ph | |

TABLE 4 substitute R₄

| $R_4$ | $R_4$ | $R_4$ | $R_4$ |
|---|---|---|---|
| H | CHF₂ | CH₂C≡CH | CONHCH(CH₃)₂ |
| F | CH₂F | SO₂CH₃ | CON(CH₂CH₃)₂ |
| Cl | CH₂Cl | SO₂CH₂CH₃ | CONHC(CH₃)₃ |
| Br | CH₂Br | COCH₃ | SO₂NH₂ |
| I | CH₂CF₃ | COCH₂CH₃ | SO₂NHCH₃ |
| CN | CF₂CHF₂ | CO₂CH₃ | SO₂N(CH₃)₂ |
| NO₂ | CF₂CF₃ | CO₂CH₂CH₃ | Ph |
| COOH | OCH₃ | CH₂OCH₃ | CH₂Ph |
| CO₂Na | OCH₂CH₃ | CH₂OCH₂CH₃ | COPh |
| CO₂NH₄ | O(CH₂)₂CH₃ | CH₂CO₂CH₃ | COCH₂Ph |
| CH₃ | OCH(CH₃)₂ | CH₂CO₂CH₂CH₃ | CO₂Ph |
| CH₂CH₃ | OCF₃ | OCH₂OCH₃ | CO₂Ph-2-Cl-4-CF₃ |
| n-C₃H₇ | OCH₂CF₃ | OCH₂OCH₂CH₃ | CONHPh |
| i-C₃H₇ | OCF₂CF₃ | CONH₂ | CONHPh-4-Cl |
| n-C₄H₉ | CH=CH₂ | CONHCH₃ | CONHPh-4-CH₃ |
| t-C₄H₉ | CH₂CH=CH₂ | CON(CH₃)₂ | CONHPh-2-Cl-4-NO₂ |
| CF₃ | C≡CH | CONH(CH₂)₂CH₃ | CONHPh-2-Cl-4-CF₃ |

TABLE 5 substitute R₈(R₁₀)

| $R_8(R_{10})$ | $R_8(R_{10})$ | $R_8(R_{10})$ | $R_8(R_{10})$ | $R_8(R_{10})$ |
|---|---|---|---|---|
| H | CH₃ | OCH₃ | SCH₃ | OCOCH₃ |
| F | C₂H₅ | OCH₂CH₃ | SCH₂CH₃ | OCOCH₂CH₃ |
| Cl | n-C₃H₇ | OCF₃ | SO₂CH₃ | NHCOCH₃ |
| Br | i-C₃H₇ | OCH₂CF₃ | SO₂CH₂CH₃ | NHCOCH₂CH₃ |
| I | n-C₄H₉ | NHCH₃ | N(CH₃)₂ | OSO₂CH₃ |
| OH | t-C₄H₉ | NHCH₂CH₃ | N(C₂H₅)₂ | OSO₂CH₂CH₃ |
| CN | CH₂Cl | NH(CH₂)₂CH₃ | OCH₂CH=CH₂ | OCH₂OCH₃ |
| NO₂ | CF₃ | NHCH(CH₃)₂ | OCH₂CH=CCl₂ | OCH₂OCH₂CH₃ |
| COOH | CH₂CF₃ | NHCH₂CF₃ | OCH₂C≡CH | OCH₂CO₂CH₃ |

The present invention is also explained by the following compounds having general formula II with antitumor activity in Table 6-Table 21, but without being restricted thereby.

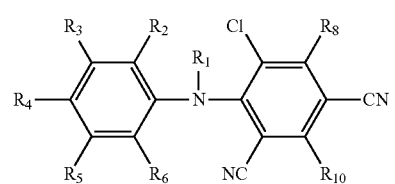

Table 6: In formula II, $R_1$ is H, $R_8$ and $R_{10}$ are Cl, $R_2$, $R_3$, $R_4$, $R_5$ and $R_6$ (hereinafter abbreviated to $R_2$-$R_6$) are listed in following Table, the numbers of representative compounds are Table 6-1 to Table 6-208.

TABLE 6

| Number | $R_2$ | $R_3$ | $R_4$ | $R_5$ | $R_6$ |
|---|---|---|---|---|---|
| 1 | H | H | H | H | H |
| 2 | F | H | H | H | H |
| 3 | Cl | H | H | H | H |
| 4 | Br | H | H | H | H |
| 5 | I | H | H | H | H |
| 6 | CH$_3$ | H | H | H | H |
| 7 | OCH$_3$ | H | H | H | H |
| 8 | NO$_2$ | H | H | H | H |
| 9 | CF$_3$ | H | H | H | H |
| 10 | CN | H | H | H | H |
| 11 | H | F | H | H | H |
| 12 | H | Cl | H | H | H |
| 13 | H | Br | H | H | H |
| 14 | H | CF$_3$ | H | H | H |
| 15 | H | H | F | H | H |
| 16 | H | H | Cl | H | H |
| 17 | H | H | Br | H | H |
| 18 | H | H | CH$_3$ | H | H |
| 19 | H | H | t-C$_4$H$_9$ | H | H |
| 20 | H | H | OCH$_3$ | H | H |
| 21 | H | H | OCF$_3$ | H | H |
| 22 | H | H | NO$_2$ | H | H |
| 23 | H | H | CN | H | H |
| 24 | H | H | CF$_3$ | H | H |
| 25 | H | H | CO$_2$CH$_3$ | H | H |
| 26 | H | H | SO$_2$CH$_3$ | H | H |
| 27 | H | H | CONHPh | H | H |
| 28 | H | H | CONHPh-4-CH$_3$ | H | H |
| 29 | H | H | CONHPh-4-Cl | H | H |
| 30 | F | F | H | H | H |
| 31 | F | H | F | H | H |
| 32 | F | H | H | F | H |
| 33 | F | H | H | H | F |
| 34 | F | H | Cl | H | H |
| 35 | F | H | H | CF$_3$ | H |
| 36 | H | F | F | H | H |
| 37 | H | F | H | F | H |
| 38 | Cl | Cl | H | H | H |
| 39 | Cl | H | Cl | H | H |
| 40 | Cl | H | H | Cl | H |
| 41 | Cl | H | H | H | Cl |
| 42 | Cl | H | H | H | CH$_3$ |
| 43 | H | Cl | Cl | H | H |
| 44 | H | Cl | H | Cl | H |
| 45 | Cl | H | Br | H | H |
| 46 | Br | H | Cl | H | H |
| 47 | Cl | H | CF$_3$ | H | H |
| 48 | Cl | H | H | CF$_3$ | H |
| 49 | Cl | H | NO$_2$ | H | H |
| 50 | Cl | H | H | NO$_2$ | H |
| 51 | Cl | H | H | CN | H |
| 52 | Cl | H | H | CH$_3$ | H |
| 53 | NO$_2$ | H | H | Cl | H |
| 54 | CN | H | H | Cl | H |
| 55 | CH$_3$ | H | H | Cl | H |
| 56 | CF$_3$ | H | CN | H | H |
| 57 | F | H | CN | H | H |
| 58 | Cl | H | CN | H | H |
| 59 | Br | H | CN | H | H |
| 60 | NO$_2$ | H | CN | H | H |
| 61 | t-C$_4$H$_9$ | H | CN | H | H |
| 62 | OCH$_3$ | H | CN | H | H |
| 63 | CO$_2$CH$_3$ | H | CN | H | H |
| 64 | SO$_2$CH$_3$ | H | CN | H | H |
| 65 | H | F | CN | H | H |
| 66 | H | Cl | CN | H | H |
| 67 | H | Br | CN | H | H |
| 68 | H | NO$_2$ | CN | H | H |
| 69 | H | CH$_3$ | CN | H | H |
| 70 | H | OCH$_3$ | CN | H | H |
| 71 | CN | H | Cl | H | H |
| 72 | CF$_3$ | H | Cl | H | H |
| 73 | CO$_2$CH$_3$ | H | Cl | H | H |
| 74 | H | CN | Cl | H | H |
| 75 | H | CH$_3$ | Cl | H | H |
| 76 | H | CF$_3$ | Cl | H | H |
| 77 | CH$_3$ | H | Cl | H | H |
| 78 | CH$_3$ | Cl | H | H | H |
| 79 | CH$_3$ | H | CH$_3$ | H | H |
| 80 | CH$_3$ | H | H | CH$_3$ | H |
| 81 | CH$_3$ | H | CN | H | H |
| 82 | CH$_3$ | H | CF$_3$ | H | H |
| 83 | CH$_3$ | H | CO$_2$CH$_3$ | H | H |
| 84 | CH$_3$ | H | H | H | CO$_2$CH$_3$ |
| 85 | H | CF$_3$ | CN | H | H |
| 86 | H | CH$_3$ | CN | H | H |
| 87 | NO$_2$ | H | Cl | H | H |
| 88 | CN | H | NO$_2$ | H | H |
| 89 | F | F | F | H | H |
| 90 | F | H | F | H | F |
| 91 | F | H | NO$_2$ | H | F |
| 92 | Cl | Cl | Cl | H | H |
| 93 | Cl | H | Cl | H | Cl |
| 94 | Cl | Cl | H | Cl | H |
| 95 | Cl | H | CF$_3$ | H | Cl |
| 96 | Cl | H | OCF$_3$ | H | Cl |
| 97 | Cl | H | CH$_3$ | H | Cl |
| 98 | Cl | H | CN | H | Cl |
| 99 | Cl | H | NO$_2$ | H | Cl |
| 100 | Cl | H | CO$_2$CH$_3$ | H | Cl |
| 101 | Cl | H | SO$_2$CH$_3$ | H | Cl |
| 102 | Cl | H | t-C$_4$H$_9$ | H | Cl |
| 103 | Cl | H | CONHPh | H | Cl |
| 104 | Cl | H | CONHPh-4-Cl | H | Cl |
| 105 | Cl | H | CO$_2$Na | H | Cl |
| 106 | Cl | H | COOH | H | Cl |
| 107 | Cl | H | NO$_2$ | H | CH$_3$ |
| 108 | Cl | CH$_3$ | Cl | H | H |
| 109 | Cl | H | Cl | H | CN |
| 110 | Cl | H | NO$_2$ | H | F |
| 111 | Br | H | OCF$_3$ | H | Br |
| 112 | Br | H | Br | H | Br |
| 113 | Br | H | NO$_2$ | H | Cl |
| 114 | Br | H | NO$_2$ | H | Br |
| 115 | CH$_3$ | H | CH$_3$ | H | CH$_3$ |
| 116 | CH$_3$ | H | t-C$_4$H$_9$ | H | CH$_3$ |
| 117 | C$_2$H$_5$ | H | Cl | H | C$_2$H$_5$ |
| 118 | CH$_3$ | H | CO$_2$CH$_3$ | H | Br |
| 119 | CH$_3$ | H | CO$_2$CH$_3$ | H | NO$_2$ |
| 120 | CH$_3$ | H | CO$_2$CH$_3$ | H | CN |
| 121 | CH$_3$ | H | CO$_2$CH$_3$ | H | OCH$_3$ |
| 122 | CH$_3$ | H | CO$_2$CH$_3$ | H | CF$_3$ |
| 123 | CH$_3$ | H | CO$_2$CH$_3$ | H | Cl |
| 124 | CH$_3$ | H | Cl | H | NO$_2$ |
| 125 | C$_2$H$_5$ | H | NO$_2$ | H | F |
| 126 | C$_2$H$_5$ | H | NO$_2$ | H | Cl |
| 127 | C$_2$H$_5$ | H | NO$_2$ | H | Br |
| 128 | C$_2$H$_5$ | H | NO$_2$ | H | NO$_2$ |
| 129 | C$_2$H$_5$ | H | NO$_2$ | H | CN |
| 130 | C$_2$H$_5$ | H | NO$_2$ | H | OCH$_3$ |
| 131 | C$_2$H$_5$ | H | NO$_2$ | H | CF$_3$ |
| 132 | C$_2$H$_5$ | H | NO$_2$ | H | CO$_2$CH$_3$ |
| 133 | C$_2$H$_5$ | H | NO$_2$ | H | SO$_2$CH$_3$ |
| 134 | C$_2$H$_5$ | Cl | H | H | C$_2$H$_5$ |
| 135 | Cl | H | CN | H | F |
| 136 | Cl | H | CN | H | Br |
| 137 | Cl | H | CN | H | NO$_2$ |
| 138 | Cl | H | CN | H | OCH$_3$ |
| 139 | Cl | H | CN | H | CO$_2$CH$_3$ |
| 140 | F | H | CN | H | Br |
| 141 | F | H | CN | H | NO$_2$ |
| 142 | F | H | CN | H | OCH$_3$ |
| 143 | F | H | CN | H | CO$_2$CH$_3$ |
| 144 | Cl | H | SO$_2$NHCH$_3$ | H | Cl |
| 145 | Cl | H | SO$_2$N(CH$_3$)$_2$ | H | Cl |
| 146 | Cl | H | CO$_2$NH$_4$ | H | Cl |
| 147 | Cl | H | CONH$_2$ | H | Cl |
| 148 | Cl | H | CONHCH$_3$ | H | Cl |

TABLE 6-continued

| Number | $R_2$ | $R_3$ | $R_4$ | $R_5$ | $R_6$ |
|---|---|---|---|---|---|
| 149 | Cl | H | $CON(CH_3)_2$ | H | Cl |
| 150 | Cl | H | $CONHCH(CH_3)_2$ | H | Cl |
| 151 | Cl | H | $CONHC(CH_3)_3$ | H | Cl |
| 152 | $CH_3$ | H | Cl | $CH_3$ | H |
| 153 | $NO_2$ | H | Cl | H | $NO_2$ |
| 154 | CN | H | Cl | H | $NO_2$ |
| 155 | CN | H | Cl | H | $CH_3$ |
| 156 | CN | H | Cl | H | CN |
| 157 | CN | H | Cl | H | $CF_3$ |
| 158 | $CO_2CH_3$ | H | Cl | H | Cl |
| 159 | $CH_3$ | H | Cl | H | Cl |
| 160 | $NO_2$ | H | Cl | H | Cl |
| 161 | $CF_3$ | H | Cl | H | Cl |
| 162 | $OCH_3$ | H | Cl | H | Cl |
| 163 | $NO_2$ | H | Cl | H | F |
| 164 | $NO_2$ | H | Cl | H | Br |
| 165 | $NO_2$ | H | Cl | H | $CF_3$ |
| 166 | $NO_2$ | H | Cl | H | $CO_2CH_3$ |
| 167 | $NO_2$ | H | Cl | H | $CH_3$ |
| 168 | CN | H | $NO_2$ | H | $NO_2$ |
| 169 | COOH | H | CN | H | $CH_3$ |
| 170 | COOH | H | Cl | H | Cl |
| 171 | COOH | H | Cl | H | $CH_3$ |
| 172 | COOH | H | Br | H | $CH_3$ |
| 173 | COOH | H | CN | H | Cl |
| 174 | $CO_2CH_3$ | H | Cl | H | $CH_3$ |
| 175 | $CO_2CH_3$ | H | Br | H | $CH_3$ |
| 176 | $CONHCH_3$ | H | CN | H | $CH_3$ |
| 177 | $CONHCH_3$ | H | Cl | H | Cl |
| 178 | $CONHCH_3$ | H | Cl | H | $CH_3$ |
| 179 | $CONHCH_3$ | H | Br | H | $CH_3$ |
| 180 | $CONHCH_3$ | H | H | H | H |
| 181 | $CONH_2$ | H | CN | H | $CH_3$ |
| 182 | $CONH_2$ | H | Cl | H | Cl |
| 183 | $CONH_2$ | H | Cl | H | $CH_3$ |
| 184 | $CONH_2$ | H | Br | H | $CH_3$ |
| 185 | $CONH_2$ | H | CN | H | Cl |
| 186 | $CON(CH_3)_2$ | H | CN | H | $CH_3$ |
| 187 | $CON(CH_3)_2$ | H | Cl | H | Cl |
| 188 | $CON(CH_3)_2$ | H | Cl | H | $CH_3$ |
| 189 | $CON(CH_3)_2$ | H | Br | H | $CH_3$ |
| 190 | $CON(CH_3)_2$ | H | CN | H | Cl |
| 191 | $CONHCH(CH_3)_2$ | H | CN | H | $CH_3$ |
| 192 | $CONHCH(CH_3)_2$ | H | Cl | H | Cl |
| 193 | $CONHCH(CH_3)_2$ | H | Cl | H | $CH_3$ |
| 194 | $CONHCH(CH_3)_2$ | H | Br | H | $CH_3$ |
| 195 | $CONHCH(CH_3)_2$ | H | CN | H | Cl |
| 196 | $CONHC(CH_3)_3$ | H | CN | H | $CH_3$ |
| 197 | $CONHC(CH_3)_3$ | H | Cl | H | Cl |
| 198 | $CONHC(CH_3)_3$ | H | Cl | H | $CH_3$ |
| 199 | $CONHC(CH_3)_3$ | H | Br | H | $CH_3$ |
| 200 | $CONHC(CH_3)_3$ | H | CN | H | Cl |
| 201 | Cl | H | Br | H | Cl |
| 202 | Cl | H | $SO_2NH_2$ | H | Cl |
| 203 | Cl | H | $SO_2NH_2$ | H | Br |
| 204 | Br | H | $SO_2NH_2$ | H | Br |
| 205 | Cl | $CH_3$ | CN | Cl | H |
| 206 | $CH_3$ | Cl | $NO_2$ | H | $NO_2$ |
| 207 | $NO_2$ | $CH_3$ | Cl | H | $NO_2$ |
| 208 | CN | Cl | CN | Cl | Cl |

Table 7: In formula II, $R_1$ is $CH_3$, $R_8$ and $R_{10}$ are Cl, $R_2$-$R_6$ are listed in Table 6, the number of representative compounds are Table 7-1 to Table 7-208.

Table 8: In formula II, $R_1$ is H, $R_8$ and $R_{10}$ are F, $R_2$-$R_6$ are listed in Table 6, the number of representative compounds are Table 8-1 to Table 8-208.

Table 9: In formula II, $R_1$ is H, $R_8$ is $N(C_2H_5)_2$, $R_{10}$ is Cl, $R_2$-$R_6$ are listed in Table 6, the number of representative compounds are Table 9-1 to Table 9-208.

Table 10: In formula II, $R_1$ is H, $R_8$ is $N(CH_3)_2$, $R_{10}$ is Cl, $R_2$-$R_6$ are listed in Table 6, the number of representative compounds are Table 10-1 to Table 10-208.

Table 11: In formula II, $R_1$ is H, $R_8$ is $NHCH_3$, $R_{10}$ is Cl, $R_2$-$R_6$ are listed in Table 6, the number of representative compounds are Table 11-1 to Table 11-208.

Table 12: In formula II, $R_1$ is H, $R_8$ is $OCH_3$, $R_{10}$ is Cl, $R_2$-$R_6$ are listed in Table 6, the number of representative compounds are Table 12-1 to Table 12-208.

Table 13: In formula II, $R_1$ is H, $R_8$ is $SCH_3$, $R_{10}$ is Cl, $R_2$-$R_6$ are listed in Table 6, the number of representative compounds are Table 13-1 to Table 13-208.

Table 14: In formula II, $R_1$ is H, $R_8$ and $R_{10}$ are $OCH_3$, $R_2$-$R_6$ are listed in Table 6, the number of representative compounds are Table 14-1 to Table 14-208.

Table 15: In formula II, $R_1$ is H, $R_8$ and $R_{10}$ are $N(CH_3)_2$, $R_2$-$R_6$ are listed in Table 6, the number of representative compounds are Table 15-1 to Table 15-208.

Table 16: In formula II, $R_1$ is H, $R_8$ and $R_{10}$ are $NHCH_3$, $R_2$-$R_6$ are listed in Table 6, the number of representative compounds are Table 16-1 to Table 16-208.

Table 17: In formula II, $R_1$ is H, $R_8$ and $R_{10}$ are $SCH_3$, $R_2$-$R_6$ are listed in Table 6, the number of representative compounds are Table 17-1 to Table 17-208.

Table 18: In formula II, $R_1$ is H, $R_8$ is $SO_2CH_3$, $R_{10}$ is Cl, $R_2$-$R_6$ are listed in Table 6, the number of representative compounds are Table 18-1 to Table 18-208.

Table 19: In formula II, $R_1$ is H, $R_8$ is $OCH_2CH=CH_2$, $R_{10}$ is Cl, $R_2$-$R_6$ are listed in Table 6, the number of representative compounds are Table 19-1 to Table 19-208.

Table 20: In formula II, $R_1$ is H, $R_8$ is $OCH_3$, $R_{10}$ is F, $R_2$-$R_6$ are listed in Table 6, the number of representative compounds are Table 20-1 to Table 20-208.

Table 21: In formula II, $R_1$ is H, $R_8$ is $N(CH_3)_2$, $R_{10}$ is F, $R_2$-$R_6$ are listed in Table 6, the number of representative compounds are Table 21-1 to Table 21-208.

The present invention is also explained by the following compounds having general formula III with antitumor activity in Table 22-Table 30, but without being restricted thereby.

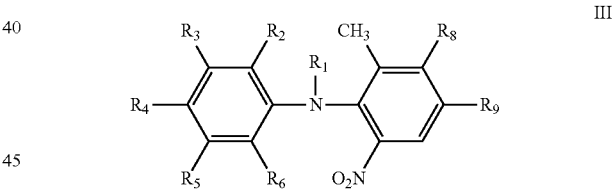

III

Table 22: In general formula III, $R_1$ is H, $R_8$ is Cl, $R_9$ is $NO_2$, $R_2$, $R_3$, $R_4$, $R_5$ and $R_6$ (hereinafter abbreviated to $R_2$-$R_6$) are listed in following Table, the numbers of representative compounds are Table 22-1 to Table 22-208.

TABLE 22

| Number | $R_2$ | $R_3$ | $R_4$ | $R_5$ | $R_6$ |
|---|---|---|---|---|---|
| 1 | H | H | H | H | H |
| 2 | F | H | H | H | H |
| 3 | Cl | H | H | H | H |
| 4 | Br | H | H | H | H |
| 5 | I | H | H | H | H |
| 6 | $CH_3$ | H | H | H | H |
| 7 | $OCH_3$ | H | H | H | H |
| 8 | $NO_2$ | H | H | H | H |
| 9 | $CF_3$ | H | H | H | H |
| 10 | CN | H | H | H | H |
| 11 | $CO_2Ph$ | H | H | H | H |
| 12 | H | F | H | H | H |
| 13 | H | Cl | H | H | H |

TABLE 22-continued

| Number | $R_2$ | $R_3$ | $R_4$ | $R_5$ | $R_6$ |
|---|---|---|---|---|---|
| 14 | H | Br | H | H | H |
| 15 | H | $CF_3$ | H | H | H |
| 16 | H | H | F | H | H |
| 17 | H | H | Cl | H | H |
| 18 | H | H | Br | H | H |
| 19 | H | H | $CH_3$ | H | H |
| 20 | H | H | $OCH_3$ | H | H |
| 21 | H | H | $OCF_3$ | H | H |
| 22 | H | H | $NO_2$ | H | H |
| 23 | H | H | CN | H | H |
| 24 | H | H | $CF_3$ | H | H |
| 25 | H | H | $CO_2CH_3$ | H | H |
| 26 | H | H | $SO_2CH_3$ | H | H |
| 27 | H | H | CONHPh | H | H |
| 28 | H | H | CONHPh-4-$CH_3$ | H | H |
| 29 | H | H | CONHPh-4-Cl | H | H |
| 30 | F | F | H | H | H |
| 31 | F | H | F | H | H |
| 32 | F | H | H | F | H |
| 33 | F | H | H | H | F |
| 34 | F | H | Cl | H | H |
| 35 | F | H | H | $CF_3$ | H |
| 36 | H | F | F | H | H |
| 37 | H | F | H | F | H |
| 38 | Cl | Cl | H | H | H |
| 39 | Cl | H | Cl | H | H |
| 40 | Cl | H | H | Cl | H |
| 41 | Cl | H | H | H | Cl |
| 42 | Cl | H | H | H | $CH_3$ |
| 43 | H | Cl | Cl | H | H |
| 44 | H | Cl | H | Cl | H |
| 45 | Cl | H | Br | H | H |
| 46 | Br | H | Cl | H | H |
| 47 | Cl | H | $CF_3$ | H | H |
| 48 | Cl | $CH_3$ | H | H | H |
| 49 | Cl | H | H | $CF_3$ | H |
| 50 | Cl | H | $NO_2$ | H | H |
| 51 | Cl | H | H | $NO_2$ | H |
| 52 | Cl | H | H | CN | H |
| 53 | Cl | H | H | $CH_3$ | H |
| 54 | $NO_2$ | H | H | Cl | H |
| 55 | CN | H | H | Cl | H |
| 56 | $CH_3$ | H | H | Cl | H |
| 57 | $CH_3$ | H | H | H | Cl |
| 58 | $CH_3$ | Cl | H | H | H |
| 59 | $CF_3$ | H | CN | H | H |
| 60 | F | H | CN | H | H |
| 61 | Cl | H | CN | H | H |
| 62 | Br | H | CN | H | H |
| 63 | $NO_2$ | H | CN | H | H |
| 64 | $t-C_4H_9$ | H | CN | H | H |
| 65 | $OCH_3$ | H | CN | H | H |
| 66 | $CO_2CH_3$ | H | CN | H | H |
| 67 | $SO_2CH_3$ | H | CN | H | H |
| 68 | H | F | CN | H | H |
| 69 | H | Cl | CN | H | H |
| 70 | H | Br | CN | H | H |
| 71 | H | $NO_2$ | CN | H | H |
| 72 | H | $CH_3$ | CN | H | H |
| 73 | H | $OCH_3$ | CN | H | H |
| 74 | CN | H | Cl | H | H |
| 75 | $CF_3$ | H | Cl | H | H |
| 76 | $CO_2CH_3$ | H | Cl | H | H |
| 77 | H | CN | Cl | H | H |
| 78 | H | $CH_3$ | Cl | H | H |
| 79 | H | $CF_3$ | Cl | H | H |
| 80 | $CH_3$ | H | Cl | H | H |
| 81 | $CH_3$ | H | $CH_3$ | H | H |
| 82 | $CH_3$ | H | H | $CH_3$ | H |
| 83 | $CH_3$ | H | CN | H | H |
| 84 | $CH_3$ | H | $CF_3$ | H | H |
| 85 | $CH_3$ | H | $CO_2CH_3$ | H | H |
| 86 | H | $CF_3$ | CN | H | H |
| 87 | H | $CH_3$ | CN | H | H |
| 88 | $NO_2$ | H | Cl | H | H |
| 89 | $NO_2$ | H | $NO_2$ | H | H |
| 90 | CN | H | $NO_2$ | H | H |
| 91 | F | F | F | H | H |
| 92 | F | H | F | H | F |
| 93 | F | H | Cl | H | F |
| 94 | F | H | F | H | $NO_2$ |
| 95 | F | H | $NO_2$ | H | F |
| 96 | Cl | Cl | Cl | H | H |
| 97 | Cl | H | Cl | Cl | H |
| 98 | Cl | H | Cl | H | Cl |
| 99 | Cl | Cl | H | Cl | H |
| 100 | Cl | H | Br | H | Cl |
| 101 | Cl | H | $CF_3$ | H | Cl |
| 102 | Cl | H | $OCF_3$ | H | Cl |
| 103 | Cl | H | $CH_3$ | H | Cl |
| 104 | Cl | H | CN | H | Cl |
| 105 | Cl | H | $NO_2$ | H | Cl |
| 106 | Cl | H | $NO_2$ | Cl | H |
| 107 | Cl | H | $CO_2CH_3$ | H | Cl |
| 108 | Cl | H | $SO_2CH_3$ | H | Cl |
| 109 | Cl | H | $SO_2NH_2$ | H | Cl |
| 110 | Cl | H | $SO_2NH_2$ | H | Br |
| 111 | Br | H | $SO_2NH_2$ | H | Br |
| 112 | Cl | H | $t-C_4H_9$ | H | Cl |
| 113 | Cl | H | CONHPh | H | Cl |
| 114 | Cl | H | CONHPh-4-Cl | H | Cl |
| 115 | Cl | H | $CO_2Na$ | H | Cl |
| 116 | Cl | H | COOH | H | Cl |
| 117 | Cl | H | $NO_2$ | H | $CH_3$ |
| 118 | Cl | H | $NO_2$ | H | $NO_2$ |
| 119 | Cl | $CH_3$ | Cl | H | H |
| 120 | Cl | H | Cl | H | CN |
| 121 | Cl | H | Cl | H | $NO_2$ |
| 122 | Cl | H | $NO_2$ | H | F |
| 123 | Cl | H | $NO_2$ | H | Br |
| 124 | Cl | H | $OCF_2CHFCF_3$ | Cl | H |
| 125 | H | Cl | 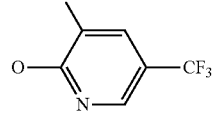 | Cl | H |
| 126 | Br | H | $OCF_3$ | H | Br |
| 127 | Br | H | Br | H | Br |
| 128 | Br | H | $NO_2$ | H | Cl |
| 129 | Br | H | $NO_2$ | H | Br |
| 130 | Br | H | $NO_2$ | H | CN |
| 131 | $CH_3$ | H | $CH_3$ | H | $CH_3$ |
| 132 | $CH_3$ | H | $t-C_4H_9$ | H | $CH_3$ |
| 133 | $C_2H_5$ | H | Cl | H | $C_2H_5$ |
| 134 | $CH_3$ | H | $CO_2CH_3$ | H | Br |
| 135 | $CH_3$ | H | $CO_2CH_3$ | H | $NO_2$ |
| 136 | $CH_3$ | H | $CO_2CH_3$ | H | CN |
| 137 | $CH_3$ | H | $CO_2CH_3$ | H | $OCH_3$ |
| 138 | $CH_3$ | H | $CO_2CH_3$ | H | $CF_3$ |
| 139 | $CH_3$ | Cl | $NO_2$ | H | H |
| 140 | $CH_3$ | H | $NO_2$ | H | Cl |
| 141 | $C_2H_5$ | H | $NO_2$ | H | F |
| 142 | $C_2H_5$ | H | $NO_2$ | H | Cl |
| 143 | $C_2H_5$ | H | $NO_2$ | H | Br |
| 144 | $C_2H_5$ | H | $NO_2$ | H | $NO_2$ |
| 145 | $C_2H_5$ | H | $NO_2$ | H | CN |
| 146 | $C_2H_5$ | H | $NO_2$ | H | $OCH_3$ |
| 147 | $C_2H_5$ | H | $NO_2$ | H | $CF_3$ |
| 148 | $C_2H_5$ | H | $NO_2$ | H | $CO_2CH_3$ |
| 149 | $C_2H_5$ | H | $NO_2$ | H | $SO_2CH_3$ |
| 150 | Cl | H | $CF_3$ | H | F |
| 151 | Cl | H | $CF_3$ | H | Br |
| 152 | Cl | H | $CF_3$ | H | $NO_2$ |
| 153 | Cl | H | CN | H | $NO_2$ |
| 154 | Cl | H | $CF_3$ | H | $OCH_3$ |
| 155 | Cl | H | $CF_3$ | H | $CO_2CH_3$ |
| 156 | F | H | $CF_3$ | H | Br |
| 157 | F | H | $CF_3$ | H | $NO_2$ |
| 158 | F | H | $CF_3$ | H | $OCH_3$ |
| 159 | F | H | $CF_3$ | H | $CO_2CH_3$ |
| 160 | Cl | H | $SO_2NHCH_3$ | H | Cl |
| 161 | Cl | H | $SO_2N(CH_3)_2$ | H | Cl |
| 162 | Cl | H | $CO_2NH_4$ | H | Cl |

TABLE 22-continued

| Number | $R_2$ | $R_3$ | $R_4$ | $R_5$ | $R_6$ |
|---|---|---|---|---|---|
| 163 | Cl | H | $CONH_2$ | H | Cl |
| 164 | Cl | H | $CONHCH_3$ | H | Cl |
| 165 | Cl | H | $CON(CH_3)_2$ | H | Cl |
| 166 | Cl | H | $CONHCH(CH_3)_2$ | H | Cl |
| 167 | Cl | H | $CONHC(CH_3)_3$ | H | Cl |
| 168 | $CH_3$ | H | Cl | H | $CH_3$ |
| 169 | $NO_2$ | H | Cl | H | $NO_2$ |
| 170 | $NO_2$ | H | $NO_2$ | H | $NO_2$ |
| 171 | $NO_2$ | H | $CF_3$ | H | $NO_2$ |
| 172 | $NO_2$ | H | CN | $CF_3$ | H |
| 173 | CN | H | Cl | H | $NO_2$ |
| 174 | CN | H | Cl | H | $CH_3$ |
| 175 | CN | H | Cl | H | CN |
| 176 | CN | H | Cl | H | $CF_3$ |
| 177 | $CO_2CH_3$ | H | Cl | H | Cl |
| 178 | $CH_3$ | H | Cl | H | Cl |
| 179 | $NO_2$ | H | Cl | H | Cl |
| 180 | $NO_2$ | H | Cl | Cl | H |
| 181 | $CF_3$ | H | Cl | H | Cl |
| 182 | $OCH_3$ | H | Cl | H | Cl |
| 183 | $NO_2$ | H | Cl | H | F |
| 184 | $NO_2$ | H | Cl | H | Br |
| 185 | $NO_2$ | H | Cl | H | $CF_3$ |
| 186 | $NO_2$ | H | Cl | H | $CO_2CH_3$ |
| 187 | $NO_2$ | H | Cl | H | $CH_3$ |
| 188 | CN | H | $NO_2$ | H | $NO_2$ |
| 189 | COOH | H | CN | H | $CH_3$ |
| 190 | COOH | H | Cl | H | Cl |
| 191 | COOH | H | Cl | H | $CH_3$ |
| 192 | COOH | H | Br | H | $CH_3$ |
| 193 | COOH | H | CN | H | Cl |
| 194 | $CO_2CH_3$ | H | Cl | H | $CH_3$ |
| 195 | $CO_2CH_3$ | H | Br | H | $CH_3$ |
| 196 | $CONHCH_3$ | H | CN | H | $CH_3$ |
| 197 | $CONHCH_3$ | H | Cl | H | Cl |
| 198 | $CONHCH_3$ | H | Cl | H | $CH_3$ |
| 199 | $CONHCH_3$ | H | Br | H | $CH_3$ |
| 200 | $CONHCH_3$ | H | CN | H | Cl |
| 201 | $CONH_2$ | H | CN | H | $CH_3$ |
| 202 | $CONH_2$ | H | Cl | H | Cl |
| 203 | $CONH_2$ | H | Cl | H | $CH_3$ |
| 204 | $CONH_2$ | H | Br | H | $CH_3$ |
| 205 | $CONH_2$ | H | CN | H | Cl |
| 206 | $NO_2$ | Cl | $CF_3$ | H | $NO_2$ |
| 207 | Cl | H | $NO_2$ | Cl | $NO_2$ |
| 208 | Cl | H | Cl | Cl | $NO_2$ |

Table 23: In formula III, $R_1$ and $R_9$ are H, $R_8$ is Cl, $R_2$-$R_6$ are listed in Table 22, the number of representative compounds are Table 23-1 to Table 23-208.

Table 24: In formula III, $R_1$ is $CH_3$, $R_8$ is Cl, $R_9$ is $NO_2$, $R_2$-$R_6$ are listed in Table 22, the number of representative compounds are Table 24-1 to Table 24-208.

Table 25: In formula III, $R_1$ is H, $R_8$ is $OCH_3$, $R_9$ is $NO_2$, $R_2$-$R_6$ are listed in Table 22, the number of representative compounds are Table 25-1 to Table 25-208.

Table 26: In formula III, $R_1$ is H, $R_8$ is $SCH_3$, $R_9$ is $NO_2$, $R_2$-$R_6$ are listed in Table 22, the number of representative compounds are Table 26-1 to Table 26-208.

Table 27: In formula III, $R_1$ is H, $R_8$ is $NHCH_3$, $R_9$ is $NO_2$, $R_2$-$R_6$ are listed in Table 22, the number of representative compounds are Table 27-1 to Table 27-208.

Table 28: In formula III, $R_1$ is H, $R_8$ is $N(CH_3)_2$, $R_9$ is $NO_2$, $R_2$-$R_6$ are listed in Table 22, the number of representative compounds are Table 28-1 to Table 28-208.

Table 29: In formula III, $R_1$ is H, $R_8$ is $OCH_2CF_3$, $R_9$ is $NO_2$, $R_2$-$R_6$ are listed in Table 22, the number of representative compounds are Table 29-1 to Table 29-208.

Table 30: In formula III, $R_1$ and $R_8$ is H, $R_9$ is $NO_2$, $R_2$-$R_6$ are listed in Table 22, the number of representative compounds are Table 30-1 to Table 30-208.

The compounds having formula I in present invention have been reported in prior art, which are commercial available or can be prepared according to the following method. The reaction is as follow, wherein the definitions of substituents are as defined above:

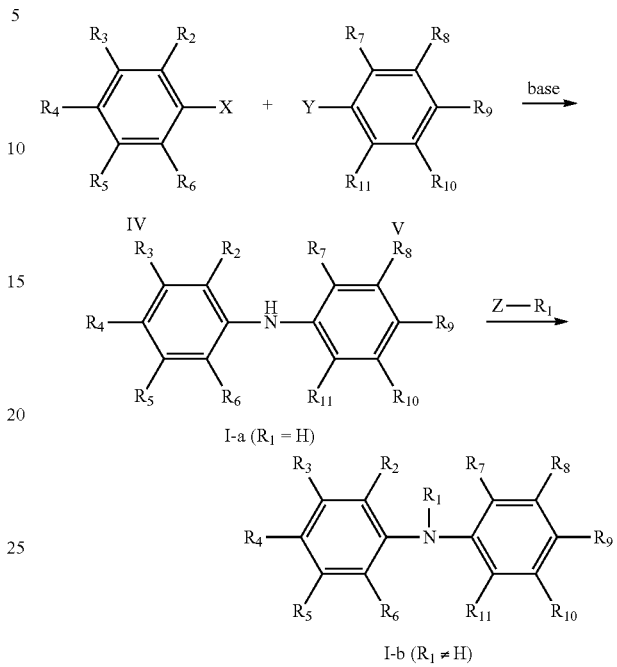

Wherein: X and Y are different, respectively selected from halogen atom or amino; Z is halogen atom; $R_2$, $R_3$, $R_4$, $R_5$, $R_6$, $R_7$, $R_8$, $R_9$, $R_{10}$ and $R_{11}$ are defined respectively as mentioned above; $R_1$ are defined as mentioned above, but $R_1 \neq H$.

According to the above preparation method, treatment of intermediate IV with intermediate V at the presence of base gives compounds I-a of general formula I ($R_1$=H), which react with Z—$R_1$ to give compounds I-b of general formula I ($R_1 \neq H$).

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction can be carried out in proper solvent, and the proper solvent mentioned may be selected from tetrahydrofuran, acetonitrile, toluene, xylene, benzene, DMF, N-methylpyrrolidone, DMSO, acetone or butanone and so on.

The proper reaction temperature is from room temperature to boiling point of solvent, generally is 20-100° C.

The reaction time is in the range of 30 minutes to 20 hours, generally is 1-10 hours.

Intermediates IV are commercially available, or prepared according to the known methods, such as referring to Indian Journal of Chemistry, Section B: Organic Chemistry Including Medicinal Chemistry, 45B(4), 972-975, 2006; Tetrahedron Letters, 44(21), 4085-4088, 2003; PL174903, etc.

Intermediate V can be prepared according to the known methods, such as referring to JP2003292476, 052010160695, etc.

The nitration of compounds of general formula I, in which at least one of $R_2$, $R_4$, $R_6$, $R_9$ or $R_{11}$ is H, can add one or several $NO_2$ groups to these compounds of general formula I.

The halogenation of substituted diphenylamine compounds of general formula I, in which $R_2$, $R_4$, $R_6$, $R_7$, $R_9$ or $R_{11}$ is not halogen atom, can add one or several halogen atoms to these compounds of general formula I.

The compounds of general formula I, in which $R_8$ and $R_{10}$ are alkylamino, alkoxy or alkylthio, can be prepared from the reaction of compounds of general formula I whose $R_8$ and $R_{10}$ are halogen atom with amine, alcohol or mercaptan (or their salts), or referring to the preparation method in *Journal of Medicinal Chemistry*, 1978, 21(9), 906-913.

The compounds of general formula I, in which $R_8$ and $R_{10}$ are alkylsulfonyl and alkylcarbonyloxy, can be prepared according to the preparation method in *Journal of Medicinal Chemistry*, 1978, 21(9), 906-913.

The salts of compounds having general formula I can be prepared from the reaction of the compounds of general formula I with corresponding acid according to routine method. The proper acid may be selected from hydrochloric acid, sulfuric acid, nitric acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid; The preferred acid are selected from hydrochloric acid, sulfuric acid, phosphoric acid, trifluoroacetic acid, methylsulfonic acid or p-toluenesulfonic acid.

The present invention includes the formulations, which were made from the compounds having the general formula I as active ingredient, and preparation thereof. The preparation of formulations: Dissolve the compounds of present invention in water soluble organic solvents, the ionicity of surfactant, water soluble lipid, all kinds of cyclodextrin, fatty acid, fatty acid ester, phospholipids or their combination solvents, and add physiological saline or 1-20% of carbohydrates. Mentioned organic solvents include polyethylene glycol (PEG), ethanol, propylene glycol or their combination solvents.

The compounds having the general formula I in present invention and their salt and prodrug can be used to prepare the drugs or formulations to cure, prevent or alleviate cancer. The active ingredients are composed of one or more than two diphenylamine compounds having the general formula I. Especially to cure or alleviate the cancer causing by cancer cells of human tissue or organ. The preferred cancers are: colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer, osteosarcoma, nasopharynx cancer or stomach cancer.

The compounds in present invention can be used as active ingredients of antitumor drug, which can be used alone or combined with other antitumorantiviral drugs. The drug combination process in present invention, using at least one of the compounds and its active derivatives with other one or more antitumorantiviral drugs, are used together to increase the overall effect. The dose and drug administration time of combination therapy are based on the most reasonable treatment effect in the different situations.

The formulations include the effective dose of the compounds having general formula I. The "effective dose" refers to the compound dosage, which are effective to cure cancer. The effective dose or dose can be different based on the suggestions of experienced person at different conditions. For instance, the different usage of drug based on different cancers; the dose of drug also can be changed based on whether it shares with other therapeutic method, such as antitumor or antiviral drugs. The drug can be prepared for any useable formulations. The salts of compounds also can be used if the alkaline or acidic compounds can formed the non-toxic acids or salts. The organic acids/salts in pharmacy include anion salts, which are formed with acids, such as p-toluenesulfonic acid, methylsulfonic acid, acetic acid, benzoic acid, citric acid, malic acid, tartaric acid, maleic acid, succinic acid, ascorbic acid or glycerophosphoric acid; the inorganic salts include chloride, bromide, fluoride, iodide, sulfate, nitrate, bicarbonate, carbonate or phosphate. For example, the alkaline compounds, such as amines can form salts with suitable acids; acids can form salts with alkalis or alkaline earth.

The compounds in present invention having general formula I general easily dissolves in organic solvent, water soluble solvent and their mixture with water. The water soluble solvents prefer alcohol, polyethylene glycol, N-methyl-2-pyrrolidone, N,N-dimethyl acetamide, N,N-dimethyl formamide, dimethylsulfoxide, acetonitrile and their mixture. Mentioned alcohols prefer methanol, ethanol, isopropanol, glycerol or ethylene glycol. The compounds in present invention mix with common drug carrier to form formulations. Dissolve the compounds of present invention in water soluble organic solvents, aprotic solvent, water soluble lipid, cyclodextrin, fatty acid, phospholipids or their combination solvents, and add physiological saline or 1-20% of carbohydrates, such as glucose aqueous solution. The stability formulations made by this way are used for animal and clinical.

The drugs were made from the active ingredients of general formula I compounds, which can dose by oral medication or parenteral route, also by implantable medication pump and other methods. Where the parenteral route refer to injection or drip technology through subcutaneous intradermal, intramuscular, intravenous, arteries, atrium, synovium, sternum, intrathecal, wound area, encephalic, etc. The formulations were mixed using conventional method by technicist, which are used for animal and clinical, including tablets, pills, capsule, granule, syrup, injection, freeze-dried powder injection, emulsion, powder, freeze-dried powder, drop pill, milk suspension, aqueous suspension, colloid, colloidal solution, sustained-release suspensions, nanoparticle or other formulations.

The compounds having the general formula I in present invention can be used to cure or alleviate the cancer causing by cancer cells of human tissue or organ. The cancers include but not limited to colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer, osteosarcoma, nasopharynx cancer or stomach cancer.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

Preparation of Compound Table 6-1

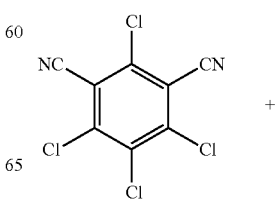

+

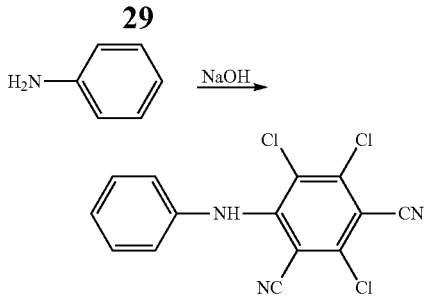

0.35 g (3.76 mmol) of aniline and 0.30 g (7.52 mmol) of sodium hydroxide were added into 40 mL of DMF, and 1.00 g (3.76 mmol) of 2,4,5,6-tetrachloroisophthalonitrile was added slowly under stirring, then stirred for another 5 h. After the reaction was over by Thin-Layer Chromatography monitoring, the reaction mixture was poured into water, and filtered to give white solid. The solid was washed twice by 30 ml water and twice by 20 ml petroleum ether, 0.65 g of compound Table 6-1 as white solid was obtained, m.p. 226-228° C.

$^1$H-NMR spectrum (300 MHz, internal standard: TMS, solvent $CDC_3$) δ(ppm): 7.22 (d, 2H, Ph-2,6-2H, J=7.5 Hz), 7.40-7.46 (m, 3H, Ph-3,4,5-3H).

Example 2

Preparation of Compound Table 6-33

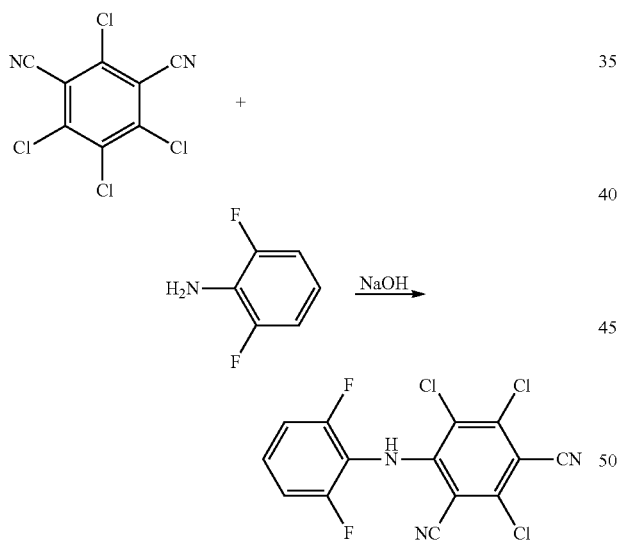

1.03 g (8 mmol) of 2,6-difluoroaniline and 0.64 g (16 mmol) of sodium hydroxide were added into 40 mL of DMF, and 2.13 g (8 mmol) of 2,4,5,6-tetrachloroisophthalonitrile was added slowly under stirring, then stirred for another 5 h. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=1/4, as an eluent) to give 1.65 g of compound table 6-33 as yellow solid, m.p. 264-266° C.

$^1$H-NMR spectrum (300 MHz, internal standard: TMS, solvent $CDC_3$) δ(ppm): 6.70 (s, 1H, NH), 7.07 (t, 2H, Ph-3,5-2H, J=8.1 Hz), 7.37 (m, 1H, Ph-4-1H).

Example 3

Preparation of Compound Table 6-39

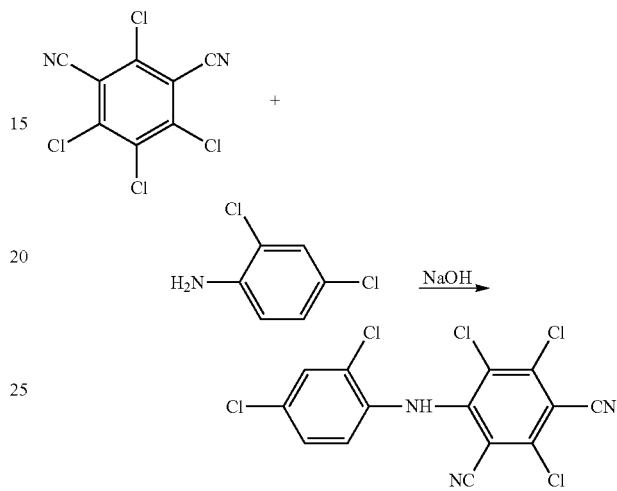

The preparation is same to compound Table 6-1, brown black solid, m.p. 209-212° C.

$^1$H-NMR spectrum (300 MHz, internal standard: TMS, solvent $CDC_3$) δ(ppm): 6.95 (s, 1H, NH), 7.20 (d, 1H, Ph-6-H, J=8.1 Hz), 7.36 (dd, 1H, Ph-5-H, $^3$J=8.7 Hz, $^4$J=2.7 Hz), 7.54 (d, 1H, Ph-3-H, J=2.4 Hz).

Example 4

Preparation of Compound Table 6-91

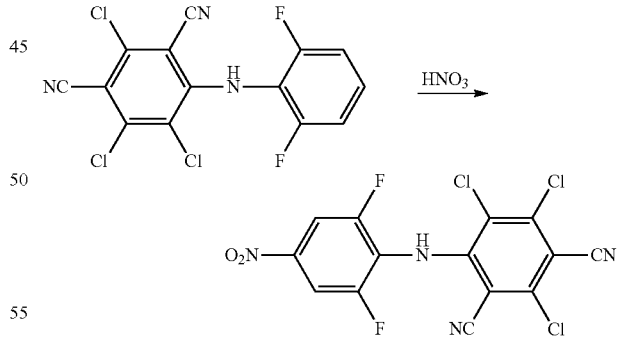

0.68 g (2 mmol) of compound table 6-33 was dissolved in 20 mL of concentrated sulfuric acid and cooled by ice-bath, the mixed acid (4 mmol of nitric acid and 6 mmol of sulfuric acid) was added dropwise to the reaction solution under stirring to keep the temperature below 20° C. Then the reaction mixture was stirred for another 5 min. After the reaction was over by Thin-Layer Chromatography monitoring, the reaction mixture was poured into ice water, extracted with ethyl acetate, the extract was washed by saturated brine, dried over anhydrous magnesium sulfate and concentrated under reduced pressure. The residue was purified through silica column (ethyl acetate/petroleum ether (boiling point range 60-90° C.)=1/4, as an eluent) to give 0.40 g of compound table 6-91 as white solid, m.p. 204-206° C.

$^1$H-NMR spectrum (300 MHz, internal standard: TMS, solvent CDC$_3$) δ(ppm): 6.70 (s, 1H, NH), 7.97-8.01 (dd, 2H, Ph-3,5-2H, $^3$J=10.8 Hz, $^4$J=3.0 Hz).

Example 5

Preparation of Compound Table 6-93

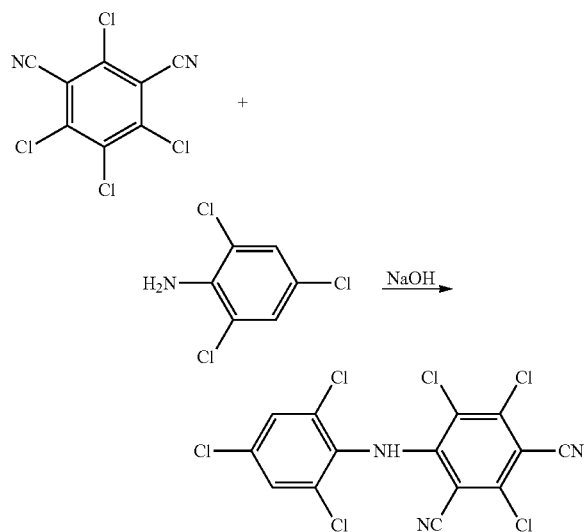

1.57 g (8 mmol) of 2,4,6-trichloroaniline and 0.64 g (16 mmol) of sodium hydroxide were added into 40 mL of DMF, and 2.13 g (8 mmol) of 2,4,5,6-tetrachloroisophthalonitrile was added slowly under stirring, then stirred for another 5 h. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=1/4, as an eluent) to give 1.91 g of compound table 6-39 as light yellow solid, m.p. 182-184° C.

$^1$H-NMR spectrum (300 MHz, internal standard: TMS, solvent CDC$_3$) δ(ppm): 6.86 (s, 1H, NH), 7.48 (s, 2H, Ph-3, 5-2H).

Example 6

Preparation of Compound Table 6-99

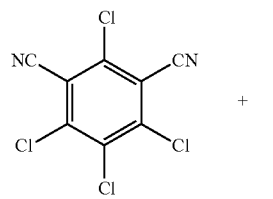

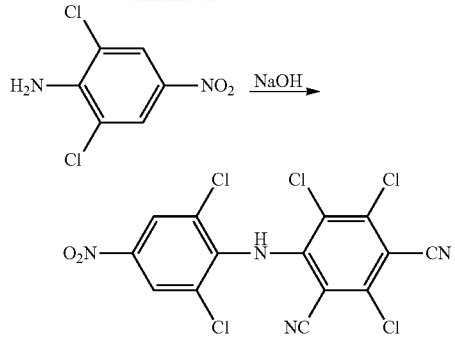

0.35 g (1.3 mmol) of 2,6-dichloro-4-nitroaniline and 0.10 g (2.6 mmol) of sodium hydroxide were added into 40 mL of DMF, and 0.27 g (1.3 mmol) of 2,4,5,6-tetrachloroisophthalonitrile was added slowly under stirring, then stirred for another 5 h. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/ petroleum ether (boiling point range 60-90° C.)=1/4, as an eluent) to give 0.48 g of compound table 6-99 as yellow solid, m.p. 250-252° C.

$^1$H-NMR spectrum (300 MHz, internal standard: TMS, solvent CDC$_3$) δ(ppm): 6.93 (s, 1H, NH), 8.34 (s, 2H, Ph-3, 5-2H).

Example 7

Preparation of Compound Table 6-100

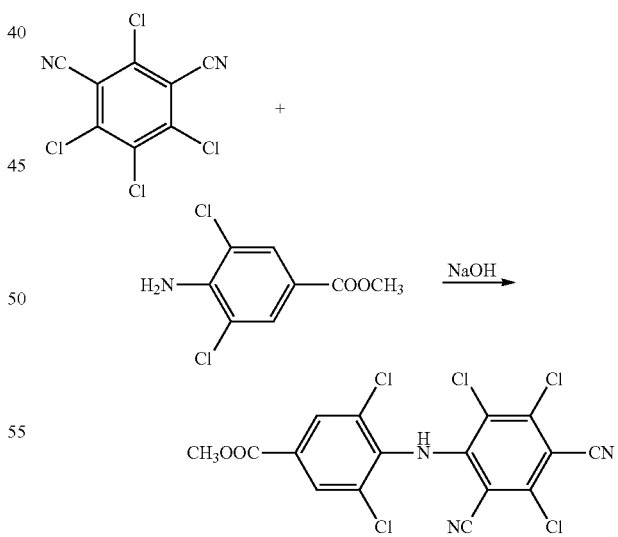

10.33 g (39 mmol) of methyl 4-amino-3,5-dichlorobenzoate (preparation refer to WO2010060379, CN101337940) and 3.12 g (78 mmol) of sodium hydroxide were added into 60 mL of DMF, and 10.37 g (39 mmol) of 2,4,5,6-tetrachloroisophthalonitrile was added slowly under stirring, then stirred for another 5 h. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=1/5, as an eluent) to give 13.65 g of compound table 6-100 as yellow solid, m.p. 229-231° C.

$^1$H-NMR spectrum (300 MHz, internal standard: TMS, solvent CDC$_3$) δ(ppm): 3.96 (s, 3H, CH$_3$), 6.92 (s, 1H, NH), 8.11 (s, 2H, Ph-2,6-2H).

Example 8

Preparation of Compound Table 6-104

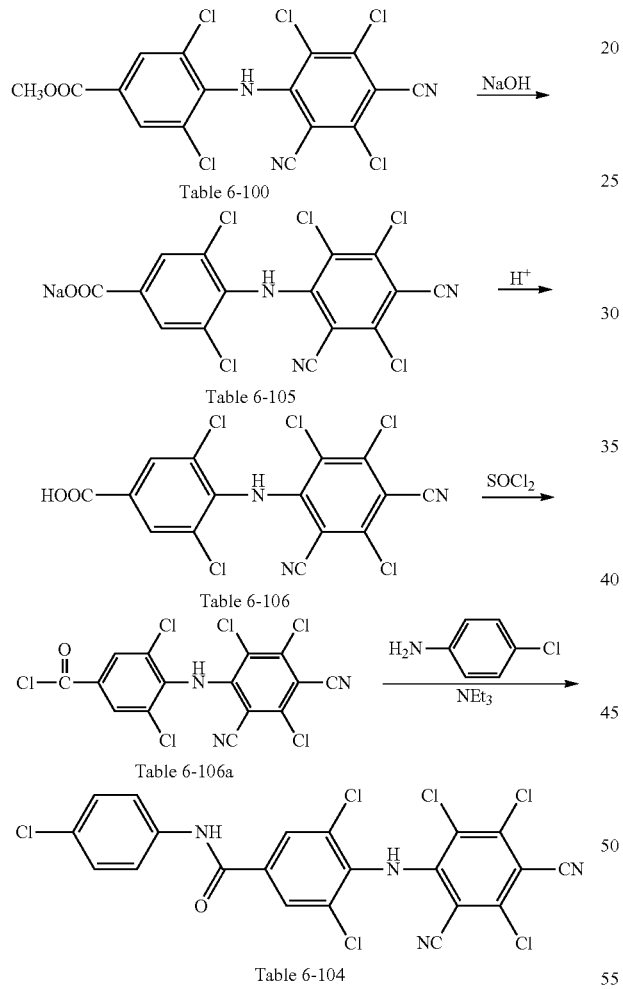

(1) Preparation of Compound Table 6-106

13.31 g (31 mmol) of compound Table 6-100 was dissolved in mixed solution of THF and water (volume ratio=1/1), and 2.45 g (61 mmol) of sodium hydroxide was added to the reaction solution followed by heating for 5 h at 50° C. in oil-bath. After the reaction was over by Thin-Layer Chromatography monitoring, the reaction mixture was poured into water, and extracted with ethyl acetate, the aqueous phase was acidized by diluted hydrochloric acid, and filtered to give compound Table 6-106 as yellow solid, dried for the next step.

(2) Preparation of Compound Table 6-106a 5.54 g (12.72 mmol) of compound Table 6-106 was added to 100 ml of petroleum ether, and two drops of DMF and 2.27 g (19.08 mmol) of thionyl chloride were added to the reaction solution followed by refluxing for 2 h at 85° C. in oil-bath. After the reaction was over by Thin-Layer Chromatography monitoring, the reaction mixture was concentrated under reduced pressure to obtain compound Table 6-106a.

(3) Preparation of Compound Table 6-104

0.12 g (0.91 mmol) of p-chloroaniline and 0.23 g (2.27 mmol) of triethylamine were dissolved in anhydrous THF, then 0.40 g (0.91 mmol) of compound Table 6-106a was added dropwise to the reaction solution followed by heating for 5 h at 45° C. in oil-bath. After the reaction was over by Thin-Layer Chromatography monitoring, the reaction mixture was poured into water, and extracted with ethyl acetate, the extract was washed by saturated brine, dried over anhydrous magnesium sulfate and concentrated under reduced pressure. The residue was purified through silica column (ethyl acetate/petroleum ether (boiling point range 60-90° C.)=1/3, as an eluent) to give 0.23 g of compound table 6-104 as white solid, m.p. 275-276° C.

$^1$H-NMR spectrum (300 MHz, internal standard: TMS, solvent CDC$_3$) δ(ppm): 7.31-7.35 (m, 2H, 4-Cl-Ph-2,6-2H), 7.81 (d, 2H, 4-Cl-Ph-3,5-2H, J=9.0 Hz), 8.13 (dd, 2H, Ph-2,6-2H, $^3$J=15.7 Hz, $^4$J=1.2 Hz), 10.50 (d, 1H, CONH, J=12.9 Hz).

Example 9

Preparation of Compound Table 6-112

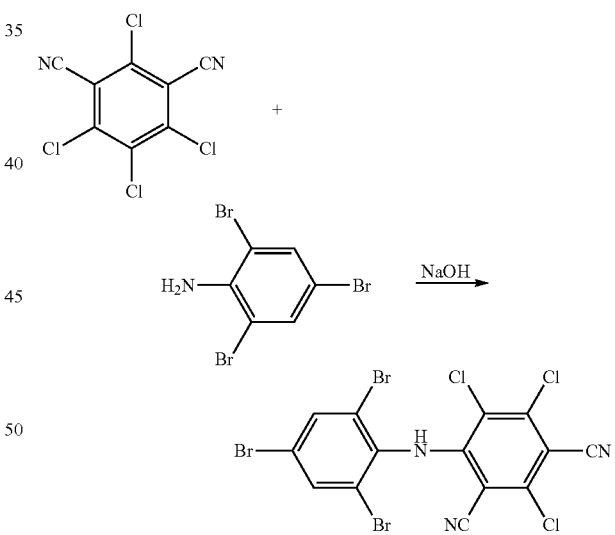

2.63 g (8 mmol) of 2,4,6-trichloroaniline and 0.64 g (16 mmol) of sodium hydroxide were added into 40 mL of DMF, and 2.13 g (8 mmol) of 2,4,5,6-tetrachloroisophthalonitrile was added slowly under stirring, then stirred for another 5 h. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=1/4, as an eluent) to give 3.22 g of compound table 6-112 as brown solid, m.p. 238-239° C.

$^1$H-NMR spectrum (300 MHz, internal standard: TMS, solvent CDC$_3$) δ(ppm): 6.86 (s, 1H, NH), 7.48 (s, 2H, Ph-3, 5-2H).

Example 10

Preparation of Compound Table 14-99

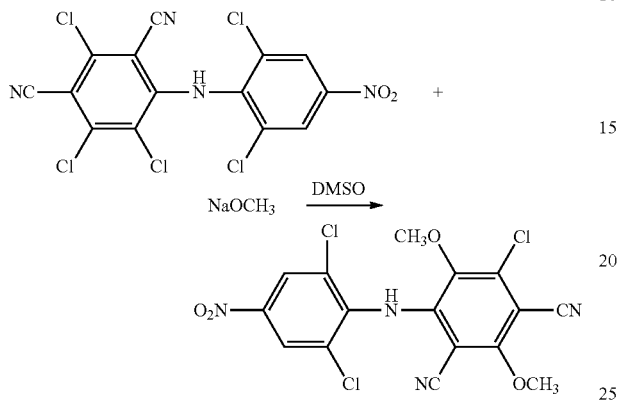

0.55 g (1.3 mmol) of compound Table 6-99 and 0.14 g (2.5 mmol) of sodium methoxide were dissolved in 20 ml of DMSO, followed by heating for 8 h at 95° C. in oil-bath. After the reaction was over by Thin-Layer Chromatography monitoring, the reaction mixture was poured into water, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=1/4, as an eluent) to give 0.16 g of compound table 14-99 as yellow solid, m.p. 151-153° C.

$^1$H-NMR spectrum (300 MHz, internal standard: TMS, solvent CDC$_3$) δ(ppm): 4.23 (t, 6H, OCH$_3$, J=6.6 Hz), 6.78 (br, 1H, NH), 8.31 (d, 2H, Ph-3,5-2H, J=3.9 Hz).

Example 11

Preparation of Compound Table 22-39

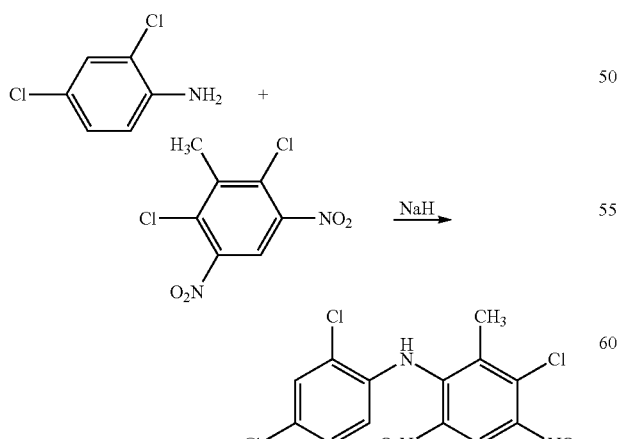

0.81 g (0.005 mol) of 2,4-dichloroaniline was added in portions to a suspension of 0.4 g (0.01 mol) of NaH (60%) and 20 mL of THF, the mixture was stirred for 30 min after addition, 1.56 g (0.006 mol) of 2,6-dichloro-3,5-dinitrotulune in 30 mL of THF was added within 30 min, then stirred for another 5 h. After the reaction was over by Thin-Layer Chromatography monitoring, the reaction mixture was filtered. The filtrate was concentrated under reduced pressure, then the residue was purified through silica column (ethyl acetate/petroleum ether (boiling point range 60-90° C.)=1/20, as an eluent) to give 1.37 g of compound table 22-39 as yellow solid, m.p. 136-137° C.

$^1$H-NMR spectrum (300 MHz, internal standard: TMS, solvent CDC$_3$) δ(ppm): 2.14 (s, 3H), 6.53 (d, 1H), 7.17 (d, 1H), 7.49 (s, 1H), 8.68 (s, 1H), 8.93 (s, 1H).

Example 12

Preparation of Compound Table 22-101

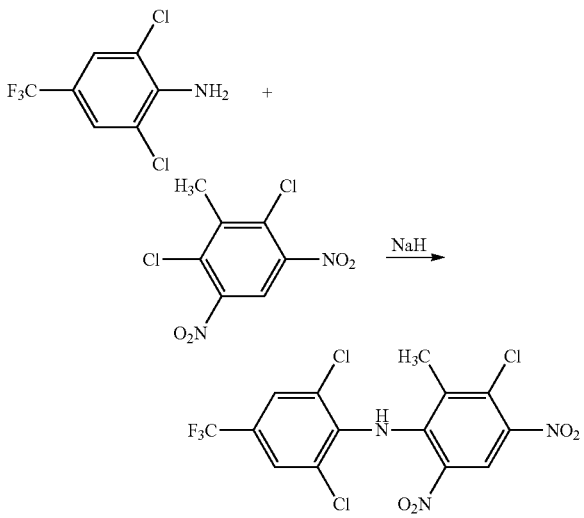

The preparation is same to compound Table 22-39, m.p. 143-144° C.

$^1$H-NMR spectrum (300 MHz, internal standard: TMS, solvent CDC$_3$) δ(ppm): 1.98 (s, 3H), 7.66 (s, 2H), 8.70 (s, 1H), 9.10 (s, 1H).

Example 13

Preparation of Compound Table 22-105

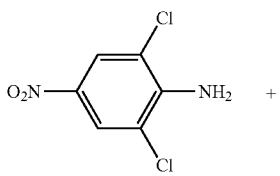

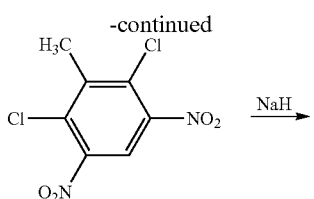

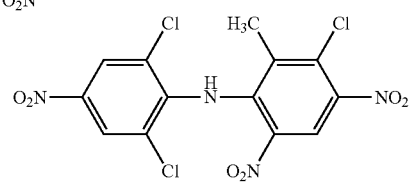

Table 22-105

0.83 g (0.004 mol) of 2,6-dichloro-4-nitroaniline was added in portions to a suspension of 0.32 g (0.008 mol) of NaH (60%) and 10 mL of DMF, the mixture was stirred for 30 min after addition, 1.20 g (0.0048 mol) of 2,6-dichloro-3,5-dinitrotulune was added in portions within 30 min, then stirred for another 3 h. After the reaction was over by Thin-Layer Chromatography monitoring, the reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/10, as an eluent) to give 1.20 g of compound table 22-105 as yellow solid, m.p. 157-158° C.

$^1$H-NMR spectrum (300 MHz, internal standard: TMS, solvent CDC$_3$) δ(ppm): 2.02 (s, 3H), 8.29 (s, 2H), 8.65 (s, 1H), 8.95 (s, 1H).

Example 14

Preparation of Compound Table 22-120

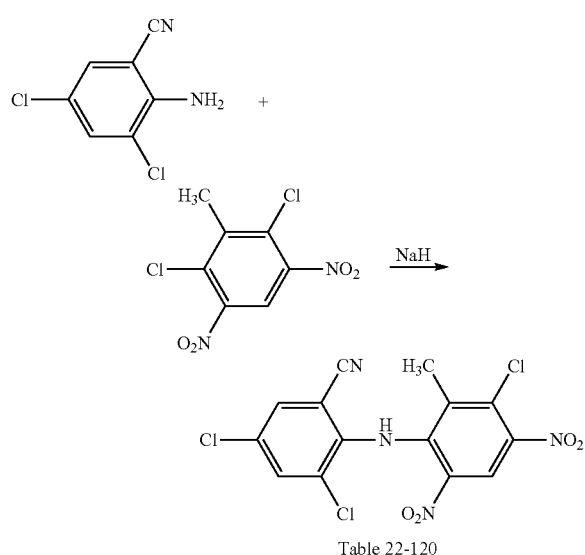

Table 22-120

The preparation is same to compound Table 22-39, m.p. 148-150° C.

$^1$H-NMR spectrum (300 MHz, internal standard: TMS, solvent CDC$_3$) δ(ppm): 2.07 (s, 3H), 7.53 (s, 1H), 7.72 (s, 1H), 8.71 (s, 1H), 8.97 (s, 1H).

Example 15

Preparation of Compound Table 22-121

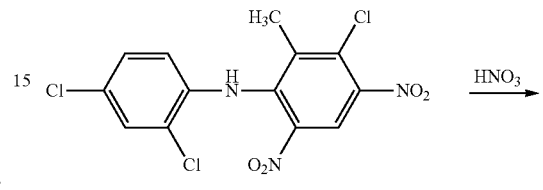

Table 22-39

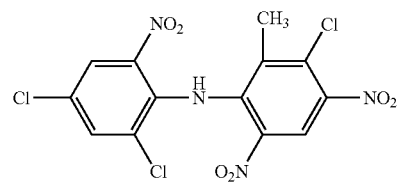

Table 22-121

0.56 g (0.0015 mol) of compound table 22-39 was dissolved in 5 mL of concentrated sulfuric acid (96%, the same below) and cooled to 0° C., 0.15 g of fuming nitric acid (95%) and 3 mL of concentrated sulfuric acid was mixed evenly and added to the flask, then the reaction mixture was stirred for another 5 min. After the reaction was over by Thin-Layer Chromatography monitoring, the reaction mixture was poured into ice water, the solid precipitated was filtered, and the filter mass was washed with water and dried to give 0.59 g of compound table 22-121 as brown solid, m.p. 156-158° C.

$^1$H-NMR spectrum (300 MHz, internal standard: TMS, solvent CDC$_3$) δ(ppm): 2.09 (s, 3H), 7.66 (s, 1H), 8.01 (s, 1H), 8.60 (s, 1H), 9.75 (s, 1H).

Example 16

Preparation of Compound Table 22-153

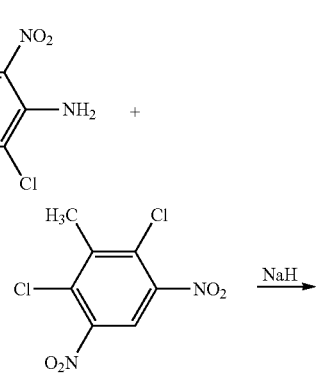

-continued

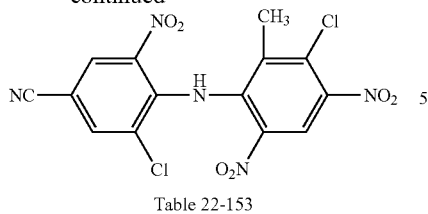

Table 22-153

The preparation is same to compound Table 22-39, m.p. 204-206° C.

$^1$H-NMR spectrum (300 MHz, internal standard: TMS, solvent CDC$_3$) δ(ppm): 2.23 (s, 3H), 7.87 (s, 1H), 8.38 (s, 1H), 8.51 (s, 1H), 10.00 (s, 1H).

Example 17

Preparation of Compound Table 22-206

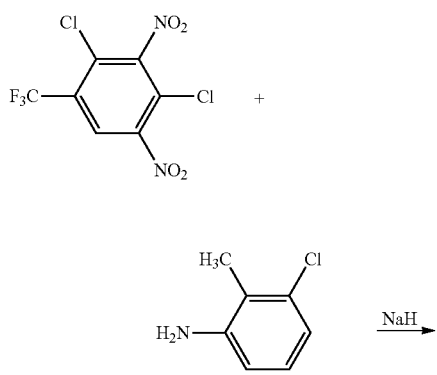

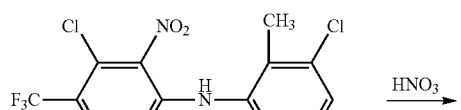

Table 22-206

The intermediate M prepared by the procedure of Example 13 was nitrated according to Example 2 to give compound Table 22-206 as reddish-brown solid, m.p. 136-138° C.

$^1$H-NMR spectrum (300 MHz, internal standard: TMS, solvent CDC$_3$) δ(ppm): 2.41 (s, 3H), 8.50 (s, 1H), 8.72 (s, 1H), 10.10 (s, 1H).

Example 18

Preparation of Compound Table 24-39

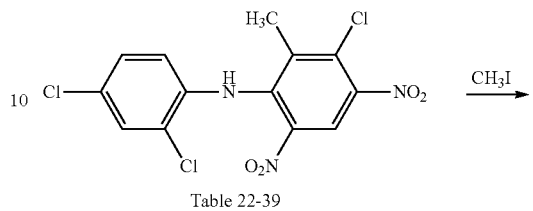

0.38 g (0.001 mol) of compound table 22-39 was added to a suspension of 0.10 g (0.0025 mol) of NaH (60%) and 10 mL of DMF, the mixture was stirred for 1 h and then added thereto 0.43 g (0.003 mol) of CH$_3$I, the resulting mixture was allowed to react for 5 h. After the reaction was over by Thin-Layer Chromatography monitoring, the reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/10, as an eluent) to give 0.15 g of compound table 22-39 as yellow solid, m.p. 142-144° C.

$^1$H-NMR spectrum (300 MHz, internal standard: TMS, solvent CDC$_3$) δ(ppm): 2.54 (s, 3H), 3.31 (s, 3H), 7.09 (d, 1H), 7.25 (d, 2H), 8.04 (s, 1H).

Example 19

Preparation of Compound Table 27-105

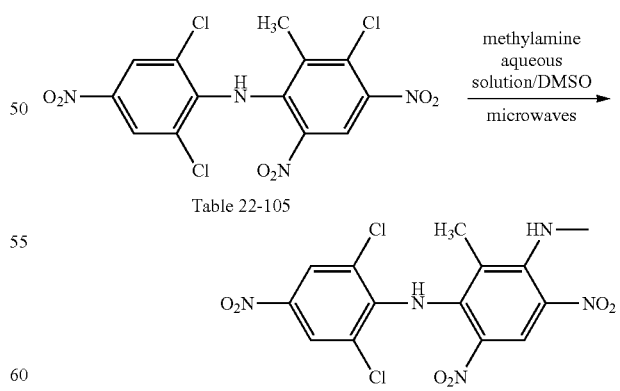

0.42 g of compound table 22-105 (0.001 mol) was added to a microwave vial and dissolved with 2.5 mL of DMSO, 1 mL of methylamine aqueous solution (25%) was added, the vial was lidded and put into the microwave reactor, then the reaction was carried out at 150° C. for 40 min. The reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=120, as an eluent) to give 0.25 g of compound table 27-105 as yellow solid, m.p. 218-219° C.

$^1$H-NMR spectrum (300 MHz, internal standard: TMS, solvent $CDC_3$) δ(ppm): 1.70 (s, 3H), 3.09 (d, 3H), 8.25 (d, 1H), 8.31 (s, 2H), 9.12 (s, 1H), 9.58 (s, 1H).

Example 20

Preparation of Compound Table 29-105

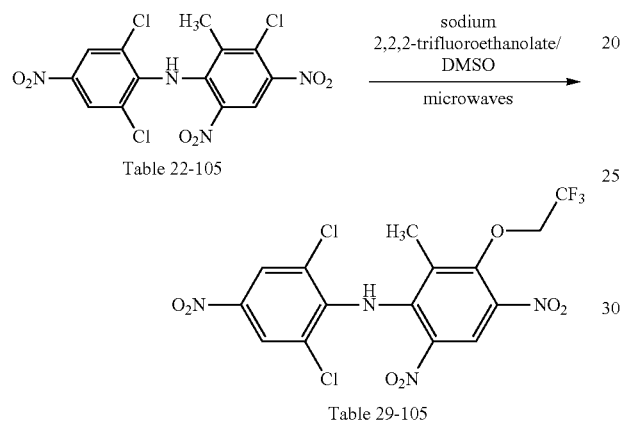

Table 29-105

0.42 g (1 mmol) of compound Table 22-105 and 2 mmol of sodium 2,2,2-trifluoroethanolate (made from trifluoroethanol and sodium) were dissolved in 3 ml of DMSO, heating to 150° C. for 10 min in microwave synthesizer (Biotage). Then the reaction mixture was poured into saturated brine, and extracted with ethyl acetate, the extract was washed by water and saturated brine, dried over anhydrous magnesium sulfate and concentrated under reduced pressure. The residue was purified through silica column (ethyl acetate/petroleum ether (boiling point range 60-90° C.)=120, as an eluent) to give 0.21 g of compound table 29-105 as yellow solid, m.p. 126-128° C.

$^1$H-NMR spectrum (300 MHz, internal standard: TMS, solvent $CDC_3$) δ(ppm): 1.83 (s, 3H), 4.42 (q, 2H), 8.30 (s, 2H), 8.85 (s, 1H), 9.20 (s, 1H).

Example 21

Preparation of Compound Table 30-105

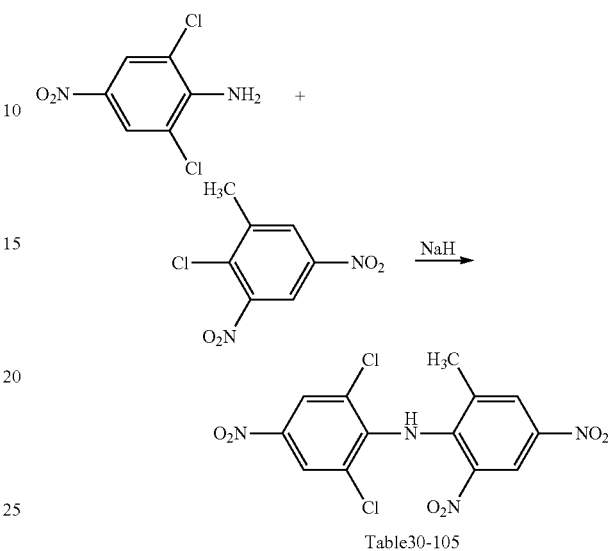

Table30-105

0.83 g (0.004 mol) of 2,6-dichloro-4-nitroaniline was added in portions to a suspension of 0.32 g (0.008 mol) of NaH (60%) and 10 mL of DMF, the mixture was stirred for 30 min after addition, 1.04 g (0.0048 mol) of 2-chloro-1-methyl-3,5-dinitrobenzene was added in portions within 30 min, then stirred for another 3 h. After the reaction was over by Thin-Layer Chromatography monitoring, the reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/10, as an eluent) to give 0.96 g of compound Table 30-105 as yellow solid, m.p. 146-148° C.

$^1$H-NMR spectrum (300 MHz, internal standard: TMS, solvent $CDC_3$) δ(ppm): 1.96 (s, 3H), 8.26 (d, 1H), 8.29 (s, 2H), 8.95 (d, 1H), 9.00 (s, 1H).

Other compounds of the present invention were prepared according to the above examples.

Physical properties and $^1$HNMR spectrum ($^1$HNMR, 300 MHz, internal standard: TMS, ppm) of some compounds of this invention are as follows:

| Table No. | Compound No. | Mp. (° C.) and $^1$HNMR (300 MHz, internal standard: TMS, solvent $CDCl_3$) |
|---|---|---|
| 6 | 3 | m.p. 208-210° C. δ ($CDCl_3$): 7.03 (s, 1H, NH), 7.27-7.38 (m, 3H, Ph-3,5,6-3H), 7.49-7.55 (m, 1H, Ph-4-H). |
| 6 | 6 | m.p. 212-214° C. δ ($CDCl_3$): 2.29 (s, 3H, $CH_3$), 7.00 (s, 1H, NH), 7.15 (d, H, Ph-6-H, J = 7.5 Hz), 7.28-7.34 (m, 3H, Ph-3,4,5-3H). |
| 6 | 10 | m.p. 258-260° C. δ ($CDCl_3$): 7.12 (s, 1H, NH), 7.24 (d, 1H, Ph-6-H, J = 7.5 Hz), 7.47 (t, 1H, Ph-4-H, J = 7.2 Hz), 7.68 (t, 1H, Ph-5-H, J = 7.5 Hz), 7.78 (d, 1H, Ph-3-H, J = 7.8 Hz). |
| 6 | 14 | m.p. 236-238° C. δ ($CDCl_3$): 7.12 (s, 1H, NH), 7.28-7.40 (m, 1H, Ph-6-H), 7.41-7.52 (m, 2H, Ph-2,4-2H), 7.54-7.62 (m, 1H, Ph-5-H). |
| 6 | 19 | m.p. 144-146° C. δ ($CDCl_3$): 1.30 (s, 9H, t-$C_4H_9$), 6.65 (m, 2H, Ph-2,6-2H), 7.16 (s, 1H, NH), 7.18 (m, 2H, Ph-3,5-2H). |
| 6 | 21 | m.p. 204-206° C. δ ($CDCl_3$): 7.09 (s, 1H, NH), 7.22-7.32 (m, 4H, Ph-2,3,5,6-4H). |

-continued

| Table No. | Compound No. | Mp. (° C.) and ¹HNMR (300 MHz, internal standard: TMS, solvent CDCl₃) |
|---|---|---|
| 6 | 23 | m.p. 259-261° C. δ (CDCl₃): 7.00 (s, 1H, NH), 7.17 (d, 2H, Ph-2,6-2H, J = 8.7 Hz), 7.42 (d, 2H, Ph-3,5-2H, J = 9.0 Hz). |
| 6 | 25 | m.p. 246-248° C. δ (CDCl₃): 2.29 (s, 3H, COOCH₃), 7.08 (s, 1H, NH), 7.17 (d, 2H, Ph-3,5-2H, J = 8.7 Hz), 8.10 (d, 2H, Ph-2,6-2H, J = 8.7 Hz). |
| 6 | 31 | m.p. 206-208° C. δ (CDCl₃): 6.88 (s, 1H, NH), 6.99 (t, 2H, Ph-5,6-2H, J = 8.1 Hz), 7.32 (d, 1H, Ph-3-H, J = 2.4 Hz). |
| 6 | 35 | m.p. 209-212° C. 6.93 (s, 1H, NH), 7.34 (t, 1H, Ph-3-H, J = 9.0 Hz), 7.52 (d, 1H, Ph-4-H, J = 7.2 Hz), 7.58-7.65 (m, 1H, Ph-3-H). |
| 6 | 38 | m.p. 218-220° C. δ (CDCl₃): 7.03 (s, 1H, NH), 7.13 (dd, 1H, Ph-6-H, ³J = 8.1 Hz, ⁴J = 0.9 Hz), 7.28 (t, 1H, Ph-5-H, J = 8.1 Hz), 7.47 (dd, 1H, Ph-4-H, ³J = 8.1 Hz, ⁴J = 0.9 Hz). |
| 6 | 41 | m.p. 235-237° C. δ (CDCl₃): 6.61 (s, 1H, NH), 7.36 (t, 1H, Ph-4-H, J = 7.2 Hz), 7.45 (d, 2H, Ph-3,5-2H, J = 7.2 Hz). |
| 6 | 42 | m.p. 240-242° C. δ (CDCl₃): 2.32 (s, 3H, Ph—CH₃), 6.93 (s, 1H, NH), 7.22-7.35 (m, 3H, Ph-3,4,5-H). |
| 6 | 44 | m.p. 238-242° C. δ (CDCl₃): 6.95 (s, 1H, NH), 7.05 (d, 2H, Ph-2,6-2H, J = 1.8 Hz), 7.32 (d, 1H, Ph-4-H, J = 1.5 Hz). |
| 6 | 47 | m.p. 166-168° C. δ (CDCl₃): 7.00 (s, 1H, NH), 7.20 (d, 1H, Ph-6-H, J = 8.4 Hz), 7.57 (dd, 1H, Ph-5-H, ³J = 8.4 Hz, ⁴J = 1.5 Hz), 7.78 (s, 1H, Ph-3-H). |
| 6 | 48 | m.p. 197-199° C. δ (CDCl₃): 7.02 (s, 1H, NH), 7.45 (s, 1H, Ph-6-H), 7.55 (d, 1H, Ph-4-H, J = 8.4 Hz), 7.65 (d, 1H, Ph-3-H, J = 8.4 Hz). |
| 6 | 49 | m.p. 220-222° C. 7.04 (d, 1H, Ph-6-H, J = 8.7 Hz), 7.07 (s, 1H, NH), 8.20 (dd, 1H, Ph-5-H, ³J = 9.0 Hz, ⁴J = 2.7 Hz), 8.42 (d, 1H, Ph-3-H, J = 2.7 Hz). |
| 6 | 77 | m.p. 200-202° C. δ (CDCl₃): 2.27 (s, 3H, Ph-2-CH₃), 6.86 (s, 1H, NH), 7.07 (d, 1H, Ph-6-H, J = 8.4 Hz), 7.23 (dd, 1H, Ph-5-H, ³J = 8.4 Hz, ⁴J = 2.1 Hz), 7.33 (s, 1H, Ph-3-H). |
| 6 | 78 | m.p. 140-142° C. δ (CDCl₃): 2.35 (s, 3H, CH₃), 6.99 (s, 1H, NH), 7.08 (d, 1H, Ph-6-H, J = 8.1 Hz), 7.19-7.25 (m, 1H, Ph-5-H), 7.46 (d, 1H, Ph-4-H, J = 8.7 Hz). |
| 6 | 80 | m.p. 198-200° C. δ (CDCl₃): 2.23 (s, 3H, CH₃), 2.34 (s, 3H, CH₃), 6.95 (s, 1H, NH), 6.95 (s, 1H, Ph-6-H), 7.13-7.22 (m, 2H, Ph-3,4-2H). |
| 6 | 83 | m.p. 204-205° C. δ (CDCl₃): 2.36 (s, 3H, COOCH₃), 3.92 (s, 3H, Ph-3-CH₃), 6.85 (s, 1H, NH), 7.12 (d, 1H, Ph-5-1H, J = 8.4 Hz), 7.92 (d, 1H, Ph-6-1H, J = 8.4 Hz), 8.02 (s, 1H, Ph-2-1H). |
| 6 | 84 | m.p. 216-218° C. δ (CDCl₃): 2.16 (s, 3H, CH₃), 3.89 (s, 3H, COOCH₃), 7.39 (t, 1H, Ph-4-H, J = 7.8 Hz), 7.51 (d, 1H, Ph-5-H, J = 7.8 Hz), 7.93 (d, 1H, Ph-3-H, J = 7.8 Hz). |
| 6 | 85 | m.p. 242-243° C. δ (CDCl₃): 7.07 (s, 1H, NH), 7.25 (d, 1H, Ph-6-H, J = 2.1 Hz), 7.42 (d, 1H, Ph-2-H, J = 2.4 Hz), 7.83 (d, 1H, Ph-5-H, J = 8.4 Hz). |
| 6 | 87 | m.p. 232-234° C. δ (CDCl₃): 6.94 (d, 1H, Ph-6-H, J = 9.3 Hz), 7.58 (dd, 1H, Ph-5-H, ³J = 9.0 Hz, ⁴J = 2.7 Hz), 8.26 (d, 1H, Ph-3-H, J = 2.7 Hz), 9.36 (s, 1H, NH). |
| 6 | 88 | m.p. 236-238° C. δ (DMSO): 7.02 (dd, 1H, Ph-6-H, ³J = 9.6 Hz, ⁴J = 2.7 Hz), 8.32 (dd, 1H, Ph-5-H, ³J = 9.3 Hz, ⁴J = 2.7 Hz), 8.63 (d, 1H, Ph-3-H, J = 2.7 Hz). |
| 6 | 95 | m.p. 201-203° C. δ (CDCl₃): 6.91 (s, 1H, NH), 7.72 (s, 2H, Ph-3,5-2H). |
| 6 | 98 | m.p. 259-261° C. δ (CDCl₃): 6.91 (s, 1H, NH), 7.74 (s, 2H, Ph-3,5-2H). |
| 6 | 103 | m.p. 267-269° C. δ (CDCl₃): 7.28-7.30 (m, 1H, NHPh-4-H), 7.40 t, 2H, NHPh-3,5-2H, J = 6.9 Hz), δ = 7.62 (d, 2H, NHPh-2,6-2H, J = 7.8 Hz), δ = 7.89-7.95 (m, 2H, NHCOPh-2,6-2H). |
| 6 | 107 | m.p. 232-234° C. δ (CDCl₃): 2.43 (s, 3H, Ph—CH₃), 6.86 (s, 1H, NH), 8.14 (s, 1H, Ph-5-1H), 8.26 (s, 1H, Ph-3-1H). |
| 6 | 108 | m.p. 196-198° C. δ (CDCl₃): 2.55 (s, 3H, CH₃), 6.99 (s, 1H, NH), 7.04 (d, 1H, Ph-6-H, J = 8.4 Hz), 7.36 (d, 1H, Ph-5-H, J = 8.4 Hz). |
| 6 | 109 | m.p. 194-196° C. δ (CDCl₃): 6.96 (s, 1H, NH), 7.67 (d, 1H, Ph-5-H, J = 2.1 Hz), 7.77 (d, 1H, Ph-3-H, J = 2.4 Hz). |
| 6 | 110 | m.p. 197-199° C. 6.86 (s, 1H, NH), 8.05 (dd, 1H, Ph-5-H, ³J = 9.9 Hz, ⁴J = 2.7 Hz), 8.28 (d, 1H, Ph-3-H, J = 2.4 Hz). |
| 6 | 113 | m.p. 248-250° C. δ (CDCl₃): 6.95 (s, 1H, NH), 8.37 (d, 1H, Ph-3-H, J = 2.7 Hz), 8.49 (d, 1H, Ph-5-H, J = 2.4 Hz). |
| 6 | 114 | m.p. 247-249° C. δ (CDCl₃): 6.96 (s, 1H, NH), 8.51 (s, 2H, Ph-3,5-2H). |
| 6 | 134 | m.p. 176-178° C. δ (CDCl₃): 1.15-1.27 (m, 6H, CH₃), 2.49 (q, 4H, CH₂, J = 7.5 Hz), 6.98 (s, 1H, NH), 7.14 (d, 1H, Ph-5-H, J = 8.4 Hz), 7.47 (d, 1H, Ph-3-H, J = 8.4 Hz). |
| 6 | 152 | m.p. 222-223° C. δ (CDCl₃): 2.22 (s, 3H, CH₃), 2.34 (s, 3H, CH₃), 6.88 (s, 1H, NH), 7.00 (s, 1H, Ph-6-H), 7.30 (s, 1H, Ph-3-H). |

-continued

| Table No. | Compound No. | Mp. (° C.) and ¹HNMR (300 MHz, internal standard: TMS, solvent CDCl₃) |
|---|---|---|
| 6 | 176 | m.p. 260-262° C. δ (CDCl₃): 2.06 (s, 3H, CH₃), 2.98 (d, 3H, NHCH₃, J = 4.8 Hz), 6.38 (s, 1H, CONH), 7.67 (s, 2H, Ph-3,5-2H), 9.38 (s, 1H, NH). |
| 6 | 178 | m.p. 240-242° C. δ (CDCl₃): 2.08 (s, 3H, CH₃), 2.93 (d, 3H, NCH₃, J = 5.1 Hz), 6.22 (s, 1H, CONH), 7.35-7.38 (m, 2H, Ph-3,5-2H), 8.59 (s, 1H, NH). |
| 6 | 180 | m.p. 180-182° C. δ (CDCl₃): 2.69 (s, 3H, CH₃), 7.12 (s, 1H, NH), 7.24-7.68 (m, 4H, Ph). |
| 6 | 206 | m.p. 156-158° C. δ (CDCl₃): 2.51 (s, 3H, CH₃), 8.67 (s, 1H, Ph), 8.89 (s, 1H, NH). |
| 9 | 8 | Yellow oil. δ (CDCl₃): 1.13-1.21 (m, 6H, CH₃), 3.46 (q, 4H, CH₂, J = 7.2 Hz), 6.90 (s, 1H, NH), 7.13 (t, 2H, Ph-2,6-2H, J = 7.5 Hz), 7.31 (d, 1H, Ph-4-H, J = 7.5 Hz), 7.42 (t, 2H, Ph-3,5-2H, J = 7.2 Hz). |
| 10 | 99 | m.p. 127-129° C. δ (CDCl₃): 3.22 (s, 6H, CH₃), 6.85 (s, 1H, NH), 8.32 (s, 2H, Ph-3,5-2H). |
| 12 | 99 | m.p. 198-200° C. δ (CDCl₃): 4.25 (s, 3H, CH₃), 6.87 (s, 1H, NH), 8.32 (s, 2H, Ph-3,5-2H). |
| 14 | 4 | m.p. 142-144° C. δ (CDCl₃): 4.14 (s, 3H, OCH₃), 4.17 (t, 3H, OCH₃, J = 4.2 Hz), 6.91 (s, 1H, Ph—NH—Ph), 7.18 (d, 2H, Ph-2,6-2H, J = 7.8 Hz), 7.32 (t, 1H, Ph-4-H, J = 7.2 Hz), 7.42 (t, 2H, Ph-3,5-2H, J = 7.5 Hz). |
| 16 | 2 | m.p. 176-178° C. δ (CDCl₃): 3.26 (d, 3H, NCH₃, J = 8.7 Hz), 3.37 (d, 3H, NCH₃ J = 8.1 Hz), 5.04 (br, 1H, Ph—NH—C), 5.26 (br, 1H, Ph—NH—C), 6.35 (s, 1H, Ph—NH—Ph), 7.04 (d, 2H, Ph-2,6-2H, J = 8.1 Hz), 7.14 (t, 1H, Ph-4-H, J = 7.2 Hz), 7.35 (t, 2H, Ph-3,5-2H, J = 7.5 Hz). |
| 22 | 11 | m.p. 158-160° C. δ (CDCl₃): 2.10 (s, 3H), 6.83 (d, 4H), 7.12 (m, 2H), 7.34 (m, 4H), 8.56 (s, 1H). |
| 22 | 22 | m.p. 172-174° C. δ (DMSO): 2.34 (s, 3H), 6.83 (d, 2H), 8.06 (d, 2H), 8.64 (s, 1H), 9.49 (s, 1H). |
| 22 | 23 | m.p. 184-186° C. δ (CDCl₃): 2.22 (s, 3H), 6.87 (d, 2H), 7.62 (d, 2H), 8.66 (s, 1H), 8.93 (s, 1H). |
| 22 | 24 | m.p. 91-94° C. δ (CDCl₃): 2.14 (s, 3H), 6.91 (d, 2H), 7.21 (d, 2H), 8.71 (s, 1H), 9.20 (s, 1H). |
| 22 | 31 | m.p. 136-138° C. δ (CDCl₃): 2.12 (s, 3H), 7.21 (m, 2H), 7.26 (m, 1H), 8.72 (s, 1H), 9.00 (s, 1H). |
| 22 | 47 | m.p. 106-108° C. δ (CDCl₃): 2.22 (s, 3H), 6.55 (d, 1H), 7.43 (d, 1H), 7.75 (s, 1H), 8.65 (s, 1H), 8.87 (s, 1H). |
| 22 | 48 | m.p. 110-112° C. δ (CDCl₃): 2.03 (s, 3H), 2.50 (s, 3H), 6.50 (d, 1H), 7.05 (t, 1H), 7.24 (d, 1H), 8.73 (s, 1H), 9.06 (s, 1H). |
| 22 | 50 | m.p. 191-193° C. δ (CDCl₃): 2.29 (s, 3H), 6.48 (d, 1H), 8.06 (d, 1H), 8.41 (s, 1H), 8.62 (s, 1H), 8.79 (s, 1H). |
| 22 | 56 | m.p. 146-148° C. δ (CDCl₃): 1.86 (s, 3H), 2.40 (s, 3H), 7.18 (m, 2H), 7.28 (m, 1H), 8.80 (s, 1H), 9.52 (s, 1H). |
| 22 | 58 | m.p. 133-135° C. δ (CDCl₃): 2.03 (s, 3H), 2.50 (s, 3H), 6.53 (d, 1H), 7.06 (t, 1H), 7.21 (d, 1H), 8.74 (s, 1H), 9.08 (s, 1H). |
| 22 | 61 | m.p. 206-208° C. δ (CDCl₃): 2.25 (s, 3H), 6.48 (d, 1H), 7.47 (d, 1H), 7.77 (s, 1H), 8.62 (s, 1H), 8.80 (s, 1H). |
| 22 | 63 | m.p. 259-261° C. δ (CDCl₃): 2.38 (s, 3H), 6.54 (d, 1H), 7.70 (d, 1H), 8.50 (s, 1H), 8.62 (s, 1H), 10.51 (s, 1H). |
| 22 | 80 | m.p. 121-123° C. δ (CDCl₃): 2.02 (s, 3H), 2.40 (s, 3H), 6.53 (d, 1H), 7.10 (d, 1H), 7.27 (s, 1H), 8.74 (s, 1H), 9.03 (s, 1H). |
| 22 | 86 | oil. δ (DMSO): 2.33 (s, 3H), 6.92 (d, 1H), 7.26 (s, 1H), 7.78 (d, 1H), 8.63 (s, 1H), 9.54 (s, 1H). |
| 22 | 88 | m.p. 204-205° C. δ (CDCl₃): 2.31 (s, 3H), 6.48 (d, 1H), 7.43 (d, 1H), 8.26 (s, 1H), 8.54 (s, 1H), 10.36 (s, 1H). |
| 22 | 89 | m.p. 185-186° C. δ (CDCl₃): 2.41 (s, 3H), 6.56 (d, 1H), 8.31 (d, 1H), 8.52 (s, 1H), 9.23 (s, 1H), 10.59 (s, 1H). |
| 22 | 93 | m.p. 148-150° C. δ (CDCl₃): 2.12 (s, 3H), 7.04 (d, 2H), 8.70 (s, 1H), 8.87 (s, 1H). |
| 22 | 94 | m.p. 154-156° C. δ (CDCl₃): 2.21 (s, 3H), 7.20 (m, 1H), 7.80 (m, 1H), 8.59 (s, 1H), 9.94 (s, 1H). |
| 22 | 95 | m.p. 140-142° C. δ (CDCl₃): 2.17 (s, 3H), 7.19 (d, 2H), 8.71 (s, 1H), 8.94 (s, 1H). |
| 22 | 97 | m.p. 142-143° C. δ (CDCl₃): 2.20 (s, 3H), 6.59 (s, 1H), 7.58 (s, 1H), 8.67 (s, 1H), 8.80 (s, 1H). |
| 22 | 98 | m.p. 160-162° C. δ (CDCl₃): 1.95 (s, 3H), 7.41 (s, 2H), 8.72 (s, 1H), 9.19 (s, 1H). |
| 22 | 104 | m.p. 180-182° C. δ (CDCl₃): 1.99 (s, 3H), 7.69 (s, 2H), 8.67 (s, 1H), 9.00 (s, 1H). |
| 22 | 106 | m.p. 169-171° C. δ (CDCl₃): 2.32 (s, 3H), 6.42 (s, 1H), 8.20 (s, 1H), 8.60 (s, 1H), 8.62 (s, 1H). |
| 22 | 107 | m.p. 132-134° C. δ (CDCl₃): 1.95 (s, 3H), 3.96 (s, 3H), 8.05 (s, 2H), 8.70 (s, 1H), 9.13 (s, 1H). |

-continued

| Table No. | Compound No. | Mp. (° C.) and ¹HNMR (300 MHz, internal standard: TMS, solvent CDCl₃) |
|---|---|---|
| 22 | 116 | m.p. 216-219° C. δ (CDCl₃): 2.30 (s, 3H), 7.88 (s, 2H), 8.48 (s, 1H), 8.85 (s, 1H). |
| 22 | 118 | m.p. 169-171° C. δ (CDCl₃): 2.26 (s, 3H), 8.50 (d, 2H), 8.99 (s, 1H), 10.14 (s, 1H). |
| 22 | 119 | m.p. 160-161° C. δ (CDCl₃): 2.13 (s, 3H), 2.54 (s, 3H), 6.40 (d, 1H), 7.19 (d, 1H), 8.68 (s, 1H), 8.96 (s, 1H). |
| 22 | 122 | m.p. 135-137° C. δ (CDCl₃): 2.16 (s, 3H), 7.95 (dd, 1H), 8.26 (t, 1H), 8.63 (s, 1H), 8.82 (s, 1H). |
| 22 | 123 | m.p. 151-153° C. δ (CDCl₃): 1.99 (s, 3H), 8.31 (d, 1H), 8.47 (d, 1H), 8.66 (s, 1H), 9.00 (s, 1H). |
| 22 | 124 | m.p. 96-97° C. δ (CDCl₃): 2.21 (s, 3H), 5.08 (m, 1H), 6.59 (s, 1H), 7.49 (s, 1H), 8.66 (s, 1H), 8.78 (s, 1H). |
| 22 | 125 | m.p. 192-194° C. δ (CDCl₃): 2.20 (s, 3H), 7.05 (s, 2H), 8.04 (s, 1H), 8.22 (s, 1H), 9.07 (s, 1H), 9.43 (s, 1H). |
| 22 | 126 | m.p. 125-127° C. δ (CDCl₃): 1.94 (s, 3H), 7.53 (s, 2H), 8.75 (s, 1H), 9.29 (s, 1H). |
| 22 | 129 | m.p. 151-154° C. δ (CDCl₃): 1.97 (s, 3H), 8.49 (s, 2H), 8.68 (s, 1H), 9.03 (s, 1H). |
| 22 | 130 | m.p. 172-175° C. δ (DMSO): 2.32 (s, 3H), 8.49 (s, 1H), 8.68 (s, 2H), 9.50 (s, 1H). |
| 22 | 133 | m.p. 131-132° C. δ (CDCl₃): 2.10 (s, 3H), 6.99 (t, 2H), 7.17 (m, 1H), 8.72 (s, 1H), 8.98 (s, 1H). |
| 22 | 139 | m.p. 158-161° C. δ (CDCl₃): 2.16 (s, 3H), 2.61 (s, 3H), 6.47 (d, 1H), 7.67 (d, 1H), 8.69 (s, 1H), 8.85 (s, 1H). |
| 22 | 140 | m.p. 137-139° C. δ (CDCl₃): 1.91 (s, 3H), 2.31 (s, 3H), 8.10 (s, 1H), 8.21 (s, 1H), 8.73 (s, 1H), 9.20 (s, 1H). |
| 22 | 152 | m.p. 160-162° C. δ (CDCl₃): 2.18 (s, 3H), 7.88 (d, 1H), 8.32 (d, 1H), 8.55 (s, 1H), 9.97 (s, 1H). |
| 22 | 163 | m.p. 241-243° C. δ (CDCl₃): 1.97 (s, 3H), 7.83 (s, 2H), 8.69 (s, 1H), 9.11 (s, 1H). |
| 22 | 164 | δ (CDCl₃): 1.94 (s, 3H), 3.03 (d, 3H), 7.78 (s, 2H), 8.70 (s, 1H), 9.14 (s, 1H). |
| 22 | 169 | m.p. 187-190° C. δ (CDCl₃): 2.18 (s, 3H), 8.23 (s, 2H), 8.57 (s, 1H), 10.39 (s, 1H). |
| 22 | 170 | oil. δ (CDCl₃): 2.27 (s, 3H), 8.52 (s, 1H), 9.09 (s, 2H), 10.93 (s, 1H). |
| 22 | 171 | m.p. 93-95° C. δ (CDCl₃): 2.19 (s, 3H), 8.14 (s, 2H), 8.56 (s, 1H), 10.42 (s, 1H). |
| 22 | 172 | m.p. 204-206° C. δ (DMSO): 2.32 (s, 3H), 7.03 (s, 1H), 8.73 (s, 1H), 8.86 (s, 1H), 10.40 (s, 1H). |
| 22 | 180 | m.p. 127-129° C. δ (CDCl₃): 2.36 (s, 3H), 6.55 (s, 1H), 8.40 (s, 1H), 8.54 (s, 1H), 10.31 (s, 1H). |
| 22 | 207 | m.p. 159-162° C. δ (CDCl₃): 2.16 (s, 3H), 8.23 (s, 1H), 8.63 (s, 1H), 8.91 (s, 1H). |
| 22 | 208 | m.p. 133-135° C. δ (CDCl₃): 2.07 (s, 3H), 7.70 (s, 1H), 8.69 (s, 1H), 9.22 (s, 1H). |
| 23 | 22 | m.p. 136-138° C. δ (CDCl₃): 2.22 (s, 3H), 6.70 (d, 2H), 7.41 (d, 1H), 8.00 (d, 2H), 8.22 (s, 1H). |
| 23 | 23 | m.p. 146-148° C. δ (CDCl₃): 2.19 (s, 3H), 6.70 (d, 2H), 7.36 (d, 1H), 7.53 (d, 2H), 7.96 (d, 1H), 8.20 (s, 1H). |
| 23 | 24 | m.p. 72-74° C. δ (CDCl₃): 2.12 (s, 3H), 6.75 (d, 2H), 7.12 (d, 2H), 7.25 (d, 1H), 7.98 (d, 1H), 8.46 (s, 1H). |
| 23 | 63 | m.p. 158-160° C. δ (CDCl₃): 2.30 (s, 3H), 6.47 (d, 1H), 7.59 (m, 2H), 7.94 (d, 1H), 8.60 (s, 1H), 10.21 (s, 1H). |
| 23 | 77 | m.p. 136-138° C. δ (CDCl₃): 2.22 (s, 3H), 6.75 (d, 1H), 7.03 (s, 1H), 7.45 (d, 1H), 7.67 (d, 1H), 7.99 (d, 1H), 8.16 (s, 1H). |
| 23 | 80 | oil. δ (CDCl₃): 2.02 (s, 3H), 2.38 (s, 3H), 6.34 (d, 1H), 7.00 (d, 1H), 7.18 (m, 2H), 7.98 (d, 1H), 8.30 (s, 1H). |
| 23 | 97 | m.p. 112-114° C. δ (CDCl₃): 2.18 (s, 3H), 6.38 (s, 1H), 7.38 (d, 1H), 7.50 (s, 1H), 7.97 (d, 1H), 8.11 (s, 1H). |
| 23 | 101 | oil. δ (CDCl₃): 1.92 (s, 3H), 7.22 (d, 1H), 7.58 (s, 2H), 7.93 (d, 1H), 8.39 (s, 1H). |
| 24 | 47 | m.p. 138-140° C. δ (CDCl₃): 2.58 (s, 3H), 3.37 (s, 3H), 7.23 (d, 1H), 7.48 (s, 1H), 7.57 (d, 1H), 8.08 (s, 1H). |
| 24 | 170 | m.p. 140-142° C. δ (CDCl₃): 2.58 (s, 3H), 3.30 (s, 3H), 8.38 (s, 1H), 8.57 (s, 2H). |
| 25 | 105 | m.p. 134-136° C. δ (CDCl₃): 1.79 (s, 3H), 3.96 (s, 3H), 8.29 (s, 2H), 8.74 (s, 1H), 9.18 (s, 1H). |
| 26 | 105 | m.p. 132-134° C. δ (CDCl₃): 2.11 (s, 3H), 2.39 (s, 3H), 8.29 (s, 2H), 8.47 (s, 1H), 8.95 (s, 1H). |
| 27 | 164 | m.p. 216-218° C. δ (CDCl₃): 1.56 (s, 3H), 3.04 (m, 6H), 7.80 (s, 2H), 8.18 (s, 1H), 9.13 (s, 1H), 9.58 (s, 1H). |
| 28 | 105 | m.p. 178-180° C. δ (CDCl₃): 1.71 (s, 3H), 2.86 (s, 6H), 8.29 (s, 2H), 8.66 (s, 1H), 9.45 (s, 1H). |
| 30 | 101 | m.p. 155-157° C. δ (CDCl₃): 1.90 (s, 3H), 7.66 (s, 2H), 8.21 (s, 1H), 8.98 (s, 1H), 9.19 (s, 1H). |

-continued

| Table No. | Compound No. | Mp. (° C.) and ¹HNMR (300 MHz, internal standard: TMS, solvent CDCl₃) |
|---|---|---|
| 30 | 104 | m.p. 183-185° C. δ (CDCl₃): 1.93 (s, 3H), 7.68 (s, 2H), 8.23 (d, 1H), 8.94 (d, 1H), 9.03 (s, 1H). |
| 30 | 120 | m.p. 175-177° C. δ (CDCl₃): 2.00 (s, 3H), 7.54 (d, 1H), 7.71 (d, 1H), 8.28 (d, 1H), 8.96 (d, 1H), 9.02 (s, 1H). |
| 30 | 122 | m.p. 108-110° C. δ (CDCl₃): 2.11 (s, 3H), 7.95 (dd, 1H), 8.26 (d, 1H), 8.31 (d, 1H), 8.79 (s, 1H), 8.92 (d, 1H). |

Cell Viability Assay

Example 22

In Vitro Cell Inhibition Assay (MTT Method)

The human cancer cell lines used for this assay were lung cancer A549 and leukemia HL-60.

The concentrations of compounds used for this assay were 0.01, 0.1, 1, 10, 100 μM. Based on in vitro cell culture, we use the MTT assay to detect the inhibitory rate of each compound.

The A549 or HL-60 cells were picked up from cell incubator, after washed for twice using PBS, cells were digested by 0.25% trypsin, and then add medium to terminate the digestion. After cells were collected using centrifuge and re-suspended, count cells under inverted microscope and add medium to make a density was $5 \times 10^4$ cells/mL. After 100 μL aliquots were added to each well of 96-well microtiter plates, cells were cultured in 5% incubator for overnight at 37° C., then the different concentration compounds were added to each well. After incubation for 48 h, MTT solution was added to each well and plates were then incubated for 4 h. The MTT tetrazolium was reduced to formazan by living cells. Then the formazan crystals were dissolved though adding DMSO to each well. The absorbance was read at 570 nm with a microplate reader.

Part of the test results are as follows:

TABLE 31

Proliferation inhibitory effect of the compounds on A549 cell (% of Control)

| Compounds No. | Concentration (μM) | | | | |
|---|---|---|---|---|---|
| | 100 | 10 | 1 | 0.1 | 0.01 |
| 6-1 | 19.8 | 20.4 | 16.9 | 12.1 | 13.1 |
| 6-23 | 93.8 | 93.7 | 2.5 | -1.8 | -0.8 |
| 6-35 | 92.7 | 58.6 | 1.0 | -0.8 | 0.5 |
| 6-39 | 92.6 | 24.9 | 19.6 | 18.8 | 18.3 |
| 6-41 | 92.0 | 84.0 | 13.1 | 0.7 | 3.8 |
| 6-93 | 98.2 | 80.3 | 74.8 | 39.4 | 12.1 |
| 6-98 | 93.2 | 90.1 | 11.7 | -0.7 | -2.5 |
| 6-99 | 86.3 | 83.6 | 55.0 | 0 | 0 |
| 6-113 | 93.7 | 75.6 | 2.6 | 2.9 | 9.2 |
| 6-114 | 94.9 | 82.1 | 11.5 | 2.8 | 10.1 |
| 22-33 | 90.3 | 78.7 | 61.3 | -1.1 | -1.6 |
| 22-93 | 91.4 | 73.7 | -0.2 | -1.8 | -2.2 |
| 22-101 | 97.5 | 66.4 | 19.1 | 21.4 | 13.7 |
| 22-105 | 89.8 | 80.6 | 49.9 | 8.8 | 16 |
| 22-120 | 92.1 | 86.8 | 9.8 | 0 | 0.8 |
| 22-121 | 89.5 | 51.2 | 9.9 | 12.4 | 6.2 |
| 22-153 | 85.2 | 60.6 | 14.7 | 0 | 3.7 |
| 22-208 | 91.3 | 83.2 | 2.4 | -1.2 | -1.0 |
| 25-105 | 93.7 | 78.0 | 0.9 | 2.2 | 3.1 |
| 28-105 | 89.6 | 54.9 | 2.7 | 5.3 | 4.1 |
| 29-105 | 91.9 | 94.2 | 72.7 | -0.5 | -0.2 |
| 30-104 | 91.8 | 78.4 | -0.1 | 1.1 | 2.4 |
| 30-120 | 92.0 | 84.0 | -0.7 | -0.9 | -1.5 |

TABLE 32

Proliferation inhibitory effect of the compounds on HL-60 cells (% of Control)

| Compounds No. | Concentration (μM) | | | | |
|---|---|---|---|---|---|
| | 100 | 10 | 1 | 0.1 | 0.01 |
| 6-1 | 61.9 | 63.9 | 18.8 | 10.4 | 11.5 |
| 6-3 | 94.5 | 72.2 | -2.1 | -6.3 | -7.1 |
| 6-10 | 77.1 | 78.5 | 9.8 | 16.1 | 21.8 |
| 6-23 | 90.6 | 93.2 | 23.1 | 10.8 | 2.3 |
| 6-35 | 89.9 | 72.3 | -1.8 | -5.0 | -8.3 |
| 6-39 | 80.8 | 78.5 | 31.0 | 14.7 | 11.9 |
| 6-41 | 87.9 | 86.5 | 7.8 | 3.9 | 6.5 |
| 6-93 | 74.8 | 72.3 | 70.7 | 51.8 | 0 |
| 6-98 | 95.1 | 91.7 | 30.0 | 10.1 | -2.5 |
| 6-99 | 54.8 | 56.5 | 60.2 | 34.2 | 8.6 |
| 6-109 | 94.4 | 52.4 | 2.9 | 2.2 | 0.1 |
| 6-113 | 93.1 | 85.4 | 9.3 | 8.8 | -3.8 |
| 6-114 | 93.2 | 87.5 | 20.7 | 10.0 | -0.4 |
| 6-205 | 91.9 | 59.5 | 5.8 | 12.6 | -3.4 |
| 22-24 | 94.3 | 82.4 | -9.3 | -16.7 | -22.4 |
| 22-33 | 81.2 | 66.2 | 54.3 | -1.8 | -4.9 |
| 22-61 | 89.8 | 85.7 | 11.0 | 7.8 | 5.2 |
| 22-88 | 94.1 | 79.1 | -24.6 | -32.9 | -35.2 |
| 22-93 | 95.4 | 70.4 | 6.8 | -7.1 | -3.6 |
| 22-95 | 95.4 | 76.0 | 32.6 | -4.0 | 0.3 |
| 22-98 | 91.0 | 77.7 | 9.5 | 1.3 | -7.3 |
| 22-101 | 64.7 | 73.4 | 48.6 | 5.5 | 8.3 |
| 22-104 | 94.0 | 60.5 | -2.1 | -7.3 | 4.1 |
| 22-105 | 53.8 | 70.4 | 71.1 | 31.7 | 27.2 |
| 22-107 | 94.4 | 65.4 | -7.0 | -9.3 | 2.8 |
| 22-120 | 61.0 | 63.1 | 19.7 | 20.5 | 9.6 |
| 22-121 | 61.2 | 73.6 | 47.6 | 12.5 | 13 |
| 22-122 | 94.6 | 57.2 | 11.7 | -1.9 | 6.3 |
| 22-153 | 65.8 | 73.4 | 59.6 | 7.3 | 12.9 |
| 22-207 | 90.5 | 61.9 | 0.4 | -3.6 | 7.3 |
| 22-208 | 91.2 | 91.2 | 28.9 | -14.0 | -8.0 |
| 25-105 | 88.0 | 80.2 | 20.0 | 4.4 | 3.1 |
| 26-105 | 88.0 | 80.2 | 20.0 | 4.4 | 3.1 |
| 28-105 | 77.2 | 88.4 | 13.3 | -3.7 | 4.9 |
| 29-105 | 91.5 | 95.1 | 94.7 | 70.2 | 11.2 |
| 30-101 | 80.7 | 57.3 | -0.3 | -14.2 | -6.4 |
| 30-104 | 93.3 | 88.0 | 65.3 | 31.6 | 21.8 |
| 30-105 | 89.0 | 85.6 | 80.6 | 43.6 | -6.8 |
| 30-120 | 95.7 | 95.9 | 70.6 | 39.2 | 23.6 |
| 30-122 | 82.4 | 61.3 | 18.0 | 7.4 | 10.7 |

Example 23

In Vitro Cell Inhibition Assay Using the Cell Counting Kit-8(CCK-8) Method

The human cancer cell lines used for this assay were: non-small cell lung cancer A549, NCI-H1650 and NCI-H358, leukemia HL-60, CCRF-CEM and MOLT-4, colon cancer HT-29 and COLO-205, pancreatic cancer BXPC-3, hepatocarcinoma SK-HEP-1, cervical cancer Hela, bladder cancer T24, prostate cancer DU-145 and PC-3, osteosarcoma MG-63, breast cancer MDA-MB-231, intracranial malignant melanoma A375, glioma U251, nasopharyngeal carcinoma CNE.

The concentrations of compounds used for this assay were 0.01, 0.1, 1, 10, 100 μM. Based on in vitro cell culture, we use the CCK-8 assay to detect the inhibitory rate of each compound.

The non-small cell lung cancer A549, NCI-H1650 and NCI-H358, colon cancer HT-29 and COLO-205, pancreatic cancer BXPC-3, hepatocarcinoma SK-HEP-1, cervical cancer Hela, bladder cancer T24, prostate cancer DU-145 and PC-3, osteosarcoma MG-63, breast cancer MDA-MB-231, intracranial malignant melanoma A375, glioma U251, nasopharyngeal carcinoma CNE were picked up from cell incubator. After the cell culture flasks gently shaking, culture fluid was discarded in clean bench. Then washed cells for twice using PBS, and add 0.25% trypsin to digest, when the cells were turning round, add medium to terminate digestion. Cells were collected and transferred to centrifuge tube. For the non-adherent cells HL-60, CCRF-CEM and MOLT-4, cell flasks were picked up from incubator and then transferred to the centrifuge tubes directly. After cells were collected using centrifuge at 1000 rpm/min for 5 min, the fluid was discarded. Then cells were washed for one time by PBS, discard fluid. Then add some medium, count cells under inverted microscope using blood cell counting plate, according the counting number to making the density of adherent cell was $1 \times 10^5$ cells/mL, the non-adherent cell was $2 \times 10^5$ cells/mL (the volumes of HL-60, CCRF-CEM, MOLT-4 are smaller than non-adherent cells, these cells added to each well was much more higher). Add 50 μL aliquots to each well of 96-well plates (the density of adherent cells was 5000 cells/well, non-adherent cells was 10000 cells/well). Blank control, Negative control, blank control with compounds and positive control wells were grouped, and three replicate wells were used for each data point in the experiments. Then the cells were cultured in 5% incubator for overnight at 37° C., Then the different concentration compounds were added to each well. After incubation for 48 h, according to the manufacturer's instructions, CCK-8 reagent (10 μl) was added and incubation was continued for a further 2-4 h. The absorbance (A) of each well was read at 450 nm using a plate reader.

TABLE 33

Proliferation inhibitory effect of the compounds on A549 cells (% of Control)

| Compounds No. | Concentration (μM) | | | | |
|---|---|---|---|---|---|
| | 100 | 10 | 1 | 0.1 | 0.01 |
| 6-24 | 87.36 | 60.31 | 31.44 | 24.27 | 22.06 |
| 6-25 | 81.32 | 55.87 | 17.11 | 18.59 | 15.66 |
| 6-47 | 99.91 | 55.57 | 53.58 | 49.86 | 42.56 |
| 6-93 | 98.18 | 87.64 | 70.04 | 19.35 | 14.77 |
| 6-95 | 98.69 | 97.88 | 78.63 | 56.27 | 39.65 |

TABLE 33-continued

Proliferation inhibitory effect of the compounds on A549 cells (% of Control)

| Compounds No. | Concentration (μM) | | | | |
|---|---|---|---|---|---|
| | 100 | 10 | 1 | 0.1 | 0.01 |
| 6-100 | 89.94 | 57.45 | 52.15 | 50.53 | 43.98 |
| 6-111 | 99.83 | 80.03 | 53.14 | 29.42 | 23.15 |
| 6-112 | 99.26 | 89.34 | 76.90 | 47.20 | 46.52 |
| 6-201 | 83.86 | 60.23 | 26.90 | 19.63 | 14.31 |

TABLE 34

Proliferation inhibitory effect of the compounds on HL-60 cells (% of Control)

| Compounds No. | Concentration (μM) | | | | |
|---|---|---|---|---|---|
| | 100 | 10 | 1 | 0.1 | 0.01 |
| 6-24 | 95.11 | 56.72 | 48.39 | 17.55 | 0.00 |
| 6-25 | 84.30 | 92.02 | 84.06 | 42.54 | 11.52 |
| 6-43 | 78.53 | 73.80 | 38.45 | 31.60 | 23.65 |
| 6-45 | 80.30 | 52.09 | 39.89 | 27.78 | 0.00 |
| 6-47 | 98.51 | 83.33 | 41.47 | 34.70 | 7.02 |
| 6-93 | 93.71 | 87.80 | 82.05 | 44.96 | 30.19 |
| 6-95 | 96.40 | 94.99 | 94.76 | 43.28 | 0.00 |
| 6-100 | 97.42 | 49.85 | 39.47 | 26.90 | 14.24 |
| 6-111 | 99.28 | 95.16 | 79.31 | 41.52 | 13.70 |
| 6-112 | 96.45 | 97.63 | 91.55 | 59.46 | 48.31 |
| 6-201 | 98.14 | 86.76 | 75.70 | 48.61 | 40.59 |

TABLE 35

The half maximal inhibitory concentration (IC50) of the compounds

| Tumor cells | Cell culture | Compound 6-93 | Gefitinib | Taxol |
|---|---|---|---|---|
| Non-small-cell carcinoma | A549 | 0.715 | 33.688 | 83.528 |
| | NCI-H1650 | 1.366 | 16.260 | 0.420 |
| | NCI-H358 | 0.443 | 1.166 | 0.278 |
| leukemia | HL-60 | 0.085 | 34.445 | <0.01 |
| | CCRF-CEM | <0.01 | 12.691 | <0.01 |
| | MOLT-4 | 0.167 | 25.839 | <0.01 |
| Colorectal Cancer | HT-29 | 0.224 | 18.310 | >100 |
| | COLO-205 | 0.125 | 6.973 | <0.01 |
| Prostate cancer | DU-145 | 0.646 | 3.371 | 17.428 |
| | PC-3 | 1.356 | 77.363 | 69.019 |
| cervical cancer | Hela | 1.509 | 35.442 | <0.01 |
| bladder cancer | T24 | 0.603 | 31.346 | 3.535 |
| nasopharyngeal | CNE | 6.078 | 43.682 | >100 |
| glioma | U251 | 1.616 | 26.801 | >100 |
| pancreatic cancer | BXPC-3 | 0.331 | 24.011 | <0.01 |
| hepatocarcinoma | SK-HEP-1 | 0.489 | 9.074 | 0.047 |
| breast cancer | MDA-MB-231 | 0.175 | >100 | 2.018 |
| melanoma | A375 | 0.160 | 35.463 | 55.345 |
| osteosarcoma | MG-63 | 0.196 | 33.706 | <0.01 |

What is claimed is:

1. A method of treating lung cancer or bladder cancer comprising administering to the subject in need thereof an effective amount of a substituted diphenylamine compound having the following general formula I:

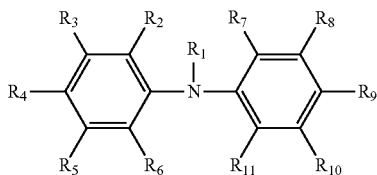

wherein:
$R_1$ is H;
$R_2$ and $R_6$ may be the same or different, respectively selected from the group consisting of H, halogen, CN and $NO_2$;
$R_3$ and $R_5$ are both H;
$R_4$ is selected from the group consisting of H, halogen, CN, $NO_2$, $C_1$-$C_8$haloalkyl, $C_1$-$C_8$haloalkoxy and $C_1$-$C_8$alkoxycarbonyl;
$R_7$ is Cl or $CH_3$;
$R_8$ is selected from the group consisting of H, halogen, $C_1$-$C_8$alkoxy and $C_1$-$C_8$haloalkoxy;
$R_9$ is selected from the group consisting of $NO_2$ and CN;
$R_{10}$ is selected from the group consisting of H and halogen; and
$R_{11}$ is CN or $NO_2$;
or salts thereof.

2. The method of claim 1, wherein $R_7$ is Cl, $R_9$ and $R_{11}$ are CN, and wherein the compound has the following general formula II:

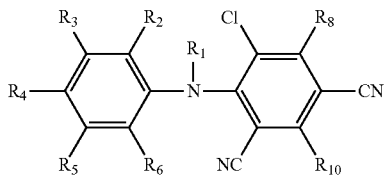

wherein:
$R_1$ is H;
$R_2$ and $R_6$ may be the same or different, respectively selected from the group consisting of H and halogen;
$R_3$ and $R_5$ are both H;
$R_4$ is selected from the group consisting of H, halogen, $C_1$-$C_8$haloalkyl, $C_1$-$C_8$haloalkoxy, and $C_1$-$C_8$alkoxycarbonyl; and
$R_8$ and $R_{10}$ are both halogen;
or the salts of the compounds having general formula II.

3. The method of claim 2, wherein, in the compound having the general formula II,
$R_1$ is H;
$R_2$ and $R_6$ may be the same or different, respectively selected from the group consisting of H, Cl, Br, and F;
$R_3$ and $R_5$ are both H;
$R_4$ is selected from the group consisting of H, Cl, Br, F, $C_1$-$C_4$haloalkyl, $C_1$-$C_4$haloalkoxy, and $C_1$-$C_4$alkoxycarbonyl; and
$R_8$ and $R_{10}$ are the same or different, respectively selected from the group consisting of Cl, Br, and F;
or the salts of the compounds having general formula II.

4. The method of claim 3, wherein, in the compound having the general formula II:
$R_1$ is H;
$R_2$ and $R_6$ are the same or different, respectively selected from the group consisting of H, F, Cl, and Br;
$R_3$ and $R_5$ are both H;
$R_4$ is selected from the group consisting of H, F, Cl, Br, $CF_3$, $CF_3O$, $CH_3OCO$, and $C_2H_5OCO$; and
$R_8$ and $R_{10}$ are the same or different, respectively selected from the group consisting of Cl and F;
or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

5. The method of claim 4, wherein, in the compound having the general formula II:
$R_1$ is H;
$R_2$ is selected from the group consisting of H, F, Cl, and Br;
$R_3$ is H;
$R_4$ is selected from the group consisting of H, F, Cl, Br, $CF_3$, $CF_3O$, and $CH_3OCO$;
$R_5$ is H;
$R_6$ is selected from the group consisting of H, F, Cl, and Br;
$R_8$ is Cl; and
$R_{10}$ is Cl;
or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

6. The method of claim 5, wherein, in the compound having the general formula II:
$R_1$, $R_3$ and $R_5$ are each a H;
$R_2$ and $R_6$ are the same or different, and wherein $R_2$ and $R_6$ are each independently selected from the group consisting of H, Cl and Br;
$R_4$ is selected from the group consisting of H, Cl, Br, $NO_2$, $CF_3$, $CF_3O$ and $CH_3OCO$;
$R_8$ and $R_{10}$ are each a Cl;
or the salts formed from the compounds of general formula II with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

7. The method of claim 6, wherein the compound has one of the following structures:

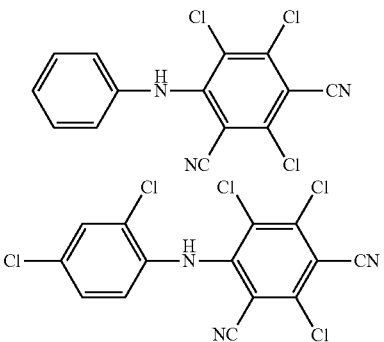

-continued

[chemical structure: 2,4-dichloro-6-chloro phenyl connected via NH to tetrachloro-dicyano phenyl]

[chemical structure: 4-nitro-2,6-dichlorophenyl NH tetrachloro-dicyano phenyl]

[chemical structure: 4-CF3-2,6-dichlorophenyl NH tetrachloro-dicyano phenyl]

[chemical structure: 4-Br-2,6-dichlorophenyl NH tetrachloro-dicyano phenyl]

[chemical structure: methyl 3,5-dichloro-4-(NH-tetrachloro-dicyanophenyl)benzoate]

[chemical structure: methyl 4-(NH-tetrachloro-dicyanophenyl)benzoate]

[chemical structure: 2,4,6-tribromophenyl NH tetrachloro-dicyano phenyl]

[chemical structure: 4-OCF3-2,6-dibromophenyl NH tetrachloro-dicyano phenyl]

8. The method of claim 1, wherein, in the compound having the general formula I:

$R_7$ is $CH_3$;

$R_{10}$ is H;

$R_{11}$ is $NO_2$; and the structures of the compound have a general formula III:

[Formula III: diphenylamine with $R_1$ on N; left ring bearing $R_2, R_3, R_4, R_5, R_6$ and a $CH_3$ group; right ring bearing $R_8, R_9$ and $NO_2$]

wherein:

$R_1$ is H;

$R_2$ and $R_6$ may be the same or different, respectively selected from the group consisting of H, halogen, CN, and $NO_2$;

$R_3$ and $R_5$ are both H;

$R_4$ is selected from the group consisting of H, halogen, CN, $NO_2$, and $C_1$-$C_8$haloalkyl;

$R_8$ is selected from the group consisting of H, halogen, $C_1$-$C_8$alkoxy, and $C_1$-$C_8$haloalkoxy; and $R_9$ is $NO_2$;

or the salts of the compounds having general formula III.

9. The method of claim 8, wherein, in the general formula III:

$R_1$ is H;

$R_2$ and $R_6$ may be the same or different, respectively selected from the group consisting of H, halogen, CN, and $NO_2$;

$R_3$ and $R_5$ are both H;

$R_4$ is selected from the group consisting of H, halogen, CN, $NO_2$, and $C_1$-$C_4$haloalkyl;

$R_8$ is selected from the group consisting of H, halogen, $C_1$-$C_4$alkoxy, and $C_1$-$C_4$haloalkoxy; and $R_9$ is $NO_2$;

or the salts of the compounds having general formula III.

10. The method of claim 9, wherein, in the compound of general formula III:

$R_1$ is H;

$R_2$ and $R_6$ may be the same or different, respectively selected from the group consisting of H, Cl, Br, F, CN, and $NO_2$;

$R_3$ and $R_5$ are both H;

$R_4$ is selected from the group consisting of H, Cl, Br, F, CN, $NO_2$, and $CF_3$;

$R_8$ is selected from the group consisting of H, Cl, Br, F, $C_1$-$C_3$alkoxy, and $C_1$-$C_3$haloalkoxy; and $R_9$ is $NO_2$, or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

11. The method of claim 10, wherein, in the compound of general formula III:

$R_1$ is H;

$R_2$ and $R_6$ may be the same or different, respectively selected from the group consisting of H, Cl, Br, F, CN, and $NO_2$;

$R_3$ and $R_5$ are both H;

$R_4$ is selected from the group consisting of H, Cl, Br, F, CN, $NO_2$, $CO_2H$, $C(=O)NH_2$, $C(=O)NHCH_3$, $CH_3$, $CF_3$, $OCF_2CHFCF_3$, $CO_2CH_3$ and 3-chloro-5-(trifluoromethyl)pyridin-2-yloxy;

$R_8$ is selected from the group consisting of H, Cl, OCH$_3$, and OCH$_2$CF$_3$; and $R_9$ is NO$_2$;

or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

12. The method of claim 11, wherein, in the compound of general formula III:

$R_1$, $R_3$ and $R_5$ are H;

$R_2$ is selected from the group consisting of Cl and F;

$R_4$ is selected from the group consisting of H, Cl, CN, NO$_2$ and CF$_3$;

$R_6$ is selected from the group consisting of F, Cl, CN and NO$_2$;

$R_8$ is selected from the group consisting of H, Cl and OCH$_2$CF$_3$; and $R_9$ is NO$_2$, or the salts formed from the compounds of general formula III with hydrochloric acid, sulfuric acid, nitric acid, hydrogen carbonic acid, carbonic acid, phosphoric acid, formic acid, acetic acid, trifluoroacetic acid, phenylsulfonic acid, p-toluenesulfonic acid, methylsulfonic acid, benzoic acid, citric acid, malic acid, tartaric acid, maleic acid, succinic acid, ascorbic acid or oxalic acid.

13. The method of claim 12, wherein the compound has one of the following structures:

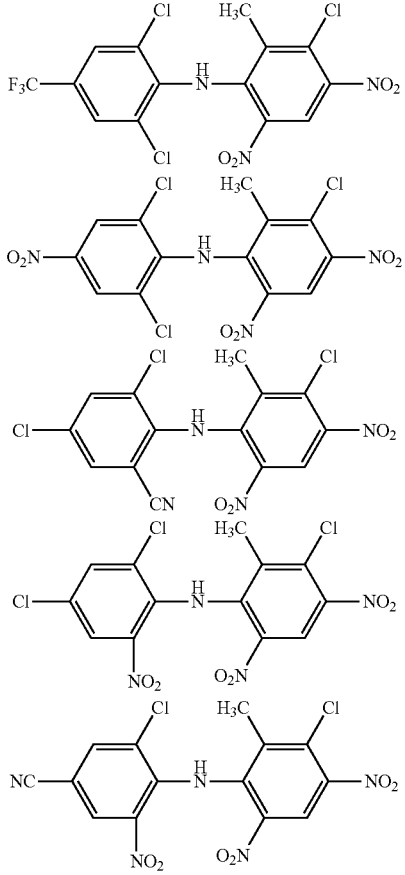

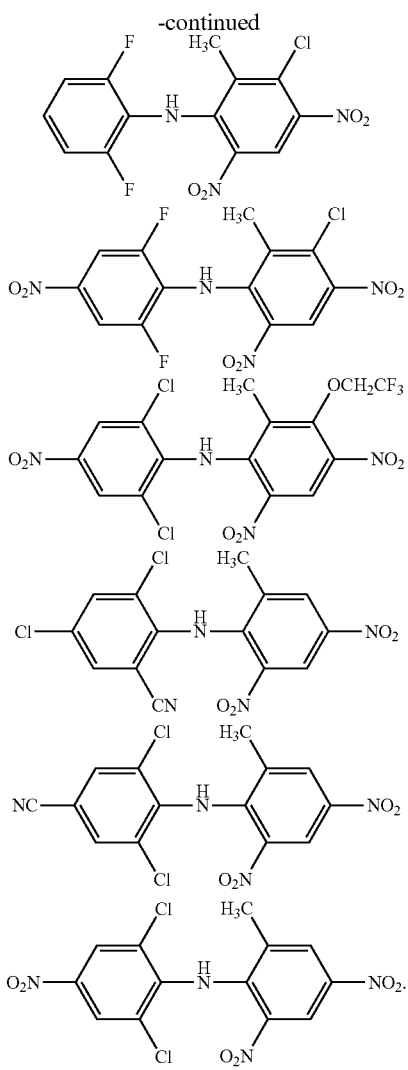

14. The method of claim 1, wherein the substituted diphenylamine compound or salt thereof as an active ingredient is administered through oral medication, a parenteral route or implantable medication pump.

15. The method of claim 14, wherein the active ingredient is one or more substituted diphenylamine compounds.

16. The method of claim 15, wherein the substituted diphenylamine compound and salt thereof is administered in the form of tablets, pills, capsule, granule, syrup, injection or freeze-dried powder injection.

17. A method of treating a cancer selected from the group consisting of lung cancer and bladder cancer, comprising: administering to the subject in need thereof an effective amount of a substituted diphenylamine compound of the following structure:

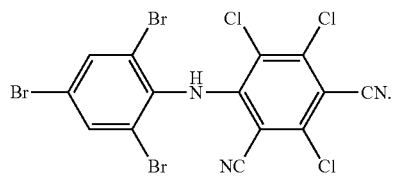

18. A method of treating a cancer selected from the group consisting of lung cancer and bladder cancer, osteosarcoma, and nasopharynx cancer, comprising administering to a subject in need thereof an effective amount of a pharmaceutical composition comprising a substituted diphenylamine compound having the following general formula I:

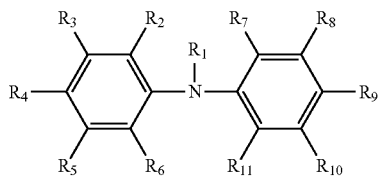

wherein:
$R_1$ is H;
$R_2$ and $R_6$ may be the same or different, respectively selected from the group consisting of H, halogen, CN, and $NO_2$;
$R_3$ and $R_5$ consisting of are both H;
$R_4$ is selected from the group consisting of H, halogen, CN, $NO_2$, COOH, $C_1$-$C_8$haloalkyl, $C_1$-$C_8$haloalkoxy, and $C_1$-$C_8$alkoxycarbonyl;
$R_7$ is Cl or $CH_3$;
$R_8$ is selected from the group consisting of H, halogen, $C_1$-$C_8$alkoxy, and $C_1$-$C_8$haloalkoxy;
$R_9$ is selected from the group consisting of $NO_2$ and CN;
$R_{10}$ is selected from the group consisting of H and halogen; and
$R_{11}$ is CN or $NO_2$,
or salts thereof
and a common drug carrier used in combination with the active ingredient.

* * * * *